(12) United States Patent
Blazar et al.

(10) Patent No.: US 12,270,050 B2
(45) Date of Patent: Apr. 8, 2025

(54) HUMAN T CELL DERIVED FROM T CELL-DERIVED INDUCED PLURIPOTENT STEM CELL AND METHODS OF MAKING AND USING

(71) Applicant: Regents of the University of Minnesota, Minneapolis, MN (US)

(72) Inventors: Bruce R. Blazar, Golden Valley, MN (US); Dharmeshkumar Patel, Falcon Heights, MN (US); Beau R. Webber, Coon Rapids, MN (US); Jakub Tolar, Minneapolis, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 377 days.

(21) Appl. No.: 16/060,651

(22) PCT Filed: Dec. 8, 2016

(86) PCT No.: PCT/US2016/065524
§ 371 (c)(1),
(2) Date: Jun. 8, 2018

(87) PCT Pub. No.: WO2017/100403
PCT Pub. Date: Jun. 15, 2017

(65) Prior Publication Data
US 2018/0362927 A1 Dec. 20, 2018

Related U.S. Application Data

(60) Provisional application No. 62/264,455, filed on Dec. 8, 2015.

(51) Int. Cl.
| | | |
|---|---|---|
| A61K 35/545 | (2015.01) | |
| A61K 35/17 | (2015.01) | |
| A61K 39/00 | (2006.01) | |
| C12N 5/074 | (2010.01) | |
| C12N 5/0783 | (2010.01) | |

(52) U.S. Cl.
CPC ........ *C12N 5/0636* (2013.01); *A61K 39/4611* (2023.05); *A61K 39/4631* (2023.05); *A61K 39/464412* (2023.05); *C12N 5/0696* (2013.01); C12N 2501/115 (2013.01); C12N 2501/125 (2013.01); C12N 2501/15 (2013.01); C12N 2501/155 (2013.01); C12N 2501/165 (2013.01); C12N 2501/2302 (2013.01); C12N 2501/2303 (2013.01); C12N 2501/2307 (2013.01); C12N 2501/2315 (2013.01); C12N 2501/26 (2013.01); C12N 2501/415 (2013.01); C12N 2501/42 (2013.01); C12N 2501/51 (2013.01); C12N 2501/515 (2013.01); C12N 2501/602 (2013.01); C12N 2501/603 (2013.01); C12N 2501/604 (2013.01); C12N 2501/606 (2013.01); C12N 2501/727 (2013.01); *C12N 2501/999* (2013.01); *C12N 2506/11* (2013.01); *C12N 2506/45* (2013.01); *C12N 2510/00* (2013.01); *C12N 2533/90* (2013.01)

(58) Field of Classification Search
CPC ................ C12N 5/0636; C12N 5/0696; C12N 2501/115; C12N 2501/125; C12N 2501/15; C12N 2501/155; C12N 2501/165; C12N 2501/26; C12N 2501/42; C12N 2501/51
See application file for complete search history.

(56) References Cited

U.S. PATENT DOCUMENTS

| | | | |
|---|---|---|---|
| 2014/0248248 A1 | 9/2014 | Zuniga-Pflucker | |
| 2015/0299656 A1* | 10/2015 | Gattinoni ........... | A61K 39/0011 435/325 |
| 2021/0017494 A1* | 1/2021 | Vodyanyk ............ | C12N 5/0638 |

FOREIGN PATENT DOCUMENTS

| | | | |
|---|---|---|---|
| EP | 2 853 590 B1 | 4/2015 | |
| EP | 2853590 A1 * | 4/2015 | ............. A61P 35/00 |
| EP | 2 915 880 A1 | 9/2015 | |
| WO | WO 2017/100403 A1 | 6/2017 | |

OTHER PUBLICATIONS

Themeli et al., "Generation of tumor-targeted human T lymphocytes from induced pluripotent stem cells for cancer therapy", 2013, Nature Biotechnology 31(10), p. 1-20.*
Flynn et al., "Stem memory T cells (TSCM)—their role in cancer and HIV immunotherapies", epub Jul. 18, 2014, Clinical and Translation Immunology 3, p. 1-7.*
Schmueck-Henneresse, Peripheral Blood-Derived Virus-Specific Memory Stem T Cells Mature to Functional Effector Memory Subsets with Self-Renewal Potency, J Immunology, 2015, pp. 5559-5567.*

(Continued)

*Primary Examiner* — Maria Marvich
(74) *Attorney, Agent, or Firm* — Mueting Raasch Group

(57) ABSTRACT

Induced pluripotent stem cells (iPSCs) derived from a T cell of a T cell subset. T cells derived from iPSCs derived from a T cell. Methods of deriving iPSCs from a T cell. Methods of deriving T cells from iPSCs including deriving a T cell of a T cell subset from an iPSC. Methods of engineering chimeric antigen receptor (CAR)-expressing or T cell receptor (TCR)-expressing iPSC. Methods of administering T cells derived using the methods disclosed. Induced pluripotent stem cell lines derived from T cells, methods of deriving induced pluripotent stem cell lines, and methods of deriving T cells from induced pluripotent stem cell lines.

18 Claims, 53 Drawing Sheets
Specification includes a Sequence Listing.

(56) References Cited

OTHER PUBLICATIONS

Crompton et al, Memoirs of a Reincarnated T Cell, Cell Stem Cell. 2013: 6-8.*
Lapenna et al, A Simple Model System Enabling Human CD34+ Cells to Undertake Differentiation Towards T Cells, Plosone, 2013, pp. 1-12.*
Seet et al, Generation of mature T cells from human hematopoietic stem/progenitor cells in artificial thymic organoids, Nat Methods. May 2017 ; 14(5): 521-530.*
Lugli et al, Harnessing Stem Cell-Like Memory T Cells for Adoptive Cell Transfer Therapy of Cancer, Developments in T Cell Based Cancer Immunotherapies, Cancer Drug Discovery and Development, 2015, pp. 183-209.*
International Patent Application No. PCT/US2016/065524, filed Dec. 8, 2016 International Search Report / Written Opinion issued Mar. 27, 2017; 18 pages.
International Patent Application No. PCT/US2016/065524, filed Dec. 8, 2016 International Preliminary Report on Patentability issued Jun. 21, 2018; 9 pages.
Adey, "Rapid, low-input, low-bias construction of shotgun fragment libraries by high-density in vitro transposition" 2010 *Genome Biology* 11(12):R119; 17 pgs.
Ahn, "Lineage relationships of human interleukin-22-producing CD56+ RORγt+ innate lymphoid cells and conventional natural killer cells" 2013 *Blood*, 121(12):2234-43.
Angelosanto, "Transcription factor regulation of CD8+ T-cell memory and exhaustion" 2010 *Immunol Rev.*, 236:167-75.
Aoyama, "Inhibiting retinoic acid signaling ameliorates graft-versus-host disease by modifying T-cell differentiation and intestinal migration" 2013 *Blood*, 122(12):2125-34.
Awong, "Human proT-cells generated in vitro facilitate hematopoietic stem cell-derived T-lymphopoiesis in vivo and restore thymic architecture" 2013 *Blood*, 122(26):4210-9.
Bachanova, "Clearance of acute myeloid leukemia by haploidentical natural killer cells is improved using IL-2 diphtheria toxin fusion protein" 2014 *Blood*, 123(25):3855-63. Published online Apr. 9, 2014 . . . .
Bachireddy, "Reversal of in situ T-cell exhaustion during effective human antileukemia responses to donor lymphocyte infusion" 2014 *Blood*, 123(9):1412-21. Published online Dec. 19, 2013.
Barao, "Mouse Ly49G2+ NK cells dominate early responses during both immune reconstitution and activation independently of MHC" 2011 *Blood*, 117(26):7032-41.
Barrett, "Relation of clinical culture method to T-cell memory status and efficacy in xenograft models of adoptive immunotherapy" 2014 *Cytotherapy*, 16(5):619-30. Published online Jan. 17, 2014.
Beyer, "Repression of the genome organizer SATB1 in regulatory T cells is required for suppressive function and inhibition of effector differentiation" 2011 *Nature Immunology*, 12(9):898-907.
Blazar, "Optimizing CAR T Cell Therapy," Grant Abstract, Grant No. CA065493 [online]. National Cancer Institute, project budget dates Sep. 1, 2018 to Aug. 31, 2019 [retrieved on Jun. 24, 2019]. Retrieved from the Internet: <URL:https://projectreporter.nih.gov/pr_Prj_info_desc_dtls.cfm?aid=9552730&icde=45210710&print=yes>; 2 pgs.
Blazar, "Murine recipients of fully mismatched donor marrow are protected from lethal graft-versus-host disease by the in vivo administration of rapamycin but develop an autoimmune-like syndrome" 1993 *Journal of Immunology*, 151(10):5726-41.
Blazar, "FK506 inhibits graft-versus-host disease and bone marrow graft rejection in murine recipients of MHC disparate donor grafts by interfering with mature peripheral T cell expansion post-transplantation" 1994 *Journal of Immunology*, 153(4):1836-46.
Bouchlaka, "Aging predisposes to acute inflammatory induced pathology after tumor immunotherapy" 2013 *J. Exp. Med.*, 210(11):2223-37.
Boyd, "Rewiring immunity: generating a functional thymus from hESCs . . . are we there yet?" 2013 *Cell Stem Cell*, 13(2):135-6.

Brentjens, "CD19-targeted T cells rapidly induce molecular remissions in adults with chemotherapy-refractory acute lymphoblastic leukemia" 2013 *Science Translational Med.*, 5(177):177ra38; 9 pgs.
Brown, "Derivation of induced pluripotent stem cells from human peripheral blood T lymphocytes" 2010 *PloS One*, 5(6):e11373; 9 pgs.
Brunstein, "Infusion of ex vivo expanded T regulatory cells in adults transplanted with umbilical cord blood: safety profile and detection kinetics" 2011 *Blood*, 117(3):1061-70.
Budde, "Combining a CD20 chimeric antigen receptor and an inducible caspase 9 suicide switch to improve the efficacy and safety of T cell adoptive immunotherapy for lymphoma" 2013 *PloS One*, 8(12):e82742; 10 pgs.
Buenrostro, "Transposition of native chromatin for fast and sensitive epigenomic profiling of open chromatin, DNA-binding proteins and nucleosome position" 2013 *Nature Methods*, 10(12):1213-8.
Cabezudo, "Quantitative analysis of CD79b, CD5 and CD19 in mature B-cell lymphoproliferative disorders" 1999 *Haematologica*, 84(5):413-8.
Cheng, "Zinc fingers hit off target" 2011 *Nature Medicine*, 17(10):1192-3.
Chevrier, "Systematic discovery of TLR signaling components delineates viral-sensing circuits" 2011 *Cell*, 147(4):853-67.
Coghill, "Separation of graft-versus-host disease from graft-versus-leukemia responses by targeting CC-chemokine receptor 7 on donor T cells" 2010 *Blood*, 115(23):4914-22.
Cope, "Chronic tumor necrosis factor alters T cell responses by attenuating T cell receptor signaling" 1997 *J. Exp. Med.*, 185(9):1573-84.
Crosetto, "Nucleotide-resolution DNA double-strand break mapping by next-generation sequencing" 2013 *Nature Methods*, 10(4):361-5.
Cruz, "Infusion of donor-derived CD19-redirected virus-specific T cells for B-cell malignancies relapsed after allogeneic stem cell transplant: a phase 1 study" 2013 *Blood*, 122(17):2965-73.
Darst, "Bisulfite Sequencing of DNA" 2010 *Current Protocols in Molecular Biology*, 91:Chapter 7: Unit 7.9.1-17; 20 pgs.
Davila, "CD19 CAR-targeted T cells induce long-term remission and B Cell Aplasia in an immunocompetent mouse model of B cell acute lymphoblastic leukemia" 2013 *PloS One*, 8(4):e61338; 14 pgs.
Davila, "Efficacy and toxicity management of 19-28z CAR T cell therapy in B cell acute lymphoblastic leukemia" Feb. 19, 2014 *Science Translational Med.*, 6(224):224ra25; 12 pgs.
Defrancesco, "CAR-T cell therapy seeks strategies to harness cytokine storm" Jul. 8, 2014 *Nat. Biotechnology*, 32:604.
Ding, "Chemotherapy rescues tumor-driven aberrant CD4+ T-cell differentiation and restores an activated polyfunctional helper phenotype" 2010 *Blood*, 115(12):2397-406.
Ding, "Immunosuppressive myeloid cells induced by chemotherapy attenuate antitumor CD4+ T cell responses through the PD-1/PD-L1 axis" 2014 *Cancer Res.*, 74(13): 3441-3453. Published online Apr. 29, 2014.
Doering, "Network analysis reveals centrally connected genes and pathways involved in CD8+ T cell exhaustion versus memory" 2012 *Immunity*, 37(6):1130-44.
Dong, "T cells: the usual subsets" Available online https://docs.abcam.com/pdf/immunology/t_cells_the_usual_subsets.pdf. Accessed Jun. 24, 2019. 1 pg.
Dotti, "Design and development of therapies using chimeric antigen receptor-expressing T cells" 2014 *Immunol Rev.*, 257(1):107-26. Published online Dec. 13, 2013.
Elcheva, "Direct induction of haematoendothelial programs in human pluripotent stem cells by transcriptional regulators" Jul. 14, 2014 *Nature Comm.*, 5:4372; 11 pgs.
Engels, "Retroviral vectors for high-level transgene expression in T lymphocytes" 2003 *Human Gene Therapy*, 14(12):1155-68.
Farber, "Human memory T cells: generation, compartmentalization and homeostasis" 2014 *Nat. Rev. Immunol.*, 14(1):24-35. Published online Dec. 13, 2013.
Felices, "Functional NK cell repertoires are maintained through IL-2Rα and Fas ligand" 2014 *J. Immunol.*, 192(8):3889-97. Published online Mar. 14, 2014.

(56) References Cited

OTHER PUBLICATIONS

Fusaki, "Efficient induction of transgene-free human pluripotent stem cells using a vector based on Sendai virus, an RNA virus that does not integrate into the host genome" 2009 *Proceedings of the Japan Academy, Series B*, 85(8):348-62.

Gangadharan, "DNA transposon Hermes inserts into DNA in nucleosome-free regions in vivo" 2010 *PNAS*, 107(51):21966-72.

Ganguly, "Donor $CD4^+$ $FoxP3^+$ regulatory T cells are required for post-transplant cyclophosphamide-mediated protection against murine graft-versus-host disease" 2014 *Blood*, 124(13):2131-2141. Published online Aug. 18, 2014.

Gattinoni,"Acquisition of full effector function in vitro paradoxically impairs the in vivo antitumor efficacy of adoptively transferred CD8+ T cells" 2005 *J. Clin. Invest.*, 115(6):1616-26.

Gattinoni, "Wnt signaling arrests effector T cell differentiation and generates CD8+ memory stem cells" 2009 *Nature Medicine*, 15(7):808-13.

Gattinoni, "Pharmacologic induction of CD8+ T cell memory: better living through chemistry" 2009 *Science Translational Med.*, 1(11):11ps12.

Gattinoni, "A human memory T cell subset with stem cell-like properties" 2012 *Nature Medicine*, 17(10):1290-7.

Gattinoni, "Paths to stemness: building the ultimate antitumour T cell" 2012 *Nat. Rev. Cancer*, 12(10):671-84.

Gattinoni, "Moving T memory stem cells to the clinic" 2013 *Blood*, 121(4):567-8.

Gattinoni, "Memory T cells officially join the stem cell club" Jul. 17, 2014 *Immunity*, 41(1):7-9.

Ginaldi, "Levels of expression of CD19 and CD20 in chronic B cell leukaemias" 1998 *J. Clin. Pathol.*, 51(5):364-9.

Gleason, "CD16xCD33 bispecific killer cell engager (BiKE) activates NK cells against primary MDS and Mdsc CD33+ targets" 2014 *Blood*, 123(19):3016-26. Published online Mar. 20, 2014.

Goryshin, "Tn5 in vitro transposition" 1998 *J. Biol. Chem.*, 273(13):7367-74.

Graef, "Serial transfer of single-cell-derived immunocompetence reveals stemness of $CD8^+$ central memory T cells" Jul. 17, 2014 *Immunity*, 41(1):116-26.

Grand View Research, "Stem Cell Market Size Analysis Report By Product (Adult, hESC, Induced Pluripotent), By Application (Regenerative Medicine, Drug Discovery & Development), By Technology, By Therapy, And Segment Forecasts, 2019-2025 (summary)" Available online: https://www.grandviewresearch.com/industry-analysis/stem-cells-market. Accessed Apr. 24, 2019. 9 pgs.

Grupp, "Chimeric antigen receptor-modified T cells for acute lymphoid leukemia" 2013 *NEJM.*, 368(16):1509-18.

Guttman, "Chromatin signature reveals over a thousand highly conserved large non-coding RNAs in mammals" 2009 *Nature*, 458(7235):223-7.

Haarberg, "Pharmacologic inhibition of PKCα and PKCθ prevents GVHD while preserving GVL activity in mice" 2013 *Blood*, 122(14):2500-11.

Heckl, "Generation of mouse models of myeloid malignancy with combinatorial genetic lesions using CRISPR-Cas9 genome editing" Jun. 22, 2014 *Nat. Biotechnol.*, 32(9):941-6.

Hippen, "Massive ex vivo expansion of human natural regulatory T cells ($T_{regs}$) with minimal loss of in vivo functional activity" 2011 *Sci. Trans. Med.*, 3(83):83ra41; 11 pgs.

Hollander, "Emerging strategies to boost thymic function" 2010 *Current Opinion in Pharmacology*, 10(4):443-53.

Jensen, "Design and implementation of adoptive therapy with chimeric antigen receptor-modified T cells" 2014 *Immunol Rev.*, 257(1):127-44. Published online Dec. 13, 2013.

Jensen, "Designing chimeric antigen receptors to effectively and safely target tumors" 2015 *Current Opinion in Immunology*, 33:9-15. Available online Jan. 23, 2015.

Ji, "Repression of the DNA-binding inhibitor Id3 by Blimp-1 limits the formation of memory $CD8^+$ T cells" 2011 *Nature Immunology*, 12(12):1230-7.

Johnson, "Diffuse large B-cell lymphoma: reduced CD20 expression is associated with an inferior survival" 2009 *Blood*, 113(16):3773-80.

June," Engineering lymphocyte subsets: tools, trials and tribulations" 2009 *Nature Reviews Immunology*, 9(10):704-16.

Kalos, "T cells with chimeric antigen receptors have potent antitumor effects and can establish memory in patients with advanced leukemia" 2011 *Science Translational Medicine*, 3(95):95ra73; 13 pgs.

Keller, "Wnt signaling controls the specification of definitive and primitive hematopoiesis from human pluripotent stem cells" 2014 *Nat. Biotechnol.*, 32(6):554-61. Published online May 18, 2014.

Kelly, "Short-term inhibition of p53 combined with keratinocyte growth factor improves thymic epithelial cell recovery and enhances T-cell reconstitution after murine bone marrow transplantation" 2010 *Blood*, 115(5):1088-97.

Kennedy, "T lymphocyte potential marks the emergence of definitive hematopoietic progenitors in human pluripotent stem cell differentiation cultures" 2012 *Cell Rep.*, 2(6):1722-35.

Klebanoff, "Central memory self/tumor-reactive CD8+ T cells confer superior antitumor immunity compared with effector memory T cells" 2005 *PNAS*, 102(27):9571-6.

Kochenderfer, "B-cell depletion and remissions of malignancy along with cytokine-associated toxicity in a clinical trial of anti-CD19 chimeric-antigen-receptor-transduced T cells" 2011 *Blood*, 119(12):2709-20.

Kochenderfer, "Donor-derived CD19-targeted T cells cause regression of malignancy persisting after allogeneic hematopoietic stem cell transplantation" 2013 *Blood*, 122(25):4129-39.

Kochenderfer, "Treating B-cell cancer with T cells expressing anti-CD19 chimeric antigen receptors" 2013 *Nat Rev Clin Oncol.*, 10(5):267-76.

Koestner, "PD-L1 blockade effectively restores strong graft-versus-leukemia effects without graft-versus-host disease after delayed adoptive transfer of T-cell receptor gene-engineered allogeneic $CD8^+$ T cells" 2011 *Blood*, 117(3):1030-41.

Krenger, "Polarized type 2 alloreactive $CD4^+$ and $CD8^+$ donor T cells fail to induce experimental acute graft-versus-host disease" 1995 *J. Immunol.*, 155(2):585-93.

Krenger, "Thymic T-cell development in allogeneic stem cell transplantation" 2011 *Blood*, 117(25):6768-76.

Kurachi, "The transcription factor BATF operates as an essential differentiation checkpoint in early effector $CD8^+$ T cells" Mar. 2, 2014 *Nat. Immunol.*, 15(4):373-83.

Lara-Astiaso, "Chromatin state dynamics during blood formation" 2014 *Science*, 345(6199):943-9. Published online Aug. 7, 2014.

Lee, "How I treat: current concepts in the diagnosis and management of cytokine release syndrome" 2014 *Blood*, 124(2):188-195. Published online May 29, 2014.

Lei, "T lineage differentiation from induced pluripotent stem cells" 2009 *Cellular Immunology*, 260(1):1-5.

Lei, "In vivo programming of tumor antigen-specific T lymphocytes from pluripotent stem cells to promote cancer immunosurveillance" 2011 *Cancer Research*, 71(14):4742-7.

Lei, "Directed differentiation of induced pluripotent stem cells towards T lymphocytes" 2012 *J. Vis. Exp.*, 2012(63):e3986; 9 pgs.

Lewin, "Direct evidence for new T-cell generation by patients after either T-cell-depleted or unmodified allogeneic hematopoietic stem cell transplantations" 2002 *Blood*, 100(6):2235-42.

Lin, "Intravital imaging of donor allogeneic effector and regulatory T cells with host dendritic cells during GVHD" 2014 *Blood*, 123(10):1604-14. Published online Jan. 10, 2014.

Lu, "Blimp-1 represses CD8 T cell expression of PD-1 using a feed-forward transcriptional circuit during acute viral infection" Mar. 3, 2014 *J. Exp. Med.*, 211(3):515-27.

Lugli, "Identification, isolation and in vitro expansion of human and nonhuman primate T stem cell memory cells" 2013 *Nature Protocols*, 8(1):33-42.

Lugli, "Superior T memory stem cell persistence supports long-lived T cell memory" 2013 *J. Clin. Invest.*, 123(2):594-9.

Mackall, "Age, thymopoiesis, and $CD4^+$ T-lymphocyte regeneration after intensive chemotherapy" 1995 *NEJM*, 332(3):143-9.

(56) References Cited

OTHER PUBLICATIONS

Martins, "Regulation and functions of Blimp-1 in T and B lymphocytes" 2008 *Ann. Rev. Immunol.*, 26:133-69.
Maude, "Chimeric Antigen Receptor T Cells for Sustained Remissions in Leukemia" Oct. 16, 2014 *NEJM*, 371(16):1507-1517.
Maus, "Antibody-modified T cells: CARs take the front seat for hematologic malignancies" 2014 *Blood*, 123(17):2625-35. Published online Feb. 27, 2014.
May, "Nfatc2 and tob1 have non-overlapping function in T cell negative regulation and tumorigenesis" Jun. 19, 2014 *PloS One*, 9(6):e100629; 13 pgs.
Mcfarland, "Identification of a human recent thymic emigrant phenotype" 2000 *PNAS*, 97(8):4215-20.
Miller "NCI First International Workshop on The Biology, Prevention, and Treatment of Relapse After Allogeneic Hematopoietic Stem Cell Transplantation: Report from the Committee on the Biology Underlying Recurrence of Malignant Disease following Allogeneic HSCT: Graft-versus-Tumor/Leukemia Reaction" 2010 *Biol Blood Marrow Transplant.*, 16(5):565-86.
Miller, "Control of acute myeloid leukemia relapse—dance between KIRs and HLA" 2012 *NEJM*, 367(9):866-8.
Moiani, "Lentiviral vector integration in the human genome induces alternative splicing and generates aberrant transcripts" 2012 *J. Clin. Invest.*, 122(5):1653-66.
Murase, "Increased mitochondrial apoptotic priming of human regulatory T cells after allogeneic hematopoietic stem cell transplantation" 2014 *Haematologica*, 99:1499-1508. Published online May 23, 2014.
Neumann, "Role of Blimp-1 in programing Th effector cells into IL-10 producers" Jul. 29, 2014 *J. Exp. Med.*, 211(9):1807-1819.
Ng, "A protocol describing the use of a recombinant protein-based, animal product-free medium (APEL) for human embryonic stem cell differentiation as spin embryoid bodies" 2008 *Nature Protocols*, 3(5):768-76.
Nishimura, "Generation of rejuvenated antigen-specific T cells by reprogramming to pluripotency and redifferentiation" 2013 *Cell Stem Cell*, 12(1):114-26.
Nurieva, "Bcl6 mediates the development of T follicular helper cells" 2009 *Science*, 325(5943):1001-5.
Osborn, "Synthetic zinc finger nuclease design and rapid assembly" 2011 *Human Gene Therapy*, 22(9):1155-65.
Osborn, "TALEN-based gene correction for epidermolysis bullosa" 2013 *Molecular Therapy*, 21(6):1151-9.
Osborn, "Fanconia Anemia Gene Editing by the CRISPR/Cas9 System" 2015 *Hum Gene Ther.*, 26(2):114-26. Published online Dec. 29. 2014.
Paley, "Progenitor and terminal subsets of CD8$^+$ T cells cooperate to contain chronic viral infection" 2012 *Science*, 338(6111):1220-5.
Papapetrou, "Harnessing endogenous miR-181a to segregate transgenic antigen receptor expression in developing versus post-thymic T cells in murine hematopoietic chimeras" 2009 *J. Clin. Invest.*, 119(1):157-68.
Parent, "Generation of functional thymic epithelium from human embryonic stem cells that supports host T cell development" 2013 *Cell Stem Cell*, 13(2):219-29.
Parish, "Chronic viral infection promotes sustained Th1-derived immunoregulatory IL-10 via BLIMP-1" Aug. 2014 *J. Clin. Invest.*, 124(8):3455-68. Published online Jul. 8, 2014.
Park, "Reprogramming of human somatic cells to pluripotency with defined factors" 2008 *Nature*, 451(7175):141-6.
Penaloza-Macmaster, "Opposing effects of CD70 costimulation during acute and chronic lymphocytic choriomeningitis virus infection of mice" 2011 *J. Virology*, 85(13):6168-74.
Plesa, "TCR affinity and specificity requirements for human regulatory T-cell function" 2012 *Blood*, 119(15):3420-30.
Quigley, "Transcriptional analysis of HIV-specific CD8$^+$ T cells shows that PD-1 inhibits T cell function by upregulating BATF" 2010 *Nature Medicine*, 16(10):1147-51 (Author Manuscript).
Raab, "A Comparative View on Human Somatic Cell Sources for iPSC Generation" Nov. 6, 2014 *Stem Cells Int.*, 2014:768391; 12 pgs.
Ran, "Genome engineering using the CRISPR-Cas9 system" 2013 *Nat Protoc.*, 8(11):2281-2308.
Refaeli, "The B cell antigen receptor and overexpression of MYC can cooperate in the genesis of B cell lymphomas" 2008 *PLoS Biol.*, 6(6):e152; 18 pgs.
Reportstack, "Cancer Immunotherapy Market: Immune Checkpoint Inhibitors, Cancer Vaccines, and Adoptive T-cell Therapies (summary)" Online: www.prweb.com/releases/2014/09/prweb12170919.htm. Accessed Apr. 25, 2019.
Research and Markets, "Global Hematopoietic Stem Cell Transplantation Market Analysis & Trends—Application, Transplant Type—Forecast to 2025 (summary)" Online: https://www.researchandmarkets.com/reports/3971860/global-hematopoietic-stem-cell-transplantation. Accessed: Apr. 24, 2019. 9 pgs.
Researchmoz, "Global Induced Pluripotent Stem Cells Market Size, Status and Forecast 2018-2025 (abstract)" Online: https://www.researchmoz.US/global-induced-pluripotent-stem-cells-market-size-status-and-forecast-2018-2025-report.html. Accessed: Apr. 24, 2019.
Rizwan, "Peritransplant palifermin use and lymphocyte recovery after T-cell replete, matched related allogeneic hematopoietic cell transplantation" 2011 *Am. J. Hematol.*, 86(10):879-82.
Rubio, "Mechanisms of the antitumor responses and host-versus-graft reactions induced by recipient leukocyte infusions in mixed chimeras prepared with nonmyeloablative conditioning: a critical role for recipient CD4$^+$ T cells and recipient leukocyte infusion-derived IFN-γ-producing CD8$^+$ T cells" 2005 *J. Immunol.*, 175(2):665-76.
Sakuishi, "Targeting Tim-3 and PD-1 pathways to reverse T cell exhaustion and restore anti-tumor immunity" 2010 *J. Exp. Med.*, 207(10):2187-94.
Sckisel, "Influenza infection results in local expansion of memory CD8$^+$ T cells with antigen non-specific phenotype and function" 2013 *Clinical and Experimental Immunology*, 175(1):79-91.
Seki, "Generation of induced pluripotent stem cells from human terminally differentiated circulating T cells" 2010 *Cell Stem Cell*, 7(1):11-4.
Seki, "Derivation of induced pluripotent stem cells from human peripheral circulating T cells" 2011 *Current Protocols in Stem Cell Biology*, Chapter 4: Unit4A3. John Wiley & Sons; 2011.
Shalem, "Genome-scale CRISPR-Cas9 knockout screening in human cells" 2014 *Science*, 343(6166):84-7. Published online: Dec. 12, 2013.
Sharma, "An inherently bifunctional subset of Foxp3$^+$ T helper cells is controlled by the transcription factor Eos" 2013 *Immunity*, 38(5):998-1012.
Shin, "A role for the transcriptional repressor Blimp-1 in CD8$^+$ T cell exhaustion during chronic viral infection" 2009 *Immunity*, 31(2):309-20.
Shin, "Epigenetic modifications induced by Blimp-1 Regulate CD8$^+$ T cell memory progression during acute virus infection" 2013 *Immunity*, 39(4):661-75.
Socie, "Overview of the immune biology of allogeneic HSCT." In: Immune Biology of Allogeneic Hematopoietic Stem Cell Transplantation. Academic Press: 2012. Chapter as listed, publisher page, table of contents.
Stelekati, "Bystander chronic infection negatively impacts development of CD8$^+$ T cell memory" May 15, 2014 *Immunity*, 40(5):801-13.
Storek, "Immunity of patients surviving 20 to 30 years after allogeneic or syngeneic bone marrow transplantation" 2001 *Blood*, 98(13):3505-12; including 2pgs erratum.
Storek, "Factors influencing T-lymphopoiesis after allogeneic hematopoietic cell transplantation" 2002 *Transplantation*, 73(7):1154-8.
Sturgeon, "Wnt signaling controls the specification of definitive and primitive hematopoiesis from human pluripotent stem cells" May 18, 2014 *Nat. Biotechnol.*, 32(6):554-61.
Sun, "Directed differentiation of human embryonic stem cells into thymic epithelial progenitor-like cells reconstitutes the thymic microenvironment in vivo" 2013 *Cell Stem Cell*, 13(2):230-6.

(56) References Cited

OTHER PUBLICATIONS

Takahashi, "Induction of pluripotent stem cells from mouse embryonic and adult fibroblast cultures by defined factors" 2006 *Cell*, 126(4):663-76.
Talvensaari, "A broad T-cell repertoire diversity and an efficient thymic function indicate a favorable long-term immune reconstitution after cord blood stem cell transplantation" 2002 *Blood*, 99(4):1458-64.
Tammana, "4-1BB and CD28 signaling plays a synergistic role in redirecting umbilical cord blood T cells against B-cell malignancies" 2010 *Human Gene Therapy*, 21(1):75-86.
Tawara, "Interleukin-6 modulates graft-versus-host responses after experimental allogeneic bone marrow transplantation" 2010 *Clin Cancer Res.*, 17(1):77-88.
Taylor, "FTY720 markedly increases alloengraftment but does not eliminate host anti-donor T cells that cause graft rejection on its withdrawal" 2012 *Biol Blood Marrow Transplant.*, 18(9):1341-52.
Themeli, "Generation of tumor-targeted human T lymphocytes from induced pluripotent stem cells for cancer therapy" 2013 *Nat. Biotechnol.*, 31(10):928-33.
Thurman, "The accessible chromatin landscape of the human genome" 2012 *Nature*, 489(7414):75-82.
Tietze, "Delineation of antigen-specific and antigen-nonspecific $CD8^+$ memory T-cell responses after cytokine-based cancer immunotherapy" 2012 *Blood*, 119(13):3073-83.
Tolar, "Hematopoietic differentiation of induced pluripotent stem cells from patients with mucopolysaccharidosis type I (Hurler syndrome)" 2011 *Blood*, 117(3):839-47.
Tolar, "Induced pluripotent stem cells from individuals with recessive dystrophic epidermolysis bullosa" 2011 *Journal Invest. Dermatol.*, 131(4):848-56.
Tolar, "Keratinocytes from induced pluripotent stem cells in junctional epidermolysis bullosa" 2012 *Journal Invest. Dermatol.*, 133(2):562-5.
Torikai, "Toward eliminating HLA class I expression to generate universal cells from allogeneic donors" 2013 *Blood*, 122(8):1341-9.
Transparency Market Research, "Global Stem Cells Market: Players Partnering with Pharmaceutical Companies to Surge Ahead, finds TMR (summary)" Online: http://www.transparencymarketresearch.com/stem-cellsmarket.htm. Accessed: Jun. 24, 2019.
Trokovic, "Generation of iPSC line HEL47.2 from healthy human adult fibroblasts" 2015 *Stem Cell Res.*, 15(1):263-5. Available online Jun. 2, 2015.
Van Der Stegen, "The pharmacology of second-generation chimeric antigen receptors" Jul. 1, 2015 *Nature Reviews Drug Discovery*, 14(7):499-509.
Vizcardo, "Regeneration of human tumor antigen-specific T cells from iPSCs derived from mature $CD8^+$ T cells" 2013 *Cell Stem Cell*, 12(1):31-6.
Wagner, "Resurrecting the recalcitrant T-cell" 2011 *Blood*, 118(16):4302-3.
Wagner, "Phase I/II Trial of StemRegenin-1 Expanded Umbilical Cord Blood Hematopoietic Stem Cells Supports Testing as a Stand-Alone Graft" 2016 *Cell Stem Cell*, 18:144-155. Published online Dec. 5, 2015.
Wakao, "Expansion of functional human mucosal-associated invariant T cells via reprogramming to pluripotency and redifferentiation" 2013 *Cell Stem Cell*, 12(5):546-58.
Wang, "A transgene-encoded cell surface polypeptide for selection, in vivo tracking, and ablation of engineered cells" 2011 *Blood*, 118(5):1255-63.
Wang, "The complex and central role of interferon-gamma in graft-versus-host disease and graft-versus-tumor activity" 2014 *Immunol Rev.*, 258(1):30-44. Published online Feb. 11, 2014.
Webber, "DNA methylation of Runx 1 regulatory regions correlates with transition from primitive to definitive hematopoietic potential in vitro and in vivo" 2013 *Blood*, 122(17):2978-86.
Weinberg, "Factors affecting thymic function after allogeneic hematopoietic stem cell transplantation" 2001 *Blood*, 97(5):1458-66.
Wherry, "Molecular signature of $CD8^+$ T cell exhaustion during chronic viral infection" 2007 *Immunity*, 27(4):670-84.
Wherry, "T cell exhaustion" 2011 *Nature Immunology*, 12(6):492-9.
Xu, "Closely related T-memory stem cells correlate with in vivo expansion of CAR.CD19-T cells and are preserved by IL-7 and IL-15" 2014 *Blood*, 123(24):3750-9. Published online Apr. 29, 2014.
Yang, "Diminished expression of CD19 in B-cell lymphomas" 2005 *Cytometry Part B (Clinical Cytometry)*, 63B:28-35.
Yang, "Modulating the differentiation status of ex vivo-cultured anti-tumor T cells using cytokine cocktails" 2012 *Cancer Immunol Immunother.*, 62(4):727-36.
Youngblood, "Chronic virus infection enforces demethylation of the locus that encodes PD-1 in antigen-specific $CD8^+$ T cells" 2011 *Immunity*, 35(3):400-12.
Yusa, "Generation of transgene-free induced pluripotent mouse stem cells by the piggyBac transposon" 2009 *Nat Methods*, 6(5):363-9.
Zhang, "Chemokine treatment rescues profound T-lineage progenitor homing defect after bone marrow transplant conditioning in mice" 2014 *Blood*, 124(2):296-304. Published online May 29, 2014.
Zhou, "Tissue-specific expression of the human CD19 gene in transgenic mice inhibits antigen-independent B-lymphocyte development" 1994 *Mol Cell Biol.*, 14(6):3884-94.
Zhou, "Program death-1 signaling and regulatory T cells collaborate to resist the function of adoptively transferred cytotoxic T lymphocytes in advanced acute myeloid leukemia" 2010 *Blood*, 116(14):2484-93.
Zhou, "Charting histone modifications and the functional organization of mammalian genomes" 2011 *Nat. Rev. Gen.*, 12(1):7-18.
Zhou, "Coexpression of Tim-3 and PD-1 identifies a $CD8^+$ T-cell exhaustion phenotype in mice with disseminated acute myelogenous leukemia" 2011 *Blood*, 117(17):4501-10.
Zhou, "In vivo discovery of immunotherapy targets in the tumour microenvironment" 2014 *Nature*, 506(7486):52-7. Published online Jan. 29, 2014.
Zuklys, "MicroRNAs control the maintenance of thymic epithelia and their competence for T lineage commitment and thymocyte selection" 2012 *J. Immunol.*, 189(8):3894-904; including 3 pgs supplemental information.
Miller, "Expansion and Homing of Adoptively Transferred Human Natural Killer Cells in Immunodeficient Mice Varies with Product Preparation and In Vivo Cytokine Administration: Implications for Clinical Therapy," Aug. 2014, *Biol Blood Marrow Transplant.*, 20(8):1252-7.
Riddell, "Reprogramming committed murine blood cells to induced hematopoietic stem cells with defined factors, " Apr. 2014, *Cell*, 157(3):549-64.
Tolar, "Patient-specific naturally gene-reverted induced pluripotent stem cells in recessive dystrophic epidermolysis bullosa," May 2014 *Journal Invest. Dermatol.*, 134(5):1246-1254.

* cited by examiner

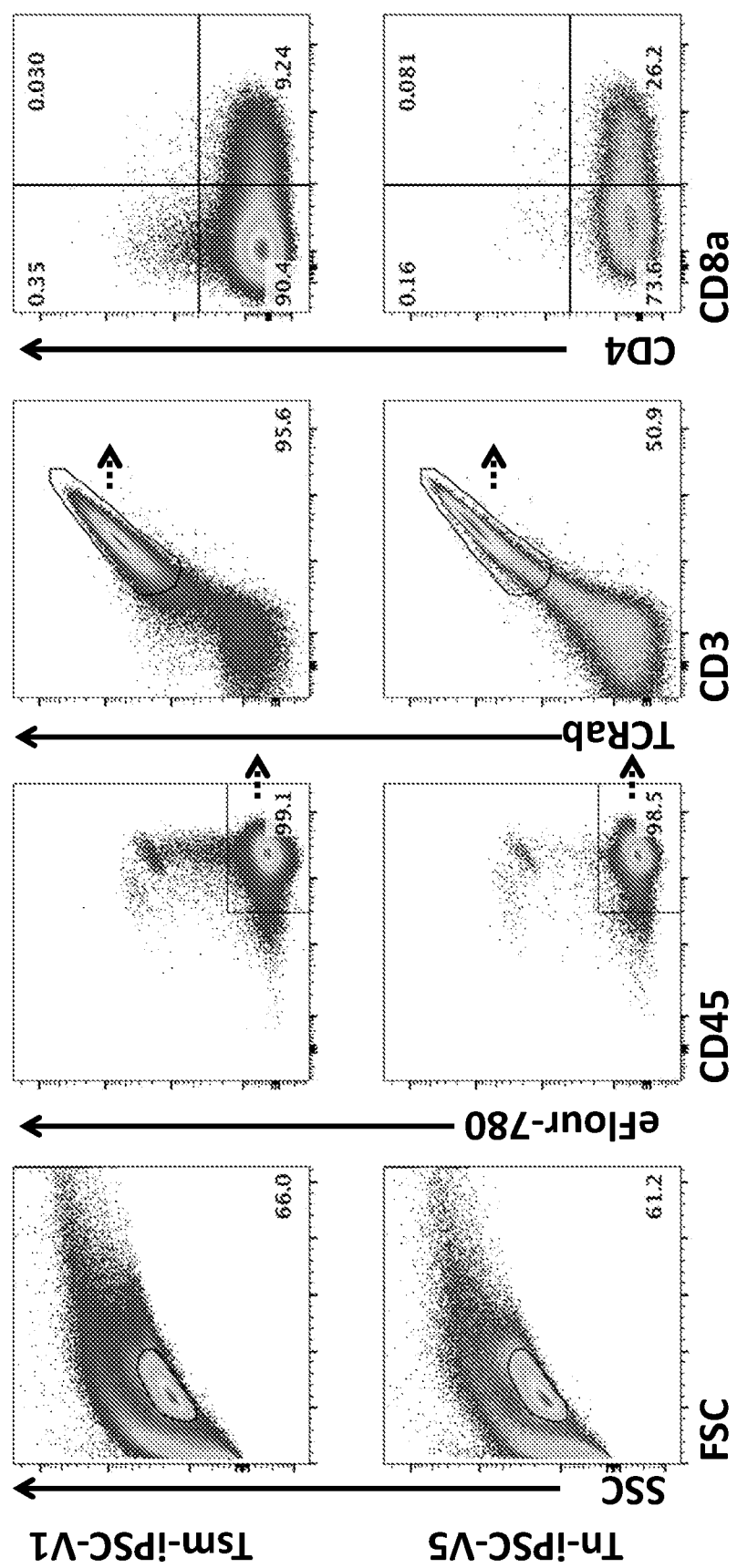

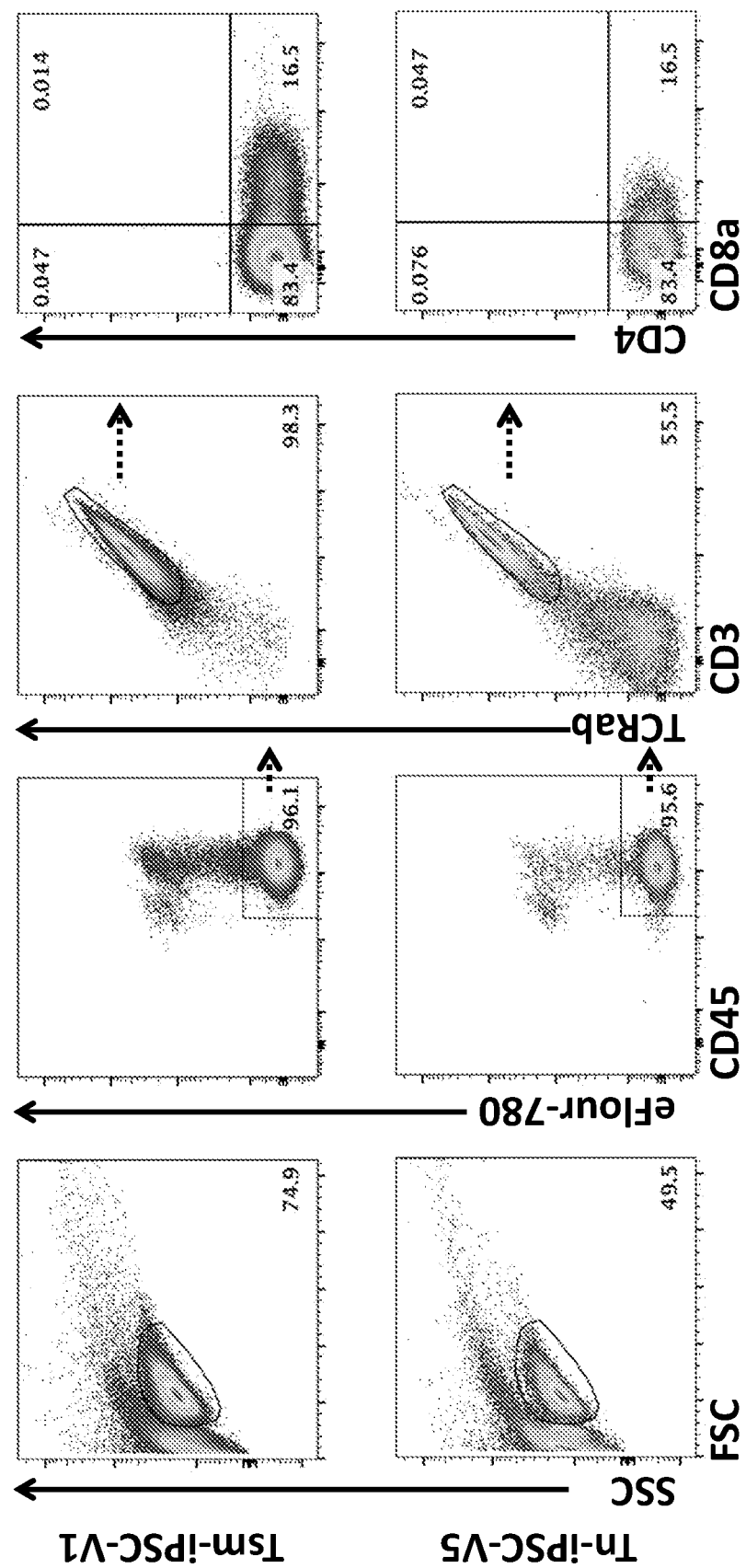

FIGURE 12
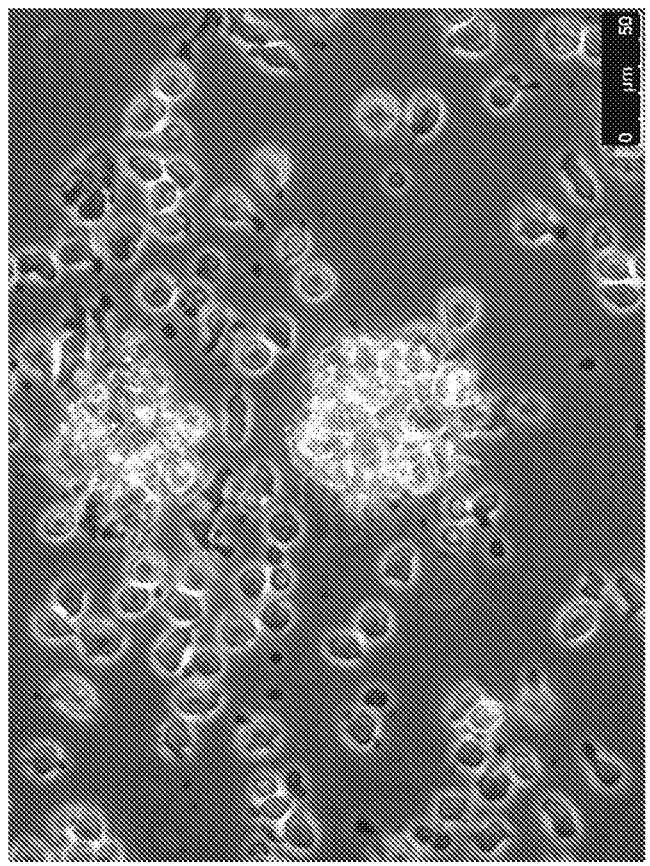
OP9-DL4 + T-Progs/Cells
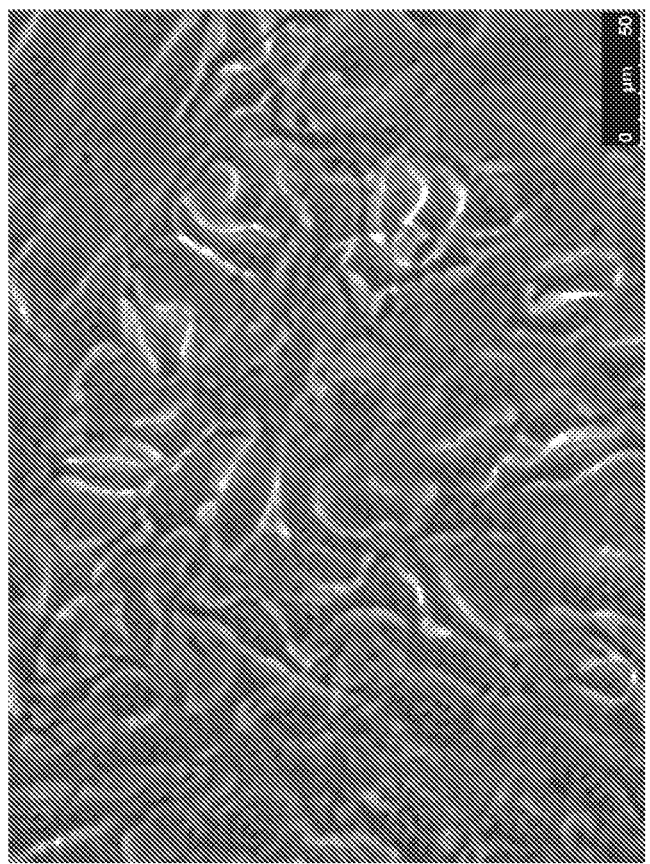
OP9-DL4 Ctrl

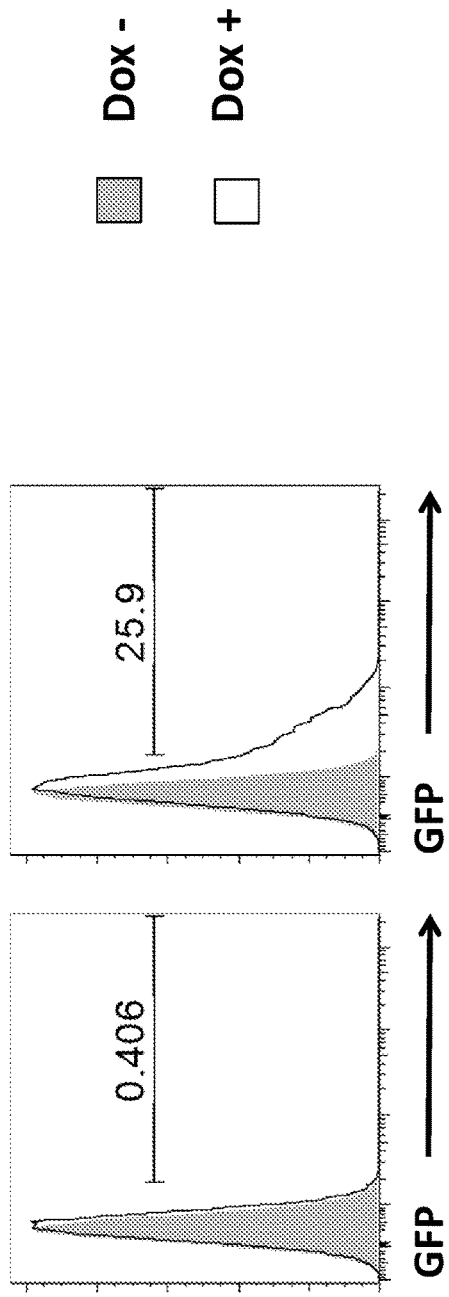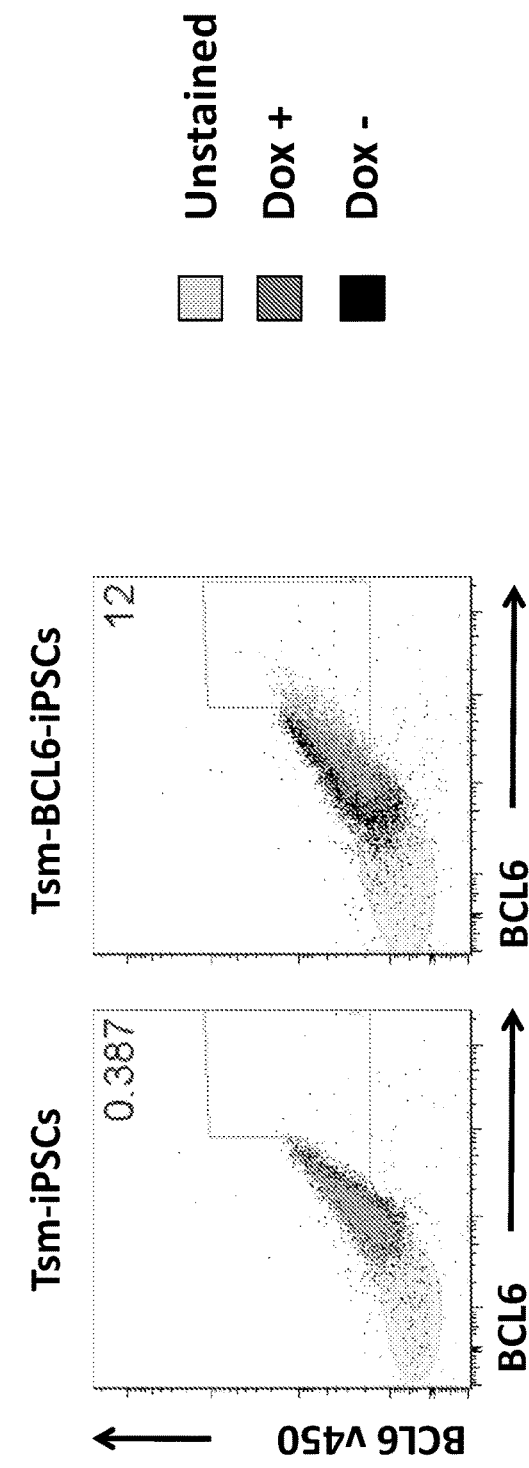
FIGURE 20C
FIGURE 20D

FIGURE 24C
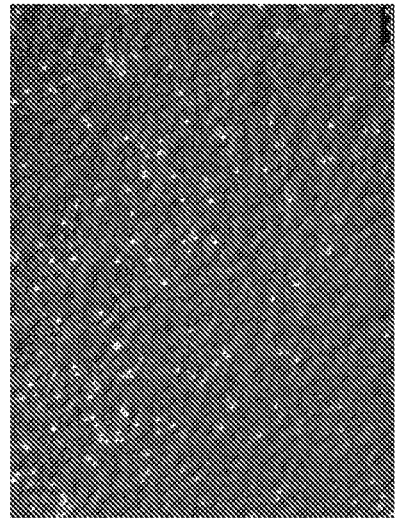
Day 16 CHIR
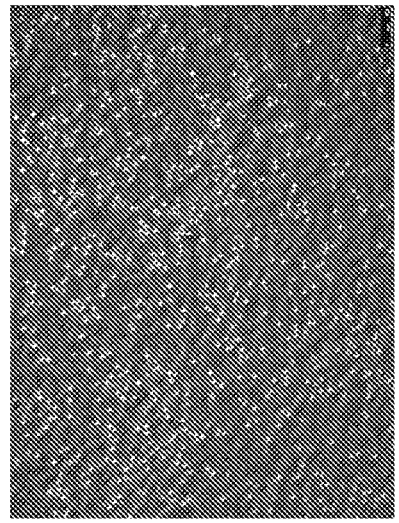
CHIR+SB

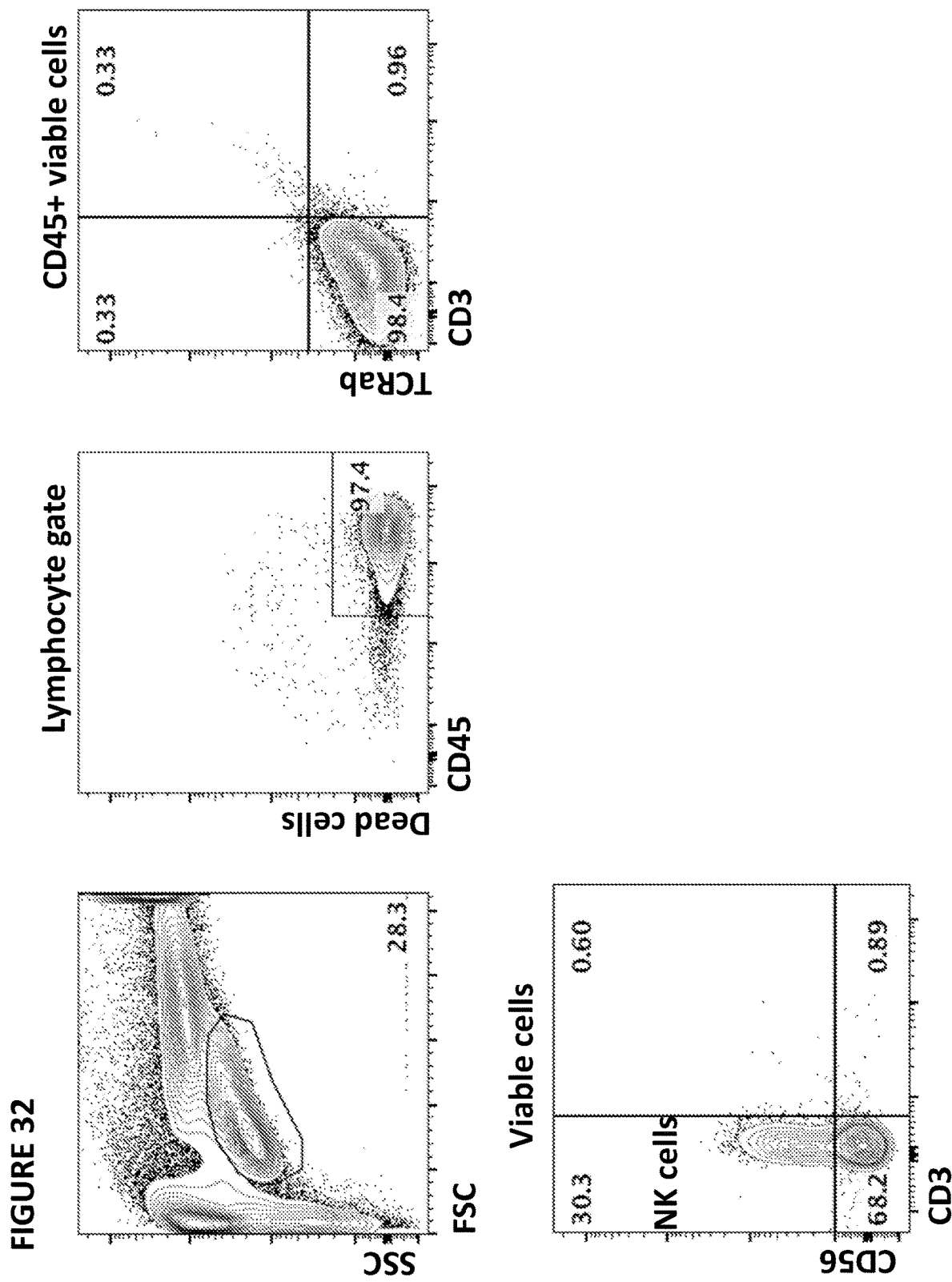

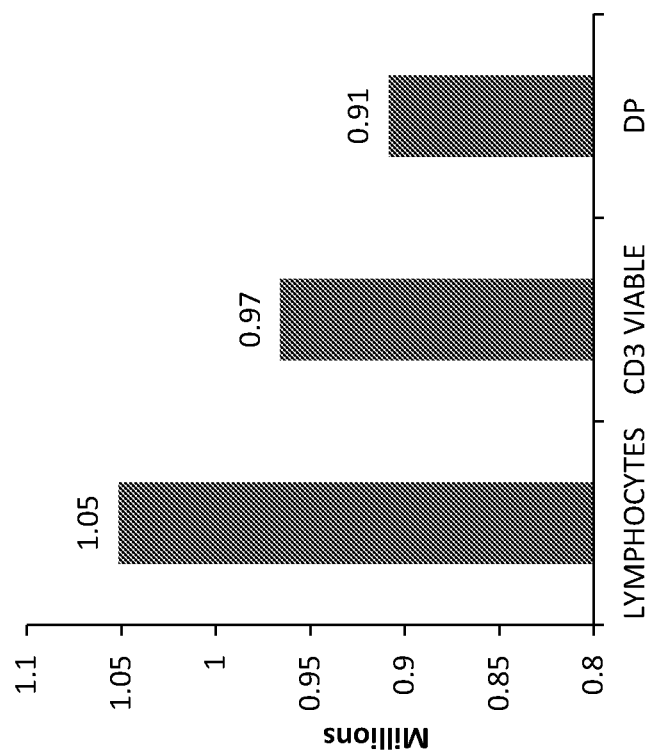
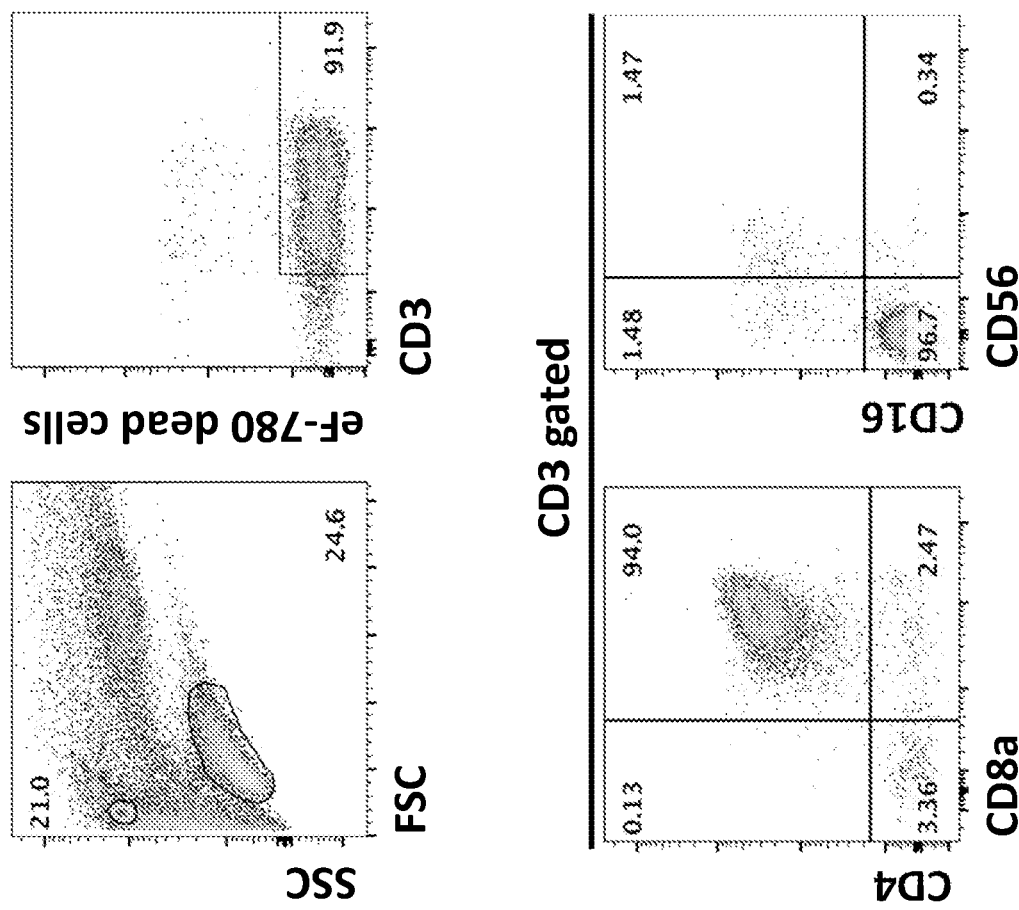

HUMAN T CELL DERIVED FROM T CELL-DERIVED INDUCED PLURIPOTENT STEM CELL AND METHODS OF MAKING AND USING

CONTINUING APPLICATION DATA

This application is the § 371 U.S. National Stage of International Application No. PCT/US2016/065524, filed Dec. 8, 2016, which claims the benefit of U.S. Provisional Application Ser. No. 62/264,455, filed Dec. 8, 2015, the disclosures of which are incorporated by reference herein in their entireties.

GOVERNMENT FUNDING

This invention was made with government support under CA065493 and CA142106 awarded by the National Institutes of Health. The government has certain rights in the invention.

SEQUENCE LISTING

This application contains a Sequence Listing electronically submitted to the United States Patent and Trademark Office via EFS-Web as an ASCII text file entitled "110-05090101_ST25.txt" having a size of 2 kilobytes and created on May 22, 2018. Due to the electronic filing of the Sequence Listing, the electronically submitted Sequence Listing serves as both the paper copy required by 37 CFR § 1.821 (c) and the CRF required by § 1.821 (e). The information contained in the Sequence Listing is incorporated by reference herein and does not go beyond the disclosure in the International Application as filed.

SUMMARY OF THE INVENTION

This disclosure describes an induced pluripotent stem cell (iPSC) derived from a T cell. In some embodiments, the T cell is a human T cell. In some embodiments, the T cell includes a T cell of a T cell subset. For example, the T cell can include a stem memory T cell (Tsm), a stem memory-like cell, a central memory T cell, an effector T cell, a effector/memory T cell, an effector/memory/CD45RA+ T cell, a T exhausted cell, an NKT cell, and/or a naïve T cell. In some embodiments, the T cell preferably includes a stem memory T cell, a central memory T cell, or a naïve T cell.

In some embodiments, the iPSC expresses a chimeric antigen receptor. In some embodiments, the iPSC expresses a T cell receptor.

This disclosure further describes a T cell derived from the iPSC. In some embodiments, the T cell includes at least one of a stem memory T cell, a stem memory-like T cell, a naïve T cell, an effector T cell, an effector/memory T cell, an effector/memory/CD45RA+ T cell, a central memory T cell, an exhausted T cell, and a Natural Killer T cell. In some embodiments, the T cell preferably includes at least a stem memory T cell.

This disclosure further describes a method that includes differentiating an iPSC derived from a T cell of a T cell subset. This disclosure also describes a method that includes differentiating an iPSC derived from a T cell of a T cell subset to a differentiated cell.

In some embodiments, the iPSC is preferably derived from a stem memory T cell, a central memory T cell, or a naïve T cell. In some embodiments, the iPSC comprises a chimeric antigen receptor-expressing iPSC.

In some embodiments, the differentiated cell includes a T cell. In some embodiments, the differentiated cell includes at least one of a stem memory T cell, a stem memory-like T cell, a naïve T cell, an effector T cell, an effector/memory T cell, an effector/memory/CD45RA+ T cell, a central memory T cell, an exhausted T cell, and a Natural Killer T cell. In some embodiments, the differentiated cell preferably includes a stem memory T cell.

In some embodiments, the differentiated cell expresses CD3 and CD8 and at least one of CD45RA, CD62L, CCR7, CD95, and TCRα/β. In some embodiments, the differentiated cell does not express at least one of CD4, CD34, and CD45RO.

In some embodiments, the method includes forming embryoid bodies (EBs).

In some embodiments, the method includes culturing the cell undergoing differentiation in the presence of a Wnt pathway activator and a TGFβ signaling inhibitor.

In some embodiments, the method includes culturing the cell undergoing differentiation in the presence of at least one of basic fibroblast growth factor (bFGF) and bone morphogenetic protein (BMP)-4.

In some embodiments, the method includes culturing the cell undergoing differentiation in the presence of a hematopoietic cytokine. In some embodiments, a hematopoietic cytokine includes at least one of stem cell factor (SCF), vascular endothelial growth factor (VEGF), FMS-like tyrosine kinase 3 ligand (Flt3L), and IL-3.

In some embodiments, the method includes culturing the cell undergoing differentiation on stromal cells expressing a Notch ligand or in media comprising a soluble Notch ligand.

In some embodiments, the method includes culturing the cell undergoing differentiation sequentially with media comprising at least one of basic fibroblast growth factor (bFGF) and bone morphogenetic protein (BMP)-4; media comprising at least one of a Wnt pathway activator and a TGFβ signaling inhibitor; media comprising at least one hematopoietic cytokine; and media comprising at least one of stem cell factor (SCF), IL-7, and FMS-like tyrosine kinase 3 ligand (Flt3L).

In some embodiments, the method includes culturing the cell undergoing differentiation sequentially in media comprising animal-product free medium (APEL) differentiation medium; and media comprising a stromal cell expressing a Notch ligand or media comprising a soluble Notch ligand.

In some embodiments, the method includes enriching a population for CD34+ cells. In some embodiments, the method includes stimulating the cell undergoing differentiation via at least one of CD3 and CD28. In some embodiments, the method further includes stimulating the cell undergoing differentiation in media comprising at least one of stem cell factor (SCF), IL-7, FMS-like tyrosine kinase 3 ligand (Flt3L), IL-15, IL-21, IL-2, a Glycogen synthase kinase 3 inhibitor and an AKT inhibitor.

In some embodiments, the method includes enriching a clonal population comprising the cell undergoing differentiation for cells expressing CD45.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 1(A-H) shows an exemplary embodiment of reprogramming of stem memory T cells (T stem memory or Tsm) or naïve T cell (T naïve or Tn) to pluripotency.

FIG. 2(A-C) shows exemplary directed differentiation schema for generation of T cells from T-iPSC.

FIG. 3(A-B) shows exemplary flow cytometric analysis of indicated markers expression on T-progenitors at day 9 of EB differentiation.

FIG. 5(A-C) shows exemplary flow cytometric analysis of T-iPSC-derived T progenitors/cells at day 16 (9 days EB+7 days OP9-DL4 co-culture).

FIG. 8(A-C) shows exemplary flow cytometric analysis at day 23 (9 days EB+14 days OP9-DL4 co-culture) of viability and CD45, CD5, CD4, CD8, and TCR expression. FIG. 8A. Tsm- and Tn-iPSC-derived EBs were dissociated at day 9 of differentiation, CD34$^+$ cells were enriched using CD34 EASYSEP and co-cultured with OP9-DL4 stromal cells for 14 additional days. Desired lymphocyte populations were gated stringently, viable CD45 positive cells were analyzed by flow cytometric analysis for indicated markers on day 23. Dashed arrows indicate sub-gating strategies. OP9-DL4 stromal cells were freshly plated every 4 to 5 days.

FIG. 9(A-C) shows exemplary flow cytometric analysis at day 30 (9 days EB+21 days OP9-DL4 co-culture) of viability and CD45, CD5, CD4, CD8a, and TCR expression. FIG. 9A. Tsm- and Tn-iPSC-derived EBs were dissociated at day 9 of differentiation, CD34$^+$ cells were enriched using CD34 EASYSEP and co-cultured with OP9-DL4 stromal cells for 21 additional days. Desired lymphocyte populations were gated stringently; viable CD45 positive cells were analyzed by flow cytometric analysis for indicated markers on day 30. Dashed arrows indicate sub-gating strategies. OP9-DL4 stromal cells were freshly plated every 4 to 5 days.

FIG. 10(A-C) shows exemplary flow cytometric analysis at day 37 (9 days EB+28 days OP9-DL4 co-culture).

FIG. 12 shows exemplary cytotoxic function of in vitro-differentiated T cells at day 17. T-iPSC-derived EBs were dissociated at day 9 of differentiation, CD34$^+$ cells were enriched using CD34 EASYSEP. Then 7.5×10$^5$ CD34$^+$ hematopoietic progenitors were co-cultured with OP9-DL4 stromal cells for 7 additional days. At day 16 (9+7), cells were dissociated and purified using lymphocyte lineage marker CD45, then 1.2×10$^6$ CD45 T cells were seeded on freshly coated 2.5×10$^4$ OP9-DL4 cells. Phase contrast images were taken 24 hours later at day 17 and show destruction of stromal cells by T progenitors. Scale bars are indicated in bottom right corners.

FIG. 14(A-B) shows exemplary images of Tsm-iPSC-V1 derived cytotoxic T cells and Tn-iPSC-V5 derived cytotoxic T cells.

FIG. 15(A-C) shows exemplary flow cytometric analysis of Granzymes A and B, Perforin, CD56, CD95, and CD69 expression in or on cytotoxic T cells.

FIG. 19 shows exemplary results of deletion of a regulator of T cell differentiation, the PRDM1 gene, which encodes PR domain zinc finger protein 1 (PRDM1 protein, also referred to herein as BLIMP-1), a repressor of beta-interferon, and a regulator of hematopoietic stem cells.

FIG. 20C shows GFP expression in Tsm-iPSCs or Tsm-BCL6-iPSCs produced from WT Tsm-iPSC transfected with the BCL6 construct showed in FIG. 20A. Stable colonies of transfected Tsm-iPSCs were selected with puromycine antibiotic selection pressure. BCL6 and GFP expression was induced with doxycycline and assayed 48 hours post-dox induction. FIG. 20D. Nuclear BCL6 protein expression was analyzed 48 hours post-dox induction in the indicated cell types.

FIG. 24(A-C) shows exemplary results of culture with CHIR99021 versus CHIR99021 and SB431542, as measured at day 16. Tsm-iPSCs were subjected to 9 days EB differentiation followed by 7 additional days of OP9-DL4 co-culture. During day 1.75 to day 3 of EB differentiation, cultures were treated with CHIR99021 or CHIR99021 and SB431542. At day 16, FIG. 24C shows phase contrast image of T (progenitor) cells treated either with CHIR99021 or CHIR99021 and SB431542 growing on OP9-DL4 stromal cells.

FIG. 26(A-B) shows exemplary results of culture with CHIR99021 versus CHIR99021 and SB431542, as measured at day 23. Tsm-iPSCs were subjected to 9 days EB differentiation followed by 14 additional days of OP9-DL4 co-culture. During day 1.75 to day 3 of EB differentiation, cultures were treated with CHIR99021 or CHIR99021 and SB431542.

FIG. 32 shows analysis of CS-1-iPSC derived T progenitors at day (9+15) 24. CS-1-iPSC derived CD34$^+$ cells were enriched and co-cultured on OP9-DL4 for 15 days as described in STEP II of Example 9 (total day 9+15=24 days) followed by flow analysis of indicated markers.

FIG. 33(A-D) shows that modulation of Notch signaling allows proper development of DP-T cells. FIG. 33A. Tsm-iPSCs derived CD34$^+$ cells were enriched and co-cultured on OP9-DL4 for 28 days as described in STEP II of Example 9 (total day 9+28=37 days) followed by flow analysis of indicated markers. FIG. 33B. Absolute cell numbers for indicated groups are depicted. At day 37 of Tsm-iPSCs differentiation, ~86% of viable CD3+ cells are DP-T cells.

DETAILED DESCRIPTION

Figure 1A:
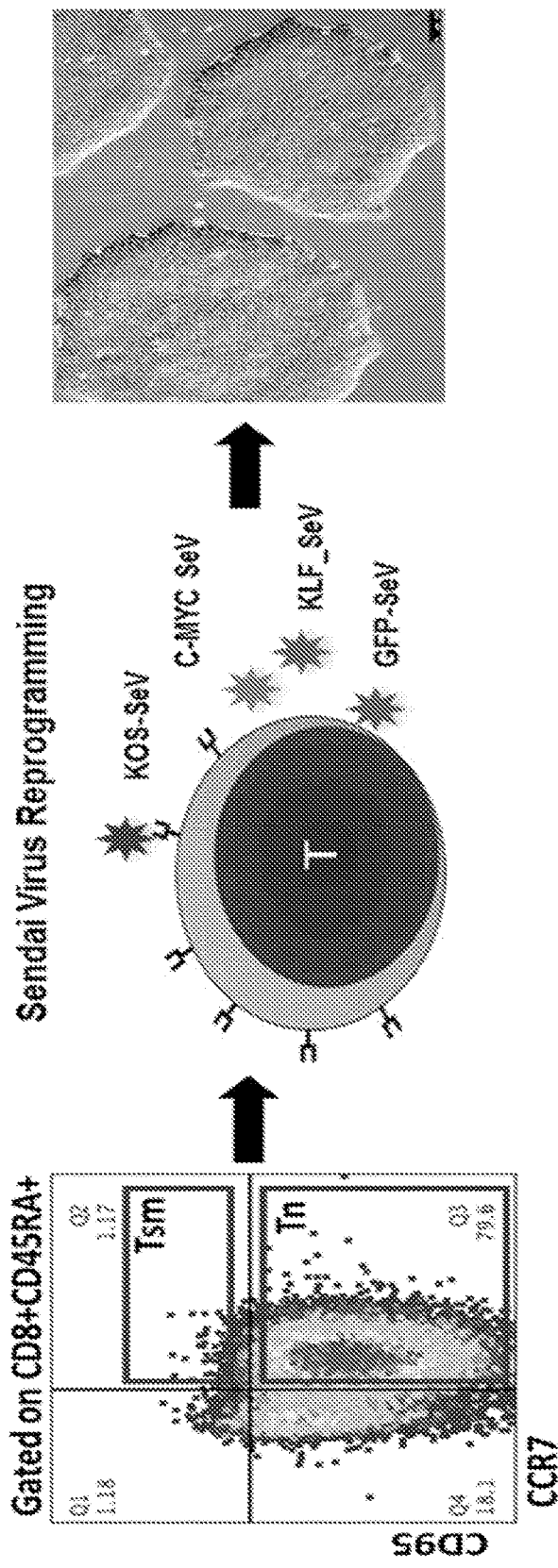
FIG. 1A. Schematic of naïve T cell (T naïve or Tn) and T stem memory cell isolation and Sendai virus-based reprogramming strategy to an iPSC (as shown in the right panel).
Figure 1D:
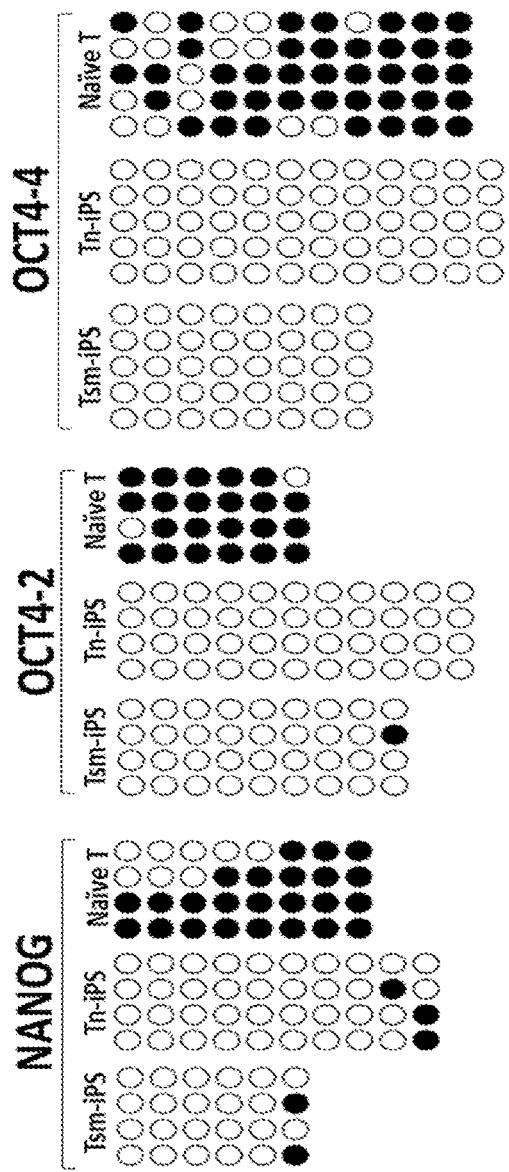
FIG. 1D. Bisulfite sequencing analysis demonstrating CpG hypomethylation at Nanog and Oct4 promoter regions in Tsm and Tn-iPSC.
Figure 1B:
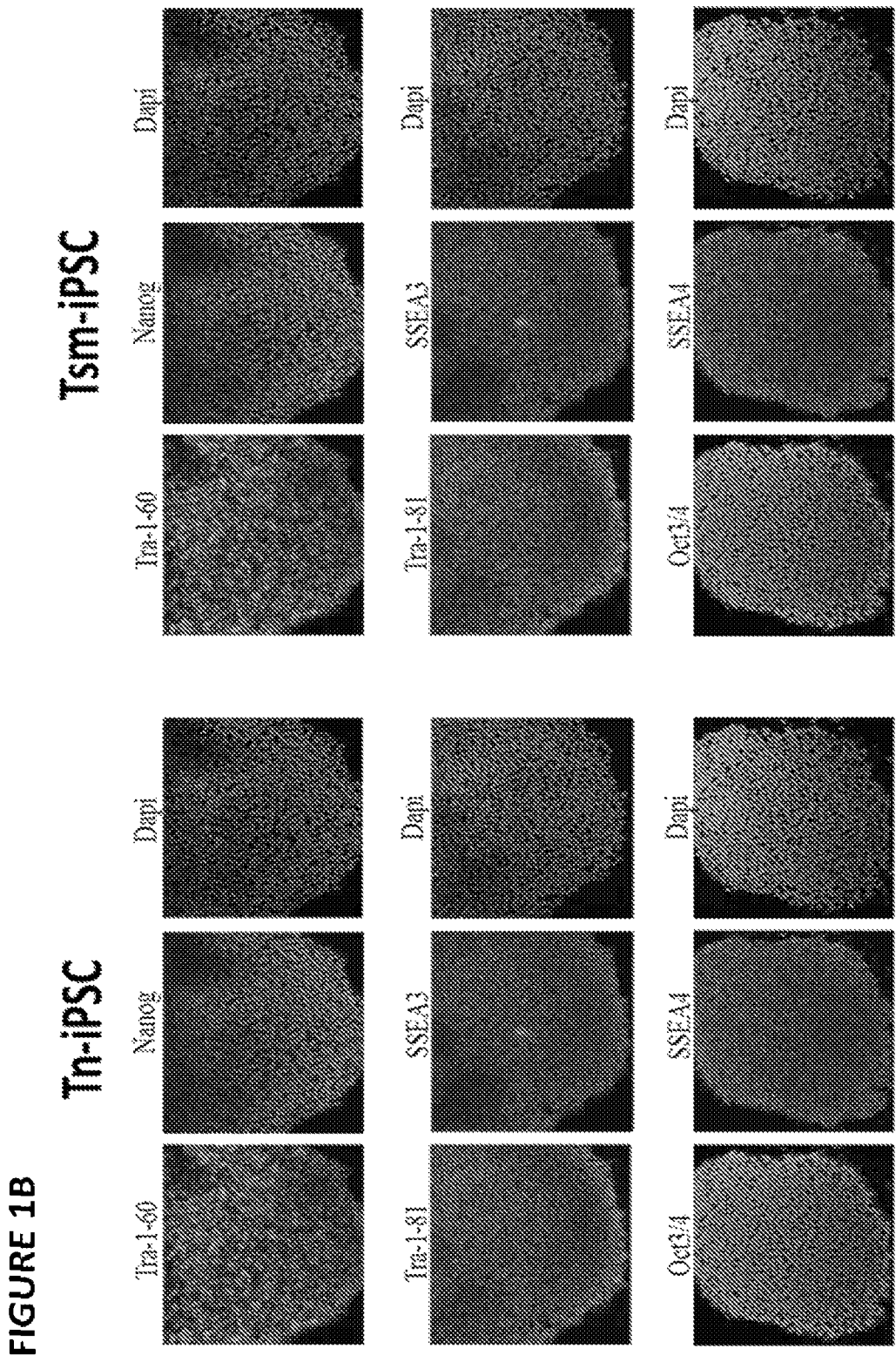
FIG. 1B. Live-cell immunofluorescence staining for pluripotency markers TRA-1-60, NANOG, TRA-1-81, SSEA3, OCT-3/4, and SSEA4 in stem memory T cell-derived induced pluripotent stem cells (Tsm-iPSC) and naïve T cell-derived induced pluripotent stem cells (Tn-iPSC) colonies.
Figure 1H:
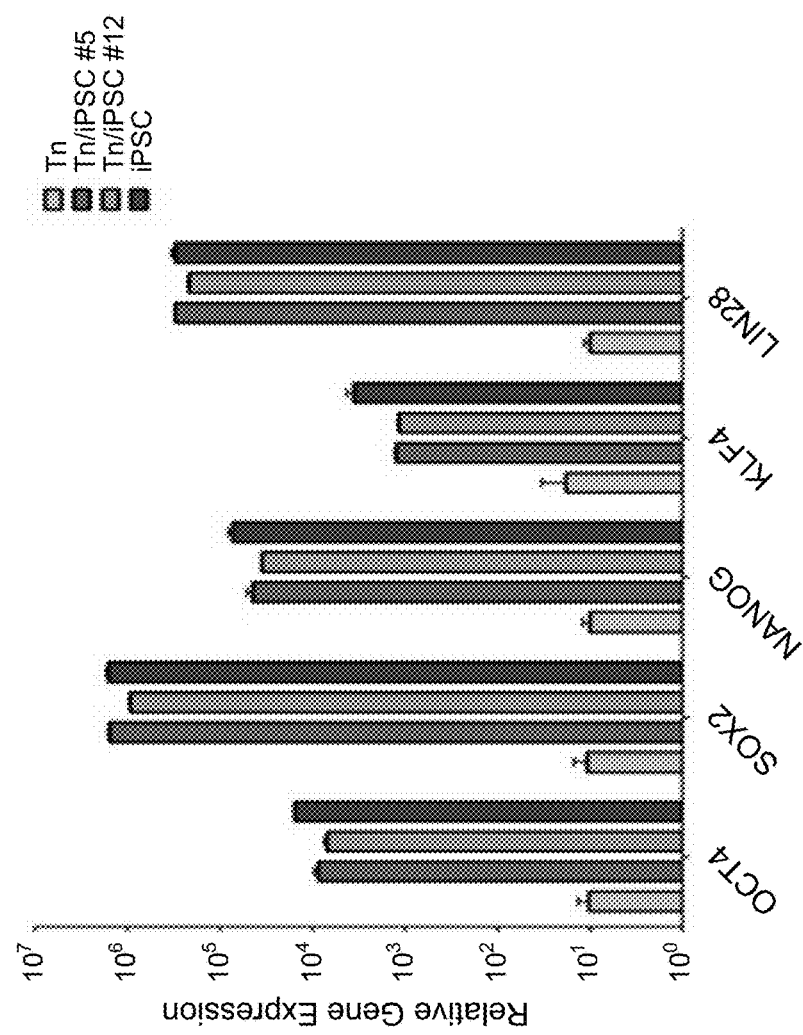
FIG. 1H. Teratoma formation assay shows Tn- and Tsm-iPSC formed all three germ layers Ec (ectoderm), M (mesoderm) and En (endoderm) labeled in the images.

This disclosure provides methods and compositions for improving the safety and efficacy of genetically modified T cells for cancer therapy. For example, this disclosure provides methods to reprogram T cells, including, a T cell of a T cell subset, into induced pluripotent stem cells (iPSCs); methods to differentiate iPSCs into T cells; methods to engineer chimeric antigen receptor (CAR)-expressing iPSCs and CAR-expressing T cells; and methods to engineer T cell receptor (TCR)-expressing iPSCs and TCR-expressing cells. A T cell subset can include, for example, a stem memory T cell (also referred to herein as Tsm or T stem memory cell), a stem memory-like T cell (also referred to herein as a T stem memory-like cell), a naïve T cell (also referred to herein as Tn or T naïve cell), an effector T cell (also referred to herein as a T effector cell), an effector/memory T cell (also referred to herein as a T effector/memory cell), an effector/memory/CD45RA+ T cell (also referred to herein as a T effector/memory/CD45RA+ cell), a central memory T cell (also referred to herein as a T central memory cell), an exhausted T cell (also referred to herein as a T exhausted cell), and/or a Natural Killer T cell (also referred to herein as an NKT cell). In some embodiments, the T cell of the T cell subset preferably includes a T stem memory cell.

T stem memory cells can self-renew and differentiate into a broad array of T effector and memory cells to combat foreign antigens (e.g., tumor or virus antigens). T stem memory cells share a partially conserved transcriptional profile with hematopoietic stem cells (HSCs) and, similar to stem cells, they can undergo asymmetric division and activate telomerase to maintain telomere length and replicative potential. Several signaling pathways regulating stem cell self-renewal are active in T cells and promote memory and limit T effector differentiation. T stem memory cells outcompete T naïve and central memory T cells in NOD-SCID-IL2Rgc (NSG) mice. Although $CD8^+CD62L^+$ T naïve and central memory T cells retain immunocompetence upon serial transfer for 3 generations, the immunocompetence of T stem memory cells has not been formally tested nor are the conditions conducive to their generation known.

Nevertheless, T stem memory cells are expected to be particularly effective for therapeutic treatments in some situations because 1) CAR-T cell persistence and remission duration correlate with infused T stem memory cell frequencies in mice and humans; 2) T stem memory cells have superior anti-tumor effects; and 3) higher remission rates with CAR-T cells have been observed in children (who likely produce more T stem memory cells) than older or chemotherapy treated patients.

Expansion of T stem memory cells from peripheral blood successively skews T stem memory cells away from a T stem memory phenotype with each cell division, a disadvantage because T stem memory cell frequency is already low and/or because high T stem memory cell numbers are needed for multiple treatments for tumor and pathogen immune surveillance and treatment of tumor cells and pathogens. Chronically stimulated and ex vivo expanded T cells differentiate into T effectors that can terminally differentiate or become exhausted, resulting in loss of cytokine production, proliferation, and cytolysis. T cell differentiation is associated with profound, global changes in gene expression.

As described herein, human T cells can be reprogrammed into iPSCs which can, in some embodiments, be modified to express a CAR and re-differentiated into mature T cells. iPSCs may serve as a self-renewable T cell source for repetitive T cell infusions. Human T stem memory cells generated from iPSCs may provide a virtually limitless source of long-lasting T stem memory CAR T cells for adoptive therapy in chemotherapy treated patients with low T stem memory cell frequencies. As described herein, generation of an iPSC from a T stem memory cell can retain the epigenetic landscape and developmental plasticity of a T stem memory cell in a T cell, including a CAR-T cell, differentiated from the iPSC. Similar principles hold true for Teffector cells, Teffector/memory cells, Teffector/memory/CD45RA+ cells, and Tcentral memory cells.

Derivation of an iPSC from a T Cell

This disclosure describes an induced pluripotent stem cell (iPSC) derived from a T cell, including, in some embodiments from a T cell of a T cell subset. In some embodiments, the T cell subset preferably includes a T stem memory cell, a T effector cell, a T effector/memory cell, a T central memory cell, an NKT cell, and/or a naïve T cell. This disclosure further describes methods to obtain an iPSC derived from a T cell. In some embodiments, the iPSC is preferably derived from a T cell of a T cell subset. In some embodiments, the derivation is called "reprogramming." The T cell to be reprogrammed can be from a mammalian source including, for example, a human or a mouse. While reprogramming of murine and human T cells into iPSCs has been reported, higher efficiency reprogramming and the means for deriving more iPSCs from the source cells are still needed.

In mice and humans, $CD4^+$ and $CD8^+$ T cells acquire a long lasting memory phenotype upon encounter of antigenic stimuli such as a pathogen or a tumor cell. Upon stimulation, naïve T cells can differentiate to T stem cell memory, T central memory, T effector, Teffector/memory, or Teffector/memory CD45RA+ cells. T naïve and T stem cell memory cells exhibit the highest proliferative capacity and share phenotypic and functional characteristics with hematopoietic stem cells including the capacity to self-renew and differentiate into multiple cell types such as T central memory and T effector cell subtypes. For example, $CD8^+$ clones isolated from central memory T cells but not from $CD8^+$ effector cells persist long-term in vivo after adoptive T cell transfer in a nonhuman primate model, indicating the importance of specific T cell subset functions for effective adoptive immunotherapy.

In some embodiments, and as further described herein, iPSC generated from a Tn, a Tsm, and/or a T central memory cell can provide a virtually limitless source of long-lasting Tsm cells for adoptive therapy in chemotherapy treated patients with low Tsm frequencies. In some embodiments, and as further described herein, the Tsm cell used for adoptive therapy can be a CAR-Tsm cell.

Without wishing to be bound by theory, it is believed that deriving an iPSC from a Tn, a T central memory cell, or a Tsm cell can retain the epigenetic landscape and developmental plasticity of the T cells in the iPSC and, in some embodiment, in a T cell differentiated from the iPSC. But Tsm cells mostly reside in the lymphoid tissues and very few of them are enter into peripheral blood stream (about 0.2-0.3%), making it challenging to obtain enough cells for reprogramming.

In some embodiments, the iPSC is preferably derived from a T cell of a T cell subset. For example, a T cell-derived iPSC (T-iPSC) can be derived from a naïve T (also referred to herein as a T naïve or a Tn) cell. A "Tn-iPSC" as used herein refers to an iPSC derived from a naïve T cell. In some embodiments, a T-iPSC can be derived from a stem memory T (T stem memory) cell. A "Tsm-iPSC" as used herein refers to an iPSC derived from a T stem memory cell. In contrast, a "CS-1-iPSC" as used herein refers to an iPSC derived from a human skin fibroblast cell.

In some embodiments, a T cell, including a T cell of a T cell subset, can be separated from whole blood and/or a buffy coat using flow cytometry. In some embodiments, the T cell is a human cell. In some embodiments, the T cell can be derived from a subject in need of treatment. In some embodiments, the T cell is $CD3^+$ and/or $CD8^+$. In some embodiments, the T cell can further express at least one of CD45RA, CD62L, CD95, TCRαβ, CD4, CCR7, IL7Rα, CD27, and CD28. In some embodiments, a T naïve cell is defined as a cell that is CD8⁺CD62L⁺CD45RA⁺CCR7⁺CD95⁻CD45RO⁻. In some embodiments, a T stem memory cell is defined as a cell that is CD8⁺CD62L⁺CD45RA⁺CCR7⁺CD95⁺CD45RO⁻. In some embodiments, a T naïve cell and/or a T stem memory cell can also express CD27, CD28 and/or IL7Rα. In some embodiments, the T cell is a CD4⁺. In some embodiments, the T cell is a member of a T cell subset that has one or more features corresponding to a CD8⁺ T cell subset.

An iPSC can be derived from a T cell, including a T cell of a T cell subset, according to the methods described in, for example, Brown et al. *PloS One.* 2010; 5(6):e11373; Seki et al. *Current protocols in stem cell biology.* 2011; Chapter 4:Unit4A 3; Seki et al. *Cell Stem Cell.* 2010; 7(1):11-4; Takahashi et al. *Cell.* 2006; 126(4):663-76; Fusaki et al. *Proceedings of the Japan Academy Series B, Physical and biological sciences.* 2009; 85(8):348-62; and/or Park et al. *Nature.* 2008; 451(7175):141-6. In contrast to these previously described methods, however, an iPSC is preferably derived from a T cell of a T cell subset. In some embodiments, the T cell subset preferably includes a T naïve cell, a central memory T cell, and/or a T stem memory cell.

In some embodiments, a T cell, including a T cell of a T cell subset, may be cultured with anti-CD3/28 mAb beads; IL-2; IL-7; IL-15; IL-21; a Glycogen synthase kinase (GSK) 3 inhibitor (e.g., TWS119, CHIR99021, CHIR-98014, LY2090314, BIO, IM-12, 3F8, A 1070722, CHIR 99021 trihydrochloride, L803-mts, SB 216763, SB 415286, and/or TC-G 24); and/or an AKT signaling inhibitor (e.g., MK-2206 2HCl, GSK690693, Ipatasertib, AZD5363, Afuresertib, and/or Perifosine (KRX-0401)). In some embodiments, the cytokines may be used at a concentration of 1 nanograms per milliliter (ng/mL) to 1 microgram per milliliter (µg/mL), inclusive. In some embodiments, the AKT inhibitors may be used at a concentration of 1 nanomolar (nM) to 10 micromolar (µM), inclusive.

In some embodiments, an iPSC can be derived from a T cell, including a T cell of a T cell subset, by inducing expression of one or more of the Yamanaka factors (Oct3/4, Sox2, Klf4, c-Myc), genes that are highly expressed in embryonic stem cells (FIG. 1) Expression of these and/or other pluripotency-associated genes may be effected by an method known to a skilled artisan including, for example, introduction by retrovirus, lentivirus, DNA minicircles, and/or non-integrating Sendai virus (ss-RNA virus).

In some embodiments, a T cell, including a T cell of a T cell subset, can be pre-stimulated before being subjected to reprogramming. For example, T naïve and T stem memory cells can be sorted from peripheral blood and stimulated with anti-CD3/28 beads in presence of IL-2, IL-7, and/or IL-15 for 48 hours before being subjected to reprogramming with Sendai virus.

In some embodiments, sorted CD8⁺ T naïve cells can be cultured after isolation by flow cytometry with anti-CD3/28 mAb beads (3:1 to 1:1 ratio of beads:cells) and IL-2 (50 Units per milliliter (U/mL)) (see, e.g., Gattinoni et al, *Nature Medicine.* 2011; 17(10):1290-7).

Figure 18:
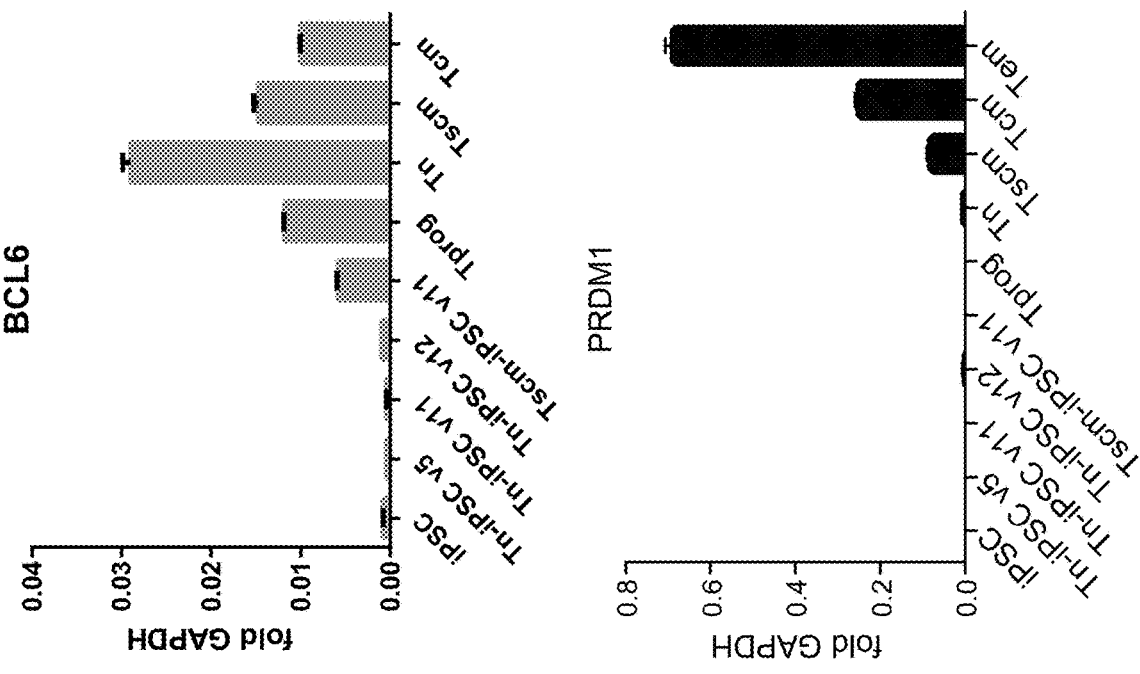
FIG. 18 shows exemplary fold increase in mRNA expression of BCL6 and PRDMJ, as measured by RT-qPCR, normalized to GAPDH.
Figure 17A:
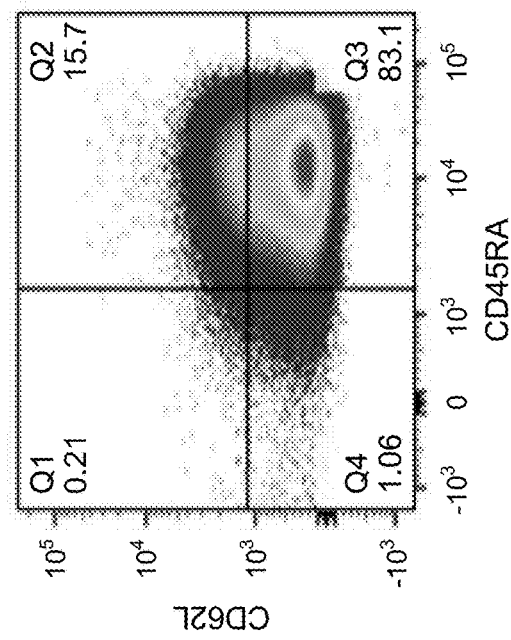
FIG. 17(A-B) shows exemplary flow analysis of Tsm-like cells (Q2) derived from sorted T naïve (Tn) CD8 T cells after stimulation without (FIG. 17A) or with (FIG. 17B) TWS119 (a Glycogen synthase kinase 3 inhibitor) for 8 days. Y-axis, CD62L; x-axis CD45RA. CD95$^+$: 27 percent (%) without TWS119 treatment and 85% with TWS119 treatment (not shown). Tsm-like cells were derived from T naïve cells sorted from human peripheral blood, then stimulated with anti CD3/CD28 and then cultured for 8 days with or without TWS119 treatment.
Figure 17B:
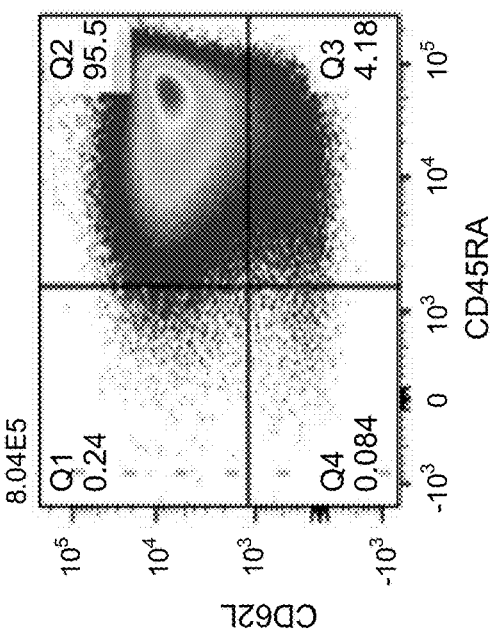

After two days in culture, IL-7 (5 ng/mL), IL-15 (5 ng/mL)±TWS119 (5 µM) can be added. After two days of culture, T stem memory-like (CD8/45RA/62L/95/CCR7⁺) cells are present in high frequency (70%) after treatment with TWS119 and at a low frequency (<5%) after no treatment with TWS119 (FIG. 17). Although TWS119 significantly decreases proliferation of Tn- and Tsm-like cells, as measured by CFSE dilution, by day 8 of culture with IL-7, IL-15, and TWS119, T stem memory-like cells increased >3-fold over input Tn cells and Tn cells without TWS119. Each cell type was analyzed by qRT-PCR: BCL6, Tn>Tsm>Tcm; PRDMJ, Tcm>Tsm>Tn (reciprocal to BCL6) (FIG. 18). Rag1/2 expression in T progenitors was high in developing thymocytes and non-detectable in mature Tn cells and Tn-iPSCs. Whereas no TCR Vb rearrangements were seen in iPSCs from non-T cell sources, both Tn-iPSC colonies had clonal TCR Vb rearrangements, as measured by fluorescent-labeled PCR and capillary electrophoresis.

Reprogramming of human T cells can include introduction of Yamanaka factors (c-MYC, KLF4, SOX2, OCT4) (Takahashi et al. *Cell.* 2006; 126 (4): 663-76). Yamanaka factors can be delivered by any suitable means including, for example, retrovirus, lentivirus, DNA minicircles, and/or non-integrating Sendai virus (ss-RNA virus) (Fusaki et al. *Proceedings of the Japan Academy Series B, Physical and biological sciences.* 2009; 85 (8): 348-62). In some embodiments, Sendai virus has been found to be the most consistent, efficient delivery method and to permit transgene free colonies.

Figure 1C:
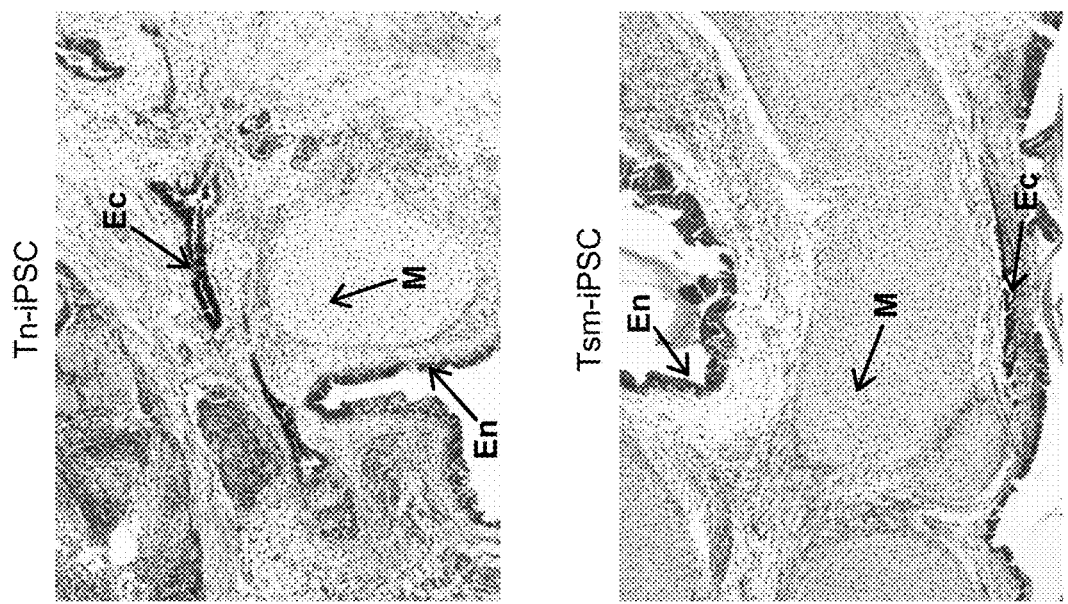
FIG. 1C. Quantitative RT-PCR based analysis of pluripotency gene expression in T-induced pluripotent stem cell (iPSC) clones.
Figure 1E:
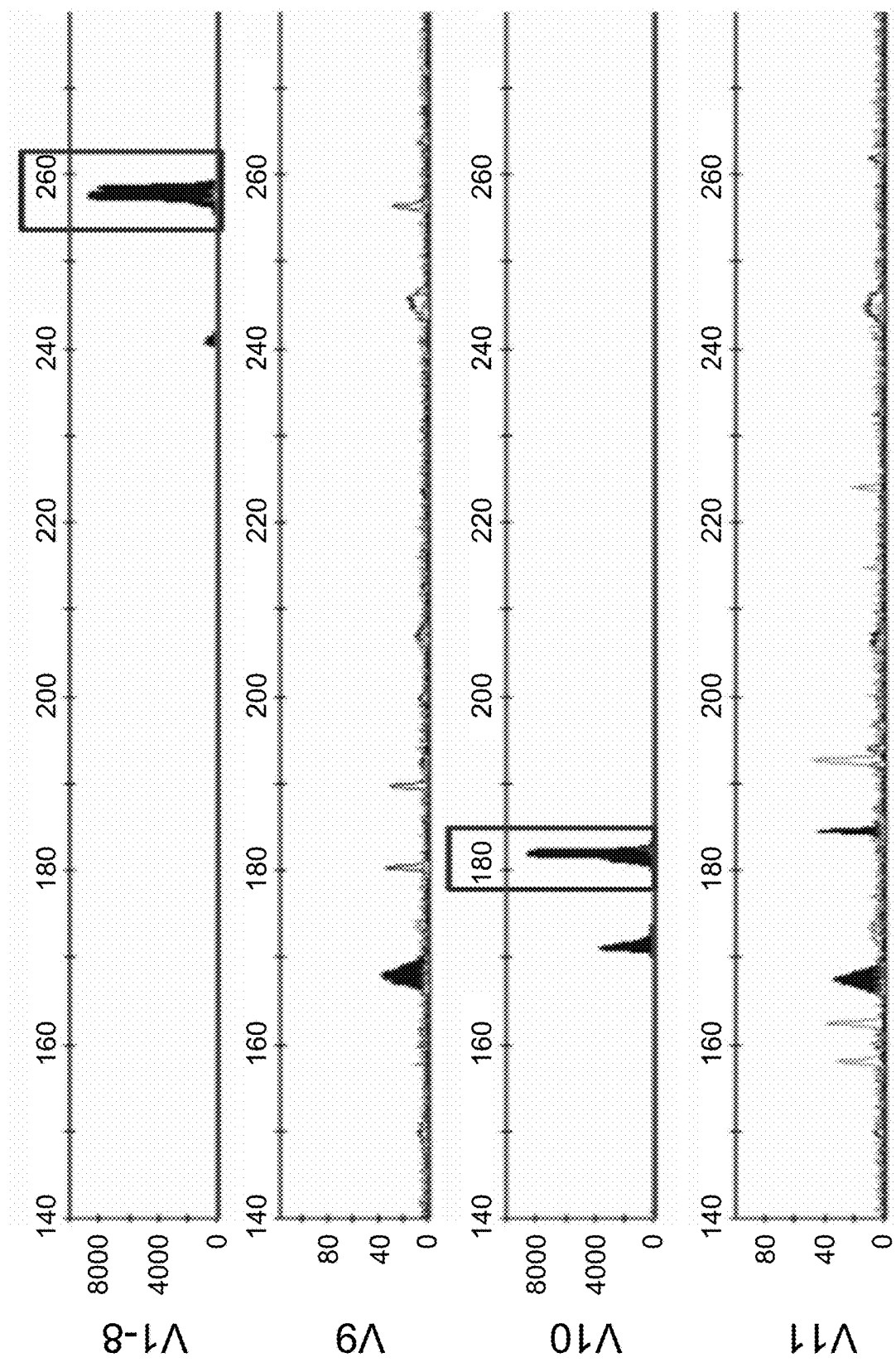
FIG. 1E. T-cell receptor rearrangement analysis demonstrating the presence of unique, clonal T cell receptor (TCR) rearrangements in Tn-iPSC clones.
Figure 1F:
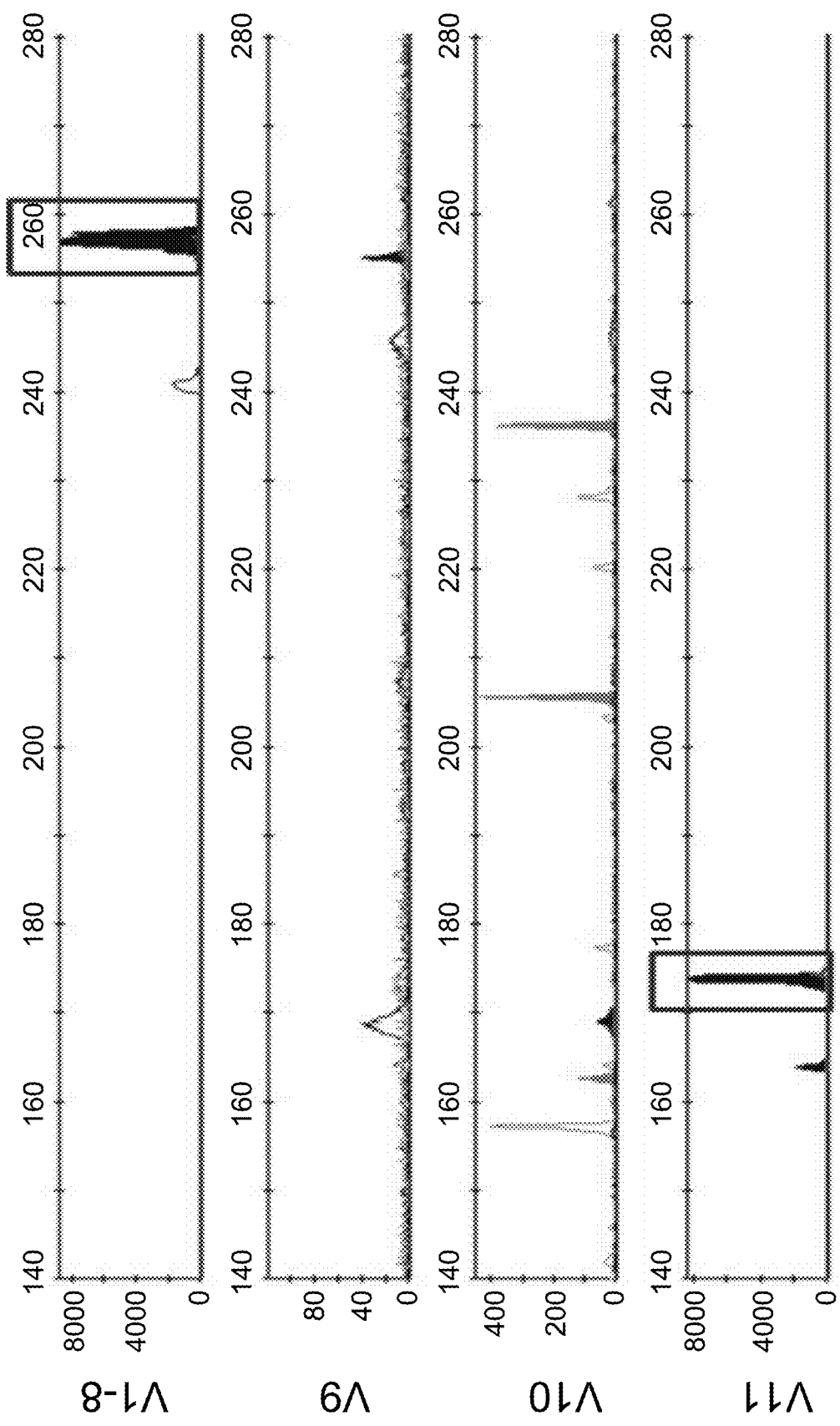
FIG. 1F. T-cell receptor rearrangement analysis demonstrating the presence of unique, clonal T cell receptor (TCR) rearrangements in Tsm-iPSC clones.
Figure 1G:
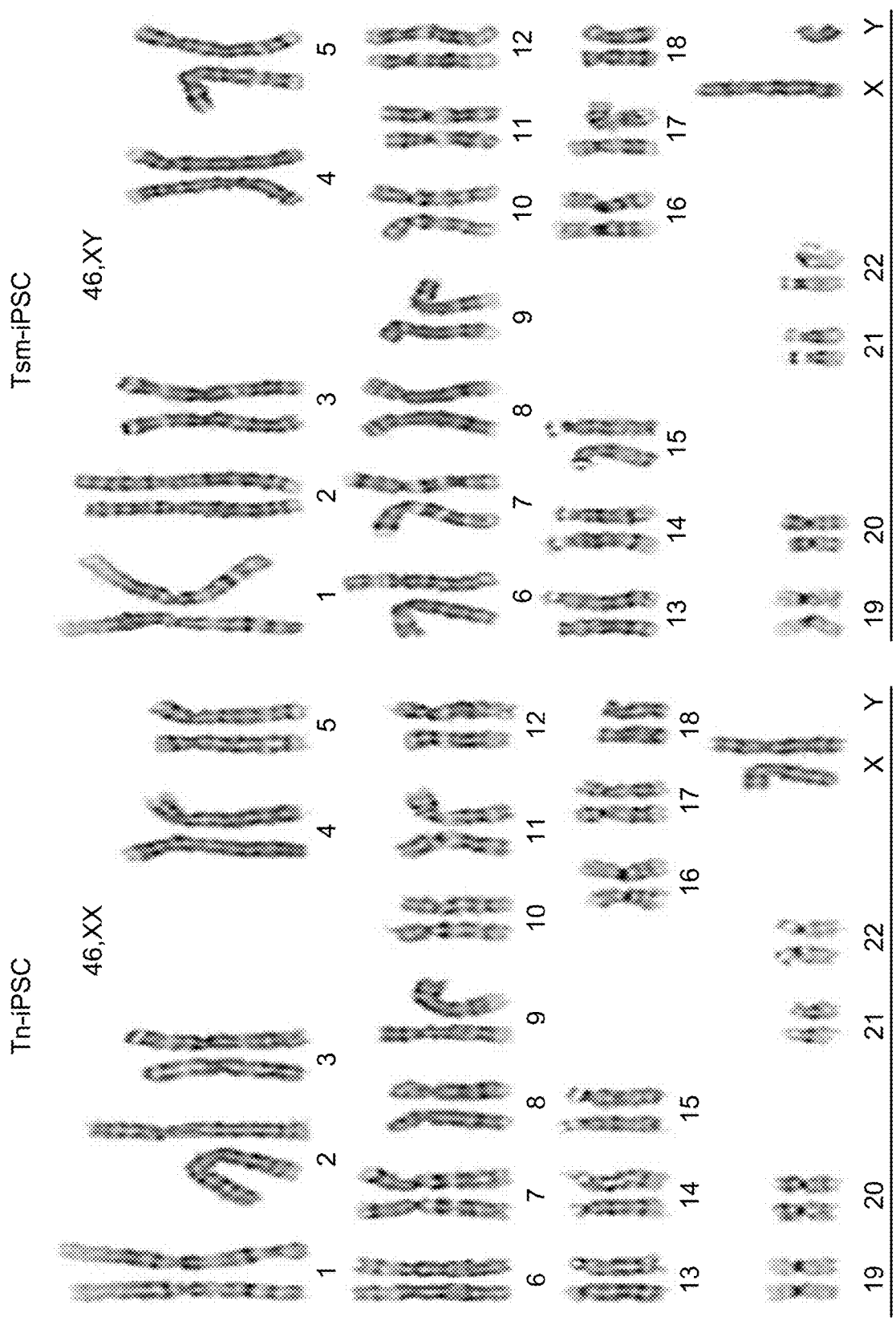
FIG. 1G. Chromosome spread demonstrating that Tsm- and Tn-iPSC possess a normal karyotype.

Flow sorted human CD8 T naïve (CD62L⁺CD45RA⁺) cells were cultured with anti-CD3/28 mAb beads+IL-2, IL-15, IL-7 for 48 hours, then exposed to 5 Sendai viruses [c-MYC; SOX2, OCT4; KLF4; GFP] for 6 d then placed on murine embryonic fibroblast cells (MEFs) followed by iPSC medium (3 d). Compared to T naïve cells, qRT-PCR for OCT4; SOX2; NANOG; KLF4; LIN28 showed $10^3$-$10^5$ higher levels of each transcript in Tn-iPSC compared to T naïve cells (FIG. 1C). The level of gene expression of the pluripotency genes OCT4, SOX2, NANOG, KLF4, and LIN29 was indistinguishable from the levels of expression in previously characterized fibroblast derived iPSC-line CS-1. Bisulfite sequencing, performed as described by Darst et al. 2010. Bisulfite Sequencing of DNA. *Current Protocols in Molecular Biology.* 91:7.9:7.9.1-7.9.17, indicated full demethylation of Oct4-2, Oct4-4 and nanog promoters (FIG. 1D) in CpG regions in Tn-iPSC and Tsm-iPSC clones. Teratoma formation (Tolar et al. *Blood.* 2011; 117(3):839-47) of Sendai virus-negative Tn-iPSC colonies was seen in NOD-SCID-IL2Rgc immune deficient mice (FIG. 1I1). Analyses of Tsm-iPSCs included chromosomes (normal in Tn-iPSC clones tested from 3/3 donors and 1/1 Tsm donors). A representative example of Tn-iPSC clones and validation data is shown in Table 1.

TABLE 1

| T cells | Cell no. plated | iPSC-like colonies | Colonies picked | Validation assays |
|---|---|---|---|---|
| PT8-Tn-iPSC-V5 | $10^6$ | >100 | 74 | Sendai cleared, morphology; qRT-PCR; bisulfite seq., IF, cytogenetics, TCR rearrangement, teratoma in vivo |
| PT8-Tn-iPSC-V11 | $10^6$ | >100 | 74 | Sendai cleared, morphology; qRT-PCR; bisulfite seq., IF, cytogenetics, TCR rearrangement, teratoma in vivo |

TABLE 1-continued

| T cells | Cell no. plated | iPSC-like colonies | Colonies picked | Validation assays |
|---|---|---|---|---|
| PT8-Tn-iPSC-V12 | $10^6$ | >100 | 74 | Sendai cleared, morphology; qRT-PCR; bisulfite seq., IF, cytogenetics, TCR rearrangement, teratoma in vivo |
| PT9-Tn-iPSC | $10^6$ | >100 | 73 | Sendai cleared, morphology, qRT-PCR, IHC |
| PT10-Tn-iPSC | $10^6$ | >50 | 39 | Sendai cleared, morphology, qRT-PCR, IHC |
| PT12-Tn-iPSC | $10^6$ | 8 | 8 | |
| PT13-Tn-iPSC | $10^6$ | 14 | 14 | |
| PT15-Tsm-iPSC-V1 | $10^6$ | 1 | 1 | Sendai cleared, morphology; qRT-PCR; bisulfite seq., IF, cytogenetics, TCR rearrangement, teratoma in vivo |
| PT32-Tsm-iPSC-V1 | 150,000 | 133 | 62 | SeV cleared, morphology, qRT-PCR, bisulfite seq, IF, TCR rearrangement, Teratoma in vivo |
| PT32-Tsm-iPSC-V3 | 150,000 | 133 | 62 | SeV cleared, morphology, qRT-PCR, bisulfite seq, IF, TCR rearrangement, Teratoma in vivo |
| PT33-Tsm-iPSC-V2 | 300,000 | 106 | 57 | SeV cleared, morphology, qRT-PCR, bisulfite seq, IF, TCR rearrangement, Teratoma in vivo |
| PT33-Tsm-iPSC-V10 | 300,000 | 106 | 57 | SeV cleared, morphology, qRT-PCR, bisulfite seq, IF, TCR rearrangement, Teratoma in vivo |
| PT34-Tsm-iPSC- | 300,000 | 72 | 50 | morphology, qRT-PCR, IF, Teratoma in vivo |
| PT35-Tn-1-iPSC- | 300,000 | 35 | 22 | SeV cleared, morphology, qRT-PCR, bisulfite seq, IF, Teratoma in vivo |
| PT35-Tn-2-iPSC-V4 | 300,000 | 50 | 25 | SeV cleared, morphology, qRT-PCR, bisulfite seq, IF, TCR rearrangement, Teratoma in vivo |
| PT35-Tn-2-iPSC-V9 | 300,000 | 50 | 25 | SeV cleared, morphology, qRT-PCR, bisulfite seq, IF, TCR rearrangement, Teratoma in vivo |
| PT35-Tn-3-iPSC-V3 | 300,000 | 268 | 27 | SeV cleared, morphology, qRT-PCR, bisulfite seq, IF, TCR rearrangement, Teratoma in vivo |
| PT35-Tn-3-iPSC-V5 | 300,000 | 268 | 27 | SeV cleared, morphology, qRT-PCR, bisulfite seq, IF, TCR rearrangement, Teratoma in vivo |

In some embodiments, an iPSC derived from a T cell includes a clonal population of iPSCs. For example, an iPSC can include any of the clones listed in column 1 of Table 1, including, for example, PT15-Tsm-iPSC-V1, a clonal population of iPSCs derived from stem memory T cells; or PT8-Tn-iPSC-V5, a clonal population of iPSCs derived from naïve T cells.

In some embodiments, regulators of T cell differentiation can be manipulated in a T-iPSC, such as a T-IPSC derived from a T cell subset, for example, a Tn-iPSC, a Tcentral memory cell-iPSC, a Teffector-iPSC, a Teffector/memory-iPSC, a Teffector/memory/CD45RA+-iPSC, an NKT-iPSC cell, or a Tsm-iPSC. Manipulation can include, for example, chromosomal alterations.

In some embodiments, the expression of regulators of T cell differentiation may be increased and/or decreased using a viral or non-viral vector and/or electroporation, including, for example, microelectroporation. In some embodiments, the vector can include a transposable element including, for example, a piggyBac (PB) transposable element, Sleeping Beauty, and/or Tol2. In some embodiments, the vector can be targeted using a sequence-specific nuclease and/or system including, for example, Zinc finger nuclease (ZFN), a transcriptional activator-like effector nuclease (TALEN), and a two-component clustered regularly interspaced short palindromic repeat (CRISPR) system (e.g., a CRISPR-CRISPR-associated nuclease 9 (Cas9) system).

In some embodiments, regulators of T cell differentiation can include, for example, the BCL6 gene, which encodes the transcription factor, B-cell lymphoma 6 protein (BCL6); and/or the PRDM1 gene, which encodes BLIMP-1, a transcriptional repressor. BCL6 expression is high in naïve T cells (Tn), CD8 central memory T cells (Tcm), and T stem memory cells (Tsm), with expression decreasing with progressive differentiation. BLIMP-1 expression is high in senescent and terminally differentiated cells, with expression increasing with progressive differentiation. In some embodiments, inducing BCL6 upregulation and PRDM-1 down-regulation in an iPSC and/or a T cell progeny of an iPSC may allow increased T cell longevity to be achieved, may prolong T stem memory persistence, and/or may prolong retention in a T stem memory state.

Without being limited by the theory, since high bcl6 and low prdm1 are characteristic of T naïve cells (believed to be T stem memory cell precursors), enforcing a high ratio of bcl6:prdm1 in T stem memory-T progenitors or their T cell progeny may preserve the T stem memory state upon re-differentiation from Tsm-iPSCs; conversely a low bcl6:prdm1 ratio may drive differentiation away from a T stem memory phenotype even under optimal T stem memory re-differentiation conditions. By regulating bcl6/prdm1 (and other transcription factors) in differentiated T stem memory cells, characteristics of T stem memory cells can be optimally promoted or retained. Effects of transcription factor manipulations on a single cell basis can be compared by expanding individual colonies and splitting wells to obtain exact clonal daughter cells that can be analyzed, manipulated, and/or compared.

In one embodiment, to manipulate regulators of T cell differentiation, bcl6 and prdm1, iPSC colonies are treated with a gene editing meganuclease directed against the T cell receptor (TCR) alpha constant (TRAC) locus. Successful targeting of ~20% occurred (Osborn et al. *Human Gene Therapy*. 2011; 22(9):1155-65). For prdm1, reagents from clustered regularly interspaced short palindromic repeats (CRISPR)/Cas9 nuclease platform were generated and high-level modification in Tsm-iPSC cells was observed.

Differentiation of an iPSC to a T Progenitor Cell

This disclosure further describes a T progenitor cell derived from an induced pluripotent stem cell (iPSC), wherein the iPSC was derived from a T cell including a T cell of a T cell subset. This disclosure also describes methods for differentiating an iPSC including a T-iPSC to a T progenitor cell. In some embodiments, a T progenitor cell is defined as a CD3⁻ cell capable of differentiating into a T cell. A T-iPSC can include, for example, a Tn-iPSC, a T central memory cell-iPSC, a Teffector-iPSC, a Teffector/memory-iPSC, a Teffector/memory/CD45RA⁺-iPSC, an NKT-iPSC cell, and/or a Tsm-iPSC. In some embodiments, the T-iPSC is preferably a Tsm-iPSC.

In some embodiments, the differentiation of an iPSC to a T progenitor cell includes the formation of embryoid bodies. In some embodiments, a T-iPSC can be cultured in media and/or under conditions conducive to the formation of embryoid bodies. In some embodiments, a T-iPSC can be cultured in animal-product free (APEL) media and/or in TeSR1 media and/or on matrigel coated plates. In some embodiments, the media is preferably serum-free. In some embodiments, growth factors and/or inducers of mesoderm formation may be added including, for example basic fibroblast growth factor (bFGF) and/or bone morphogenetic protein (BMP)-4. In some embodiments, bFGF may be added at a concentration 1 ng/mL to 200 ng/mL. In some embodiments, BMP-4 may be added at a concentration 1 ng/mL to 200 ng/mL.

In some embodiments, a T-iPSC can be treated with a ROCK inhibitor. The ROCK inhibitor can inhibit cell death after dissociation. In some embodiments, 1 μM to 100 μM of a ROCK inhibitor be used. In some embodiments, a ROCK inhibitor can include Y-27632 dihydrochloride.

In some embodiments, a T-iPSC can be cultured in media and/or under conditions conducive to the formation of embryoid bodies can be further treated with a Wnt pathway activator including, for example, CHIR99021, CHIR-98014, LY2090314, BIO, IM-12, 3F8, A 1070722, CHIR 99021 trihydrochloride, L803-mts, SB 216763, SB 415286, TC-G 24, and/or TWS119. The Wnt pathway activator may be used in any concentration that produces the desired effect including, for example, from 100 nM to 100 μM. In some embodiments, a T-iPSCs cultured in media and/or under conditions conducive to the formation of embryoid bodies can be further treated with a TGFβ/Activin/Nodal inhibitor including, for example, SB431542 EW-7197, Galunisertib (LY2157299), LY2109761, SB525334, SD-208, SB505124, GW788388, and/or RepSox. The TGFβ/Activin/Nodal inhibitor may be used in any concentration that produces the desired effect including, for example, 100 nM to 100 μM.

In some embodiments, one embodiment of which is further described in Examples 4 and 9, a T-iPSC is cultured in serum-free APEL media including bFGF and BMP-4. In some embodiments, the media further includes a ROCK inhibitor. A Wnt pathway activator and/or a TGFβ/Activin/Nodal inhibitor can be added to the cell culture immediately after culture to form embryoid bodies is initiated or after at least 6 hours, at least 12 hours, at least 24 hours, at least 30 hours, at least 36 hours, at least 42 hours, or at least 48 hours. In some embodiments, a Wnt pathway activator and/or a TGFβ/Activin/Nodal inhibitor are added to the culture after 42 hours.

In some embodiments, the T-iPSC undergoing culture to form an embryoid body and/or an embryoid body formed from a T-iPSC can be treated with a heme specification cytokine, a hematopoietic cytokine, and/or bFGF. A heme specification cytokine and/or a hematopoietic cytokine can include, for example, stem cell factor (SCF), vascular endothelial growth factor (VEGF), FMS-like tyrosine kinase 3 ligand (Flt3L), and/or IL-3. The heme specification cytokine(s), hematopoietic cytokine(s), and/or bFGF may be used in any concentration that produces the desired effect including, for example, 1 ng/mL to 1 micrograms per milliliter (μg/mL). In some embodiments, the cytokine(s) and/or bFGF can be added at least 2 days, at least 3 days, at least 4 days, or at least 5 days after the initiation of culture conditions conducive to the formation of embryoid bodies.

In some embodiments, one embodiment of which is further described in Examples 4 and 9, a cell undergoing differentiation is treated in an APEL media including stem cell factor (SCF), vascular endothelial growth factor (VEGF), FMS-like tyrosine kinase 3 ligand (Flt3L), IL-3, and bFGF 3 days after culture to form embryoid bodies is initiated.

In some embodiments, a CD34⁺ cell can be enriched and/or separated from an embryoid body differentiated from a T-iPSC on day 8, day 9, day 10, day 11, or day 12 after culture to form embryoid bodies is initiated. In some embodiments, the CD34⁺ cell can be separated using magnetic separation, for example by using an EASYSEP™ hESC-Derived CD34 Positive Selection Kit, available from Stem Cell Technologies (Vancouver, British Columbia, Canada). In some embodiments, the CD34⁺ cell separated from an embryoid body is a hematopoietic progenitor cell.

In some embodiments, the cell undergoing differentiation from an iPSC to a T progenitor cell (e.g., a CD34⁺ cell) is further cultured with and/or on a stromal cell. In some embodiments, the stromal cell preferably expresses a Notch ligand. In some embodiments, the cell undergoing differentiation can be additionally or alternatively cultured with a soluble Notch ligand. In some embodiments, the stromal cells are OP9-DL4 cells and/or OP9-DL-1 cells. In some embodiments, the cell undergoing differentiation may be transferred to a culture including a stromal cell multiple times.

In some embodiments, the cell undergoing differentiation that is cultured with and/or on a stromal cell may simultaneously be cultured in media including SCF, IL-7, and/or Flt3L. The SCF, IL-7, and/or Flt3L may be used in any concentration that produces the desired effect including, for example, 1 ng/mL to 1 μg/mL. In some embodiments, the cell undergoing differentiation is cultured in media including SCF, IL-7, and Flt3L for 5 days, 6 days, 7 days, 8 days, 9 days, or 10 days. In some embodiments, the cell undergoing differentiation can then be cultured in media including IL-7, and Flt3L. In some embodiments, the cell undergoing differentiation that is cultured with and/or on a stromal cell may be cultured in the alpha-modification of minimum essential medium (α-MEM).

In some embodiments, the cell undergoing differentiation can be cultured with and/or on a stromal cell for at least 10 days, at least 12 days, at least 14 days, or at least 15 days.

In some embodiments, one embodiment of which is further described in Examples 4 and 9, a CD34⁺ cell undergoing differentiation is cultured on stromal cells in α-MEM medium including SCF, IL-7, and Flt3L.

Figure 3B:
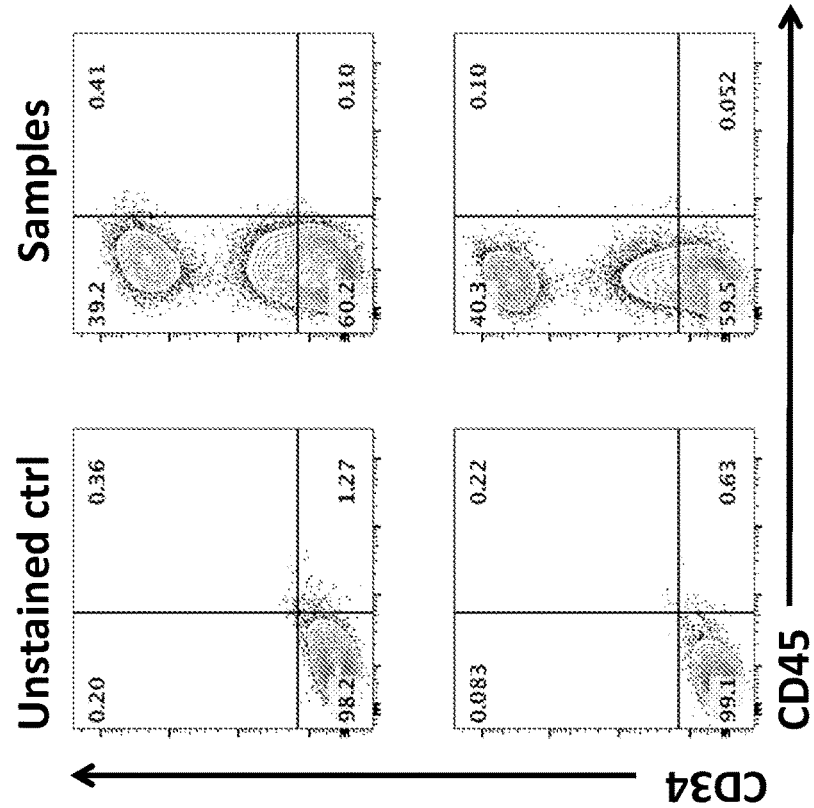
FIG. 3B. Day 9 hematopoietic progenitors were analyzed for the CD34 and CD45 expression. Left panels show unstained control.
Figure 3A:
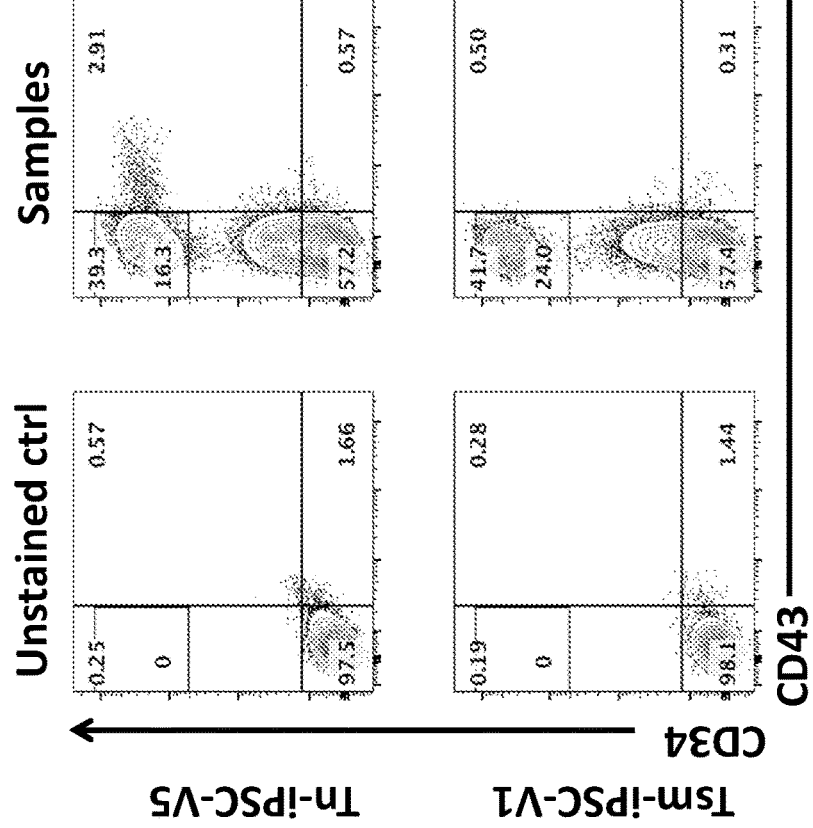
FIG. 3A. Tn- and Tsm-iPSC-derived hematopoietic progenitors were analyzed for the expression of CD34 and CD43 on day 9 of EB differentiation. $CD34^{hi}$ and $CD43^{low}$ sub gated population are progenitors of definitive hematopoiesis. Left panel shows unstained control.
Figure 4:
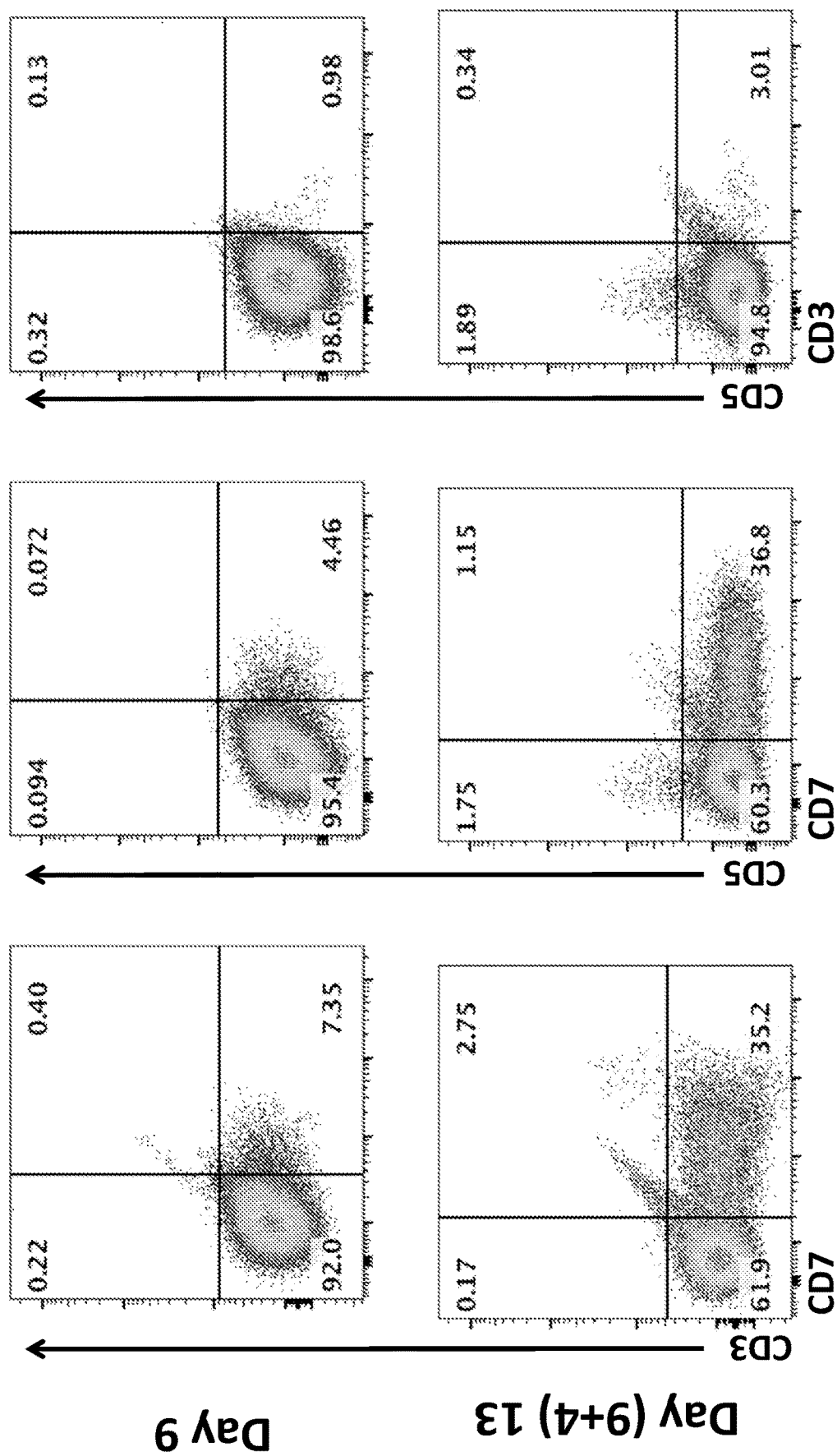
FIG. 4 shows flow exemplary cytometric analysis at day 9 of EB differentiation and day 13 (9 days EB+4 days OP9-DL4 co-culture). In the upper panel, Tsm-iPSC-derived EBs were dissociated at day 9 of differentiation and analyzed for the expression of CD3, CD5, and CD7. In the lower panel, $CD34^+$ cells were enriched using CD34 EASYSEP after 9 days of EB differentiation then co-cultured with OP9-DL4 stromal cells for 4 additional days followed by flow analysis of the indicated markers on day 13.

In one embodiment of differentiating an iPSC to a T progenitor cell, T cell derived iPSC (T-iPSC) colonies were dissociated into small clumps. Those clumps were differentiated by forming embryoid-bodies (EB) in serum-free animal-product free (APEL) media containing BMP4, VEGF, bFGF, a GSK3 inhibitor, hematopoietic cytokines, and 10% TesR1 for differentiation. Direct comparisons were made between OP9 feeders and serum containing media for inducing CD34⁺ cells. FIG. 3A shows CD34 and CD43 expression in Tsm-iPSCs (Kennedy et al. *Cell Reports*. 2012; 2(6): 1722-35.). By optimizing cytokines and using hypoxia conditions, both Tn-iPSCs and Tsm-iPSC colonies generated CD34$^{hi}$, CD43⁻ cells at day 9 of EB differentiation, a phenotype indicative of high hematopoietic and T cell differentiation potential. Further lymphocyte maturation markers CD7, CD5 and CD3 were absent at day 9, by day 13 approximately 35% lymphocyte progenitors were showing expression of CD7 (FIG. 4).

Figure 5A:
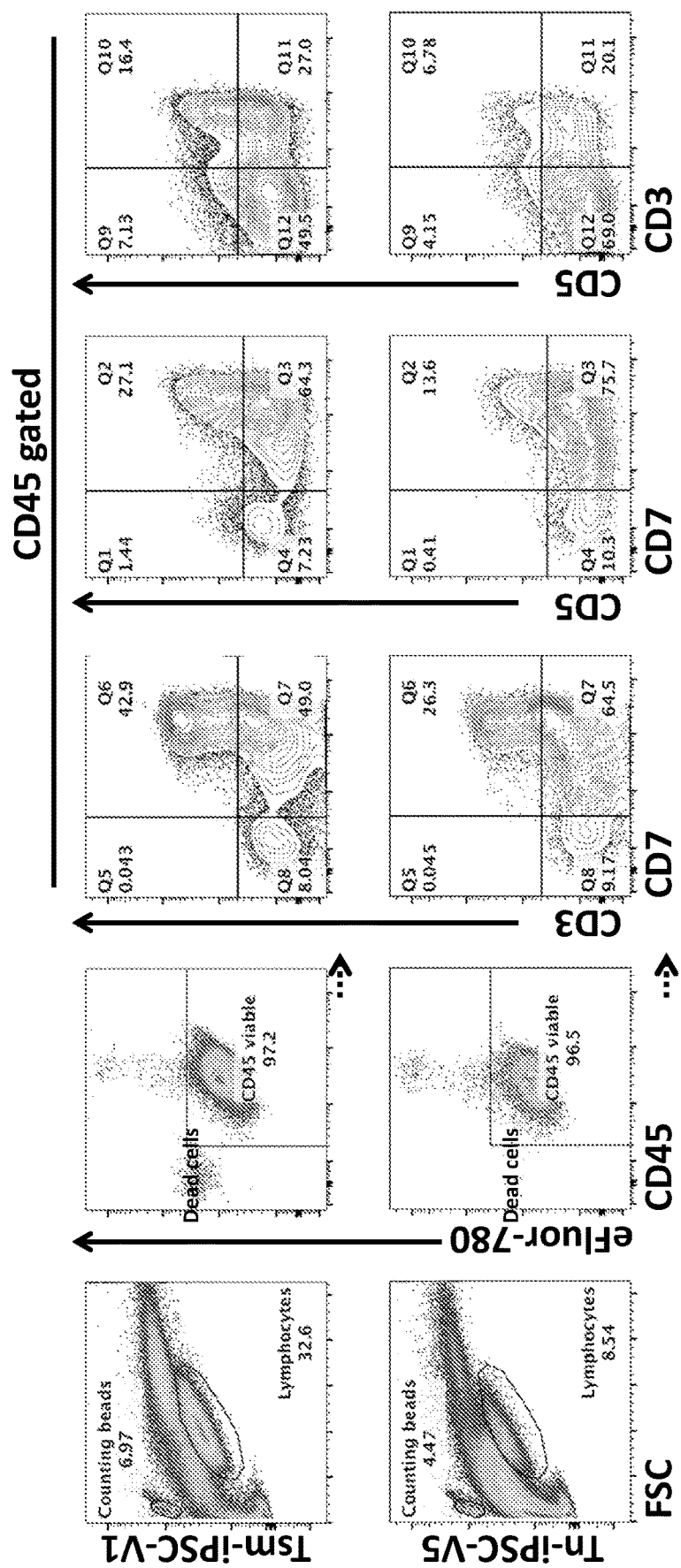
FIG. 5A. Tsm- and Tn-iPSC-derived EBs were dissociated at day 9 of differentiation, $CD34^+$ cells were enriched using CD34 EASYSEP and co-cultured with OP9-DL4 stromal cells for 7 additional days. Desired lymphocyte populations were gated stringently; viable CD45 positive cells were analyzed by flow cytometric analysis for the indicated markers on day 16. Dashed arrows indicate sub-gating strategies. OP9-DL4 stromal cells were freshly plated every 4 to 5 days.
Figure 5B:
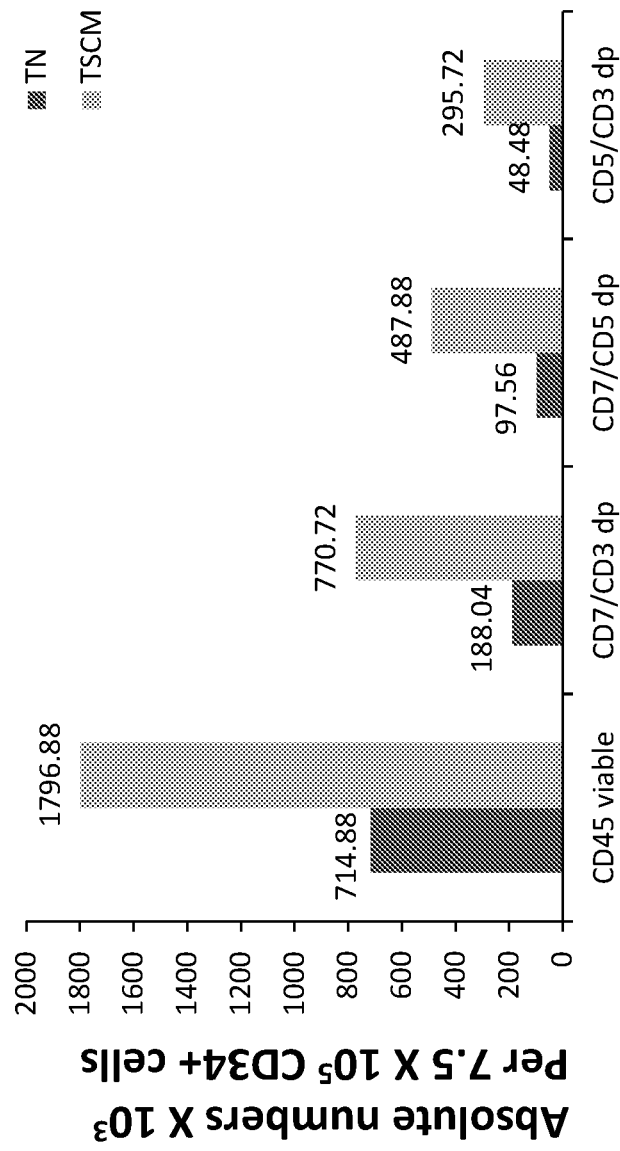
FIG. 5B. Tsm- and Tn-iPSC-derived EBs were dissociated at day 9 of differentiation, $CD34^+$ cells were enriched using CD34 EASYSEP. $7.5 \times 10^5$ $CD34^+$ hematopoietic progenitors were co-cultured with OP9-DL4 stromal cells for 7 additional days. Samples were gated for lymphocyte population and then analyzed for CD45 expression and Alexa eFluor-780 staining. Dead cells, labeled with Alexa eFluor-780, and CD45-negative cells were excluded from further analysis. Absolute T progenitor cell numbers shown on the Y-axis represent the total number of cells derived from $7.5 \times 10^5$ $CD34^+$ hematopoietic progenitor input cells after 7 days co-culture (total differentiation day 16=9 days embryoid body differentiation+7 days OP9-DL4 co-culture). Cell numbers were compared between Tn-iPSC- and Tsm-iPSC-derived T progenitors. Absolute cell numbers of viable CD45 positive cells, CD3/CD7 double positive, CD7/CD5 double positive and CD3/CD5 double positive groups are shown.
Figure 5C:
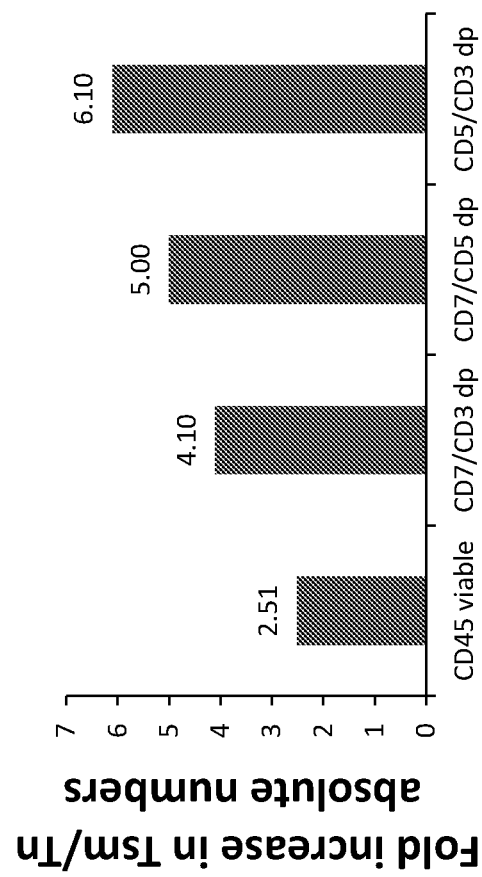
FIG. 5C. Fold increase in absolute cell numbers of Tsm versus Tn for indicated groups.
Figure 6:
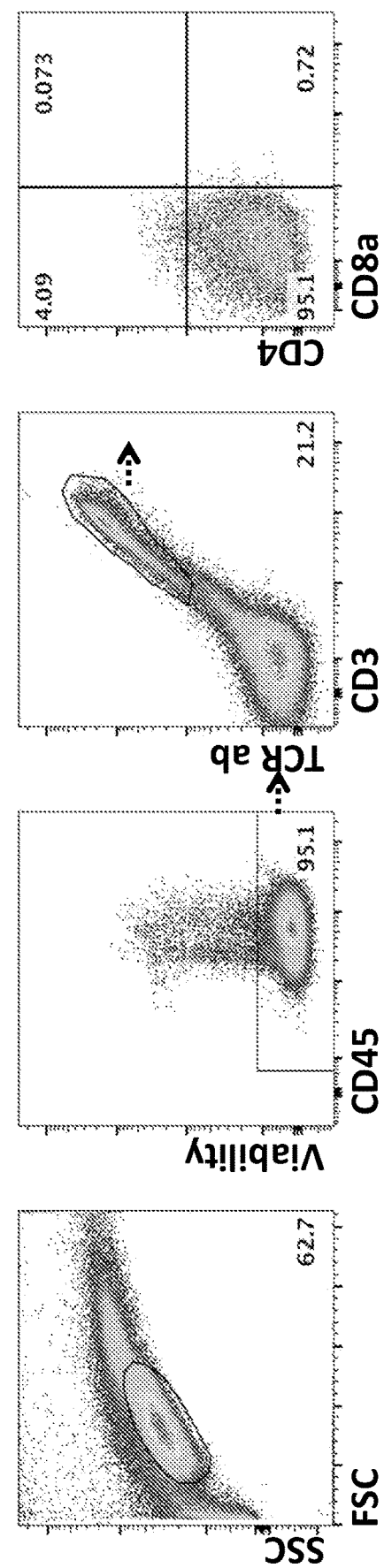
FIG. 6 shows exemplary flow cytometric analysis at day 16 (9 days EB+7 days OP9-DL4 co-culture) of viability and CD45, CD3, T cell receptor (TCR), CD4, and CD8 expression. Tsm- and Tn-iPSC-derived EBs were dissociated at day 9 of differentiation, CD34$^+$ cells were enriched using CD34 EASYSEP and co-cultured with OP9-DL4 stromal cells for 7 additional days. Desired lymphocyte populations were gated stringently; viable CD45 positive cells were analyzed by flow cytometric analysis for indicated markers on day 16. Dashed arrows indicate sub-gating strategies. OP9-DL4 stromal cells were freshly plated every 4 to 5 days.
Figure 7:
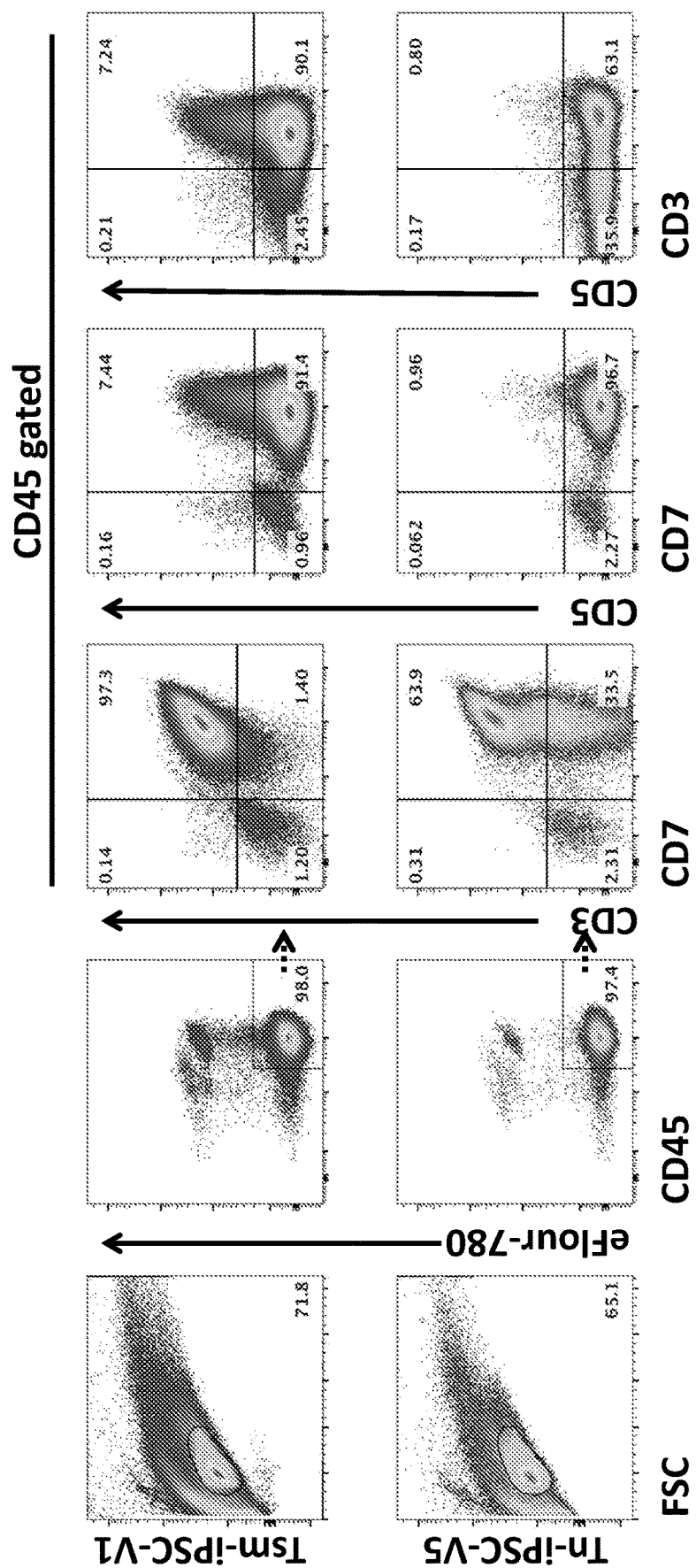
FIG. 7 shows exemplary flow cytometric analysis at day 23 (9 days EB+14 days OP9-DL4 co-culture) of viability and CD45, CD3, CD7, and CD5 expression. Tsm- and Tn-iPSC-derived EBs were dissociated at day 9 of differentiation, CD34$^+$ cells were enriched using CD34 EASYSEP and co-cultured with OP9-DL4 stromal cells for 14 additional days. Desired lymphocyte populations were gated stringently; viable CD45 positive cells were analyzed by flow cytometric analysis for indicated markers on day 23. Dashed arrows indicate sub-gating strategies. OP9-DL4 stromal cells were freshly plated every 4 to 5 days.
Figure 31:
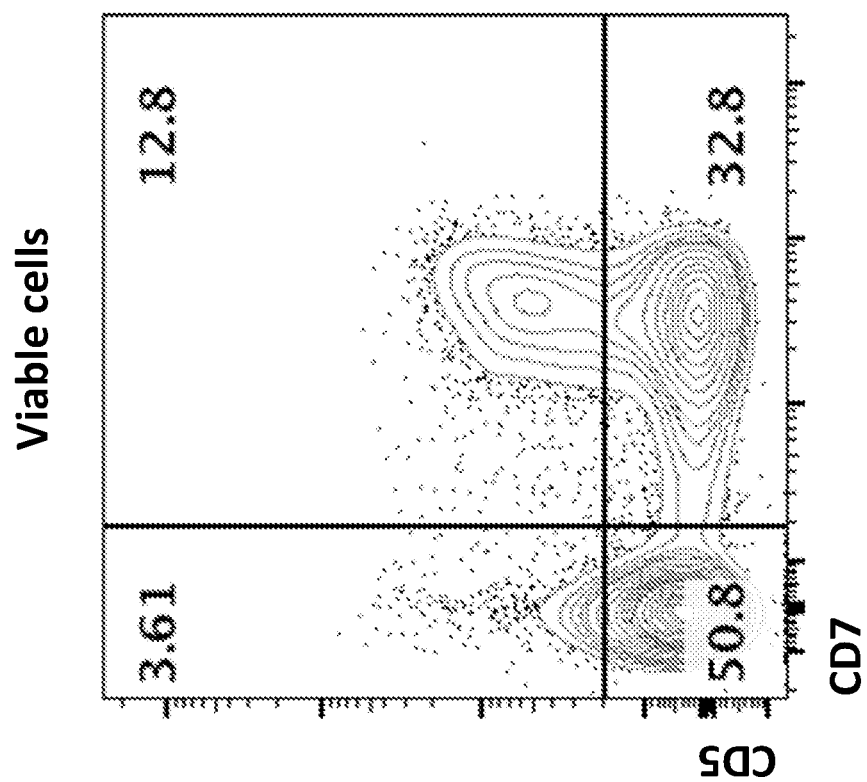
FIG. 31 shows analysis of CS-1-iPSC derived T progenitors at day (9+12) 21. CS-1-iPSC derived CD34$^+$ cells were enriched and co-cultured on OP9-DL4 for 12 days as described in STEP II of Example 9 (total day 9+12=21 days) followed by flow analysis of indicated markers.
Figure 33C:
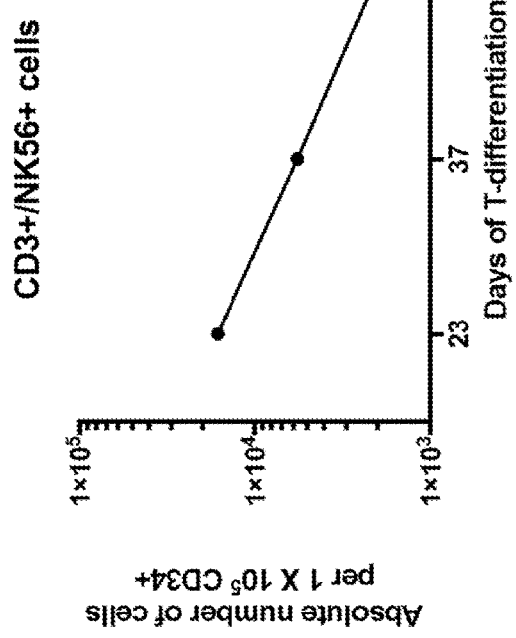
FIG. 33C. Time point analysis indicate absolute numbers of CD3$^+$/CD56$^+$ NKT cells during STEP II of T progenitor differentiation as described in Example 9.
Figure 33D:
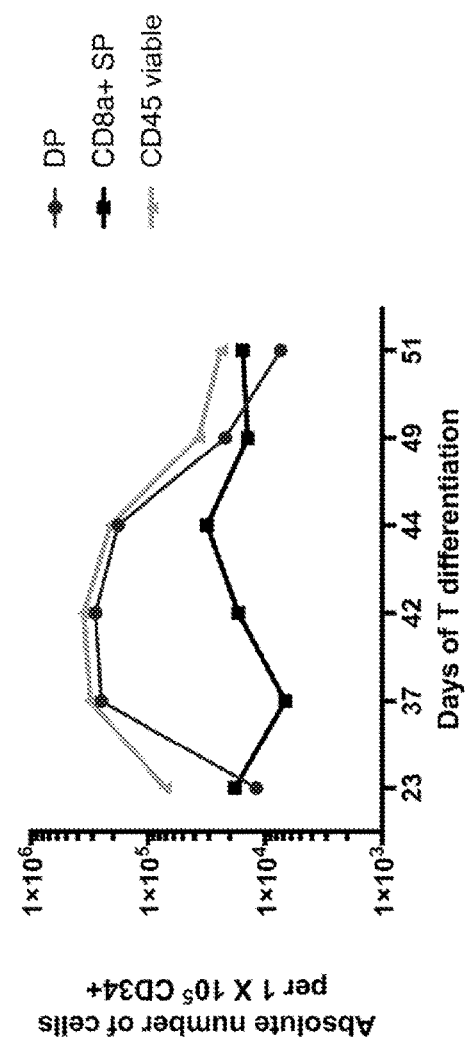
FIG. 33D. Time kinetics of absolute cell numbers of indicated groups during T progenitor differentiation. An increase in DP-T cells was observed by day 37 and an increase in the number of CD8 single positive (SP) cells was observed thereafter.
Figure 34A:
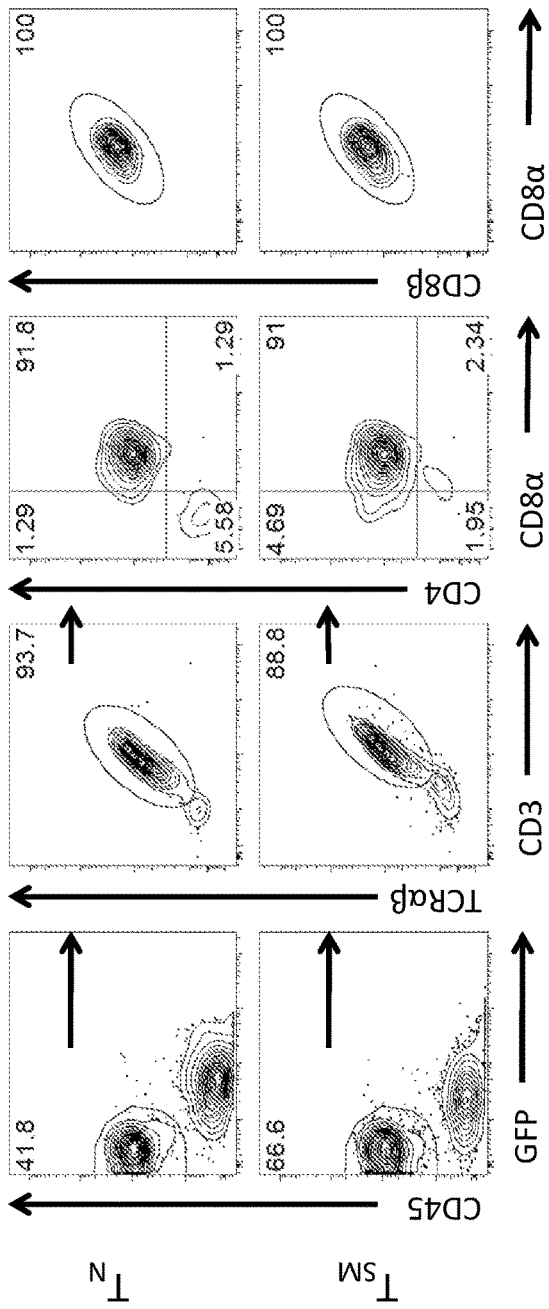
FIG. 34A. Comparison of Tsm- and Tn-iPSCs derived T progenitors development at day 37 (9+28) using indicated markers in flow cytometric analysis. Comparison of Tn/Tsm-iPSC derived TCRαβ (FIG. 34B) and CD8αβ (FIG. 34C) expressing T progenitor cells frequencies of depicted groups at indicated time points.
Figure 34C:
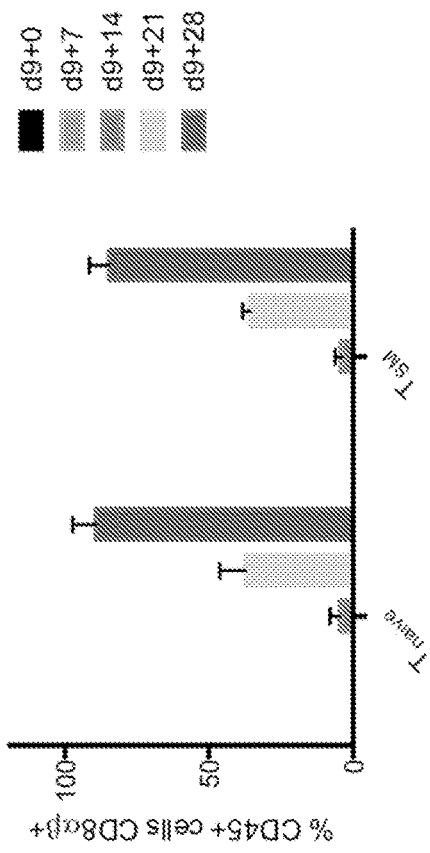
FIG. 34(A-C) shows exemplary T progenitor development.
Figure 34B:
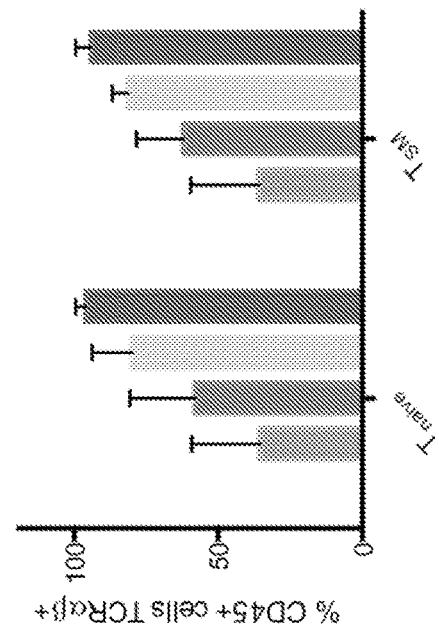
Figure 35:
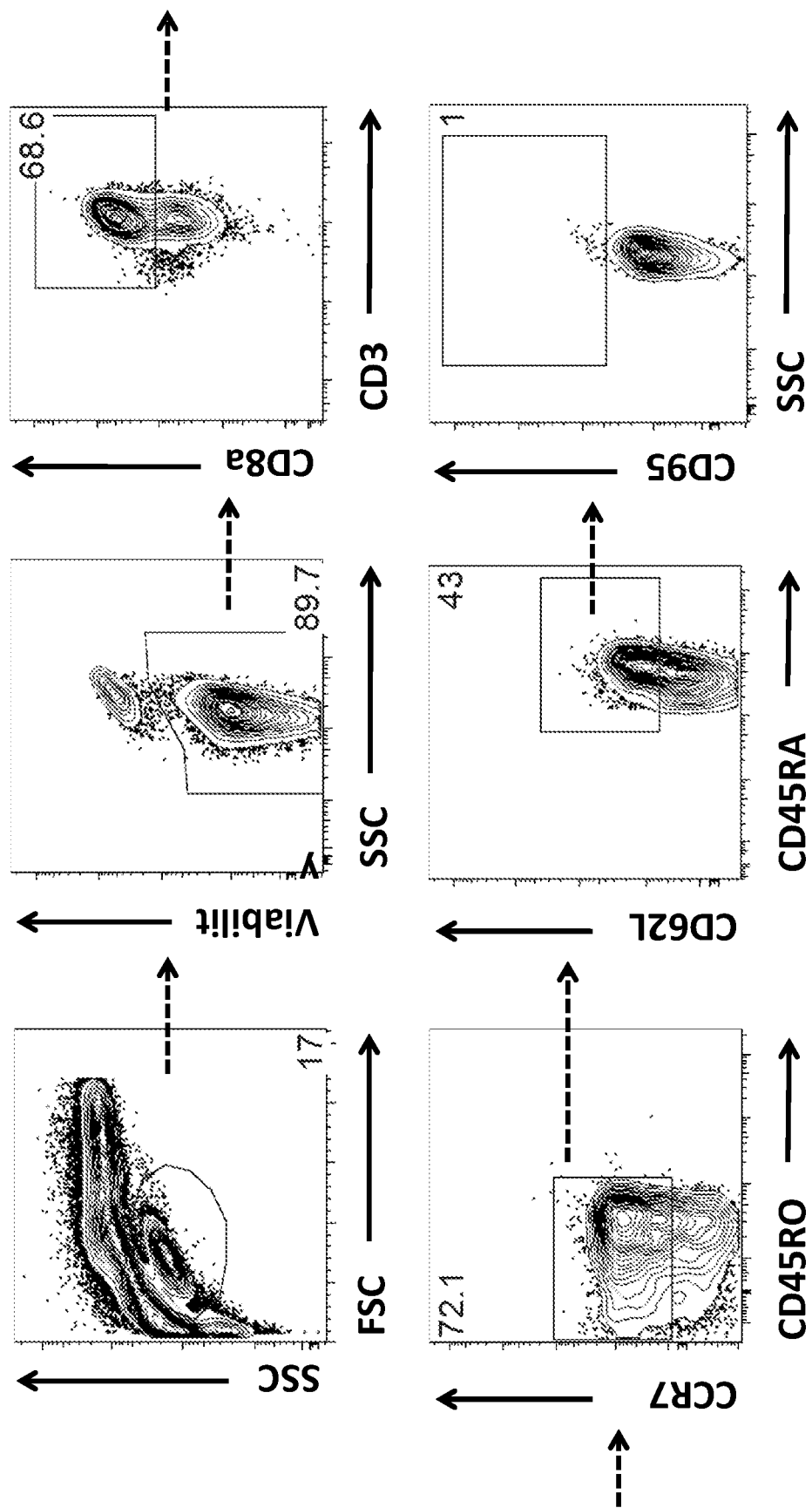
FIG. 35 shows an exemplary naïve phenotype of day 40 (9+31) Tsm iPSCs before stimulation. Tsm-iPSCs were differentiated following STEP I and STEP II of differentiation protocol, as described in Example 9, for 9+31=40 days. Flow cytometric analysis of T naïve cell phenotype; gating strategies are indicated by dashed arrows.
Figure 36:
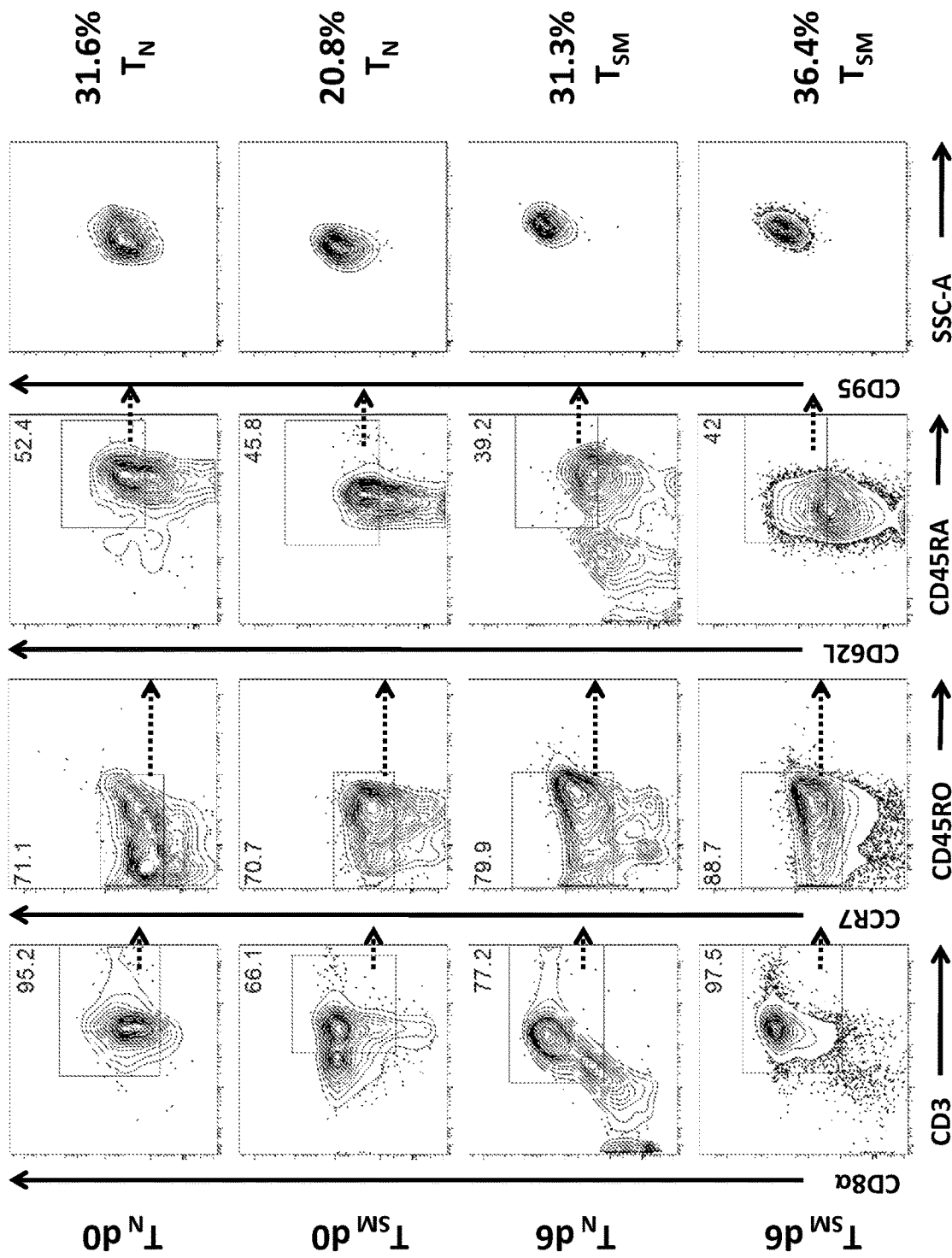
FIG. 36 Tn/Tsm-iPSCs derived DP-T cells at day 37 stimulated using anti CD3/28 antibodies conjugated micro beads. Tsm/Tn cellular phenotypes were flow analyzed at pre stimulation (day 0) or 6 days post stimulation. Dashed arrows indicating gating strategies for flow analysis.

Tn/Tsm-iPSC derived CD34+ cells were co-cultured for an additional 7 days (d16 in FIG. 5) on OP9-DL4 to generate T cells; ~90% of CD45+ cells were CD7+; 14-26% co-expressed CD5, 25-42% of them were CD3+, characteristic of in vivo engrafting human T cells. Immature T cells co-expressed CD3 and TCRα/β due to TCR pre-rearrangement in the T cell clone that produced the iPSC colony (FIG. 6). While CD8 cells were seen (FIGS. 8, 9, 10), these cells were observed at a low frequency. In stark contrast, no CD8+ T cells were observed when dermal fibroblast-derived iPSCs instead of T-iPSCs were used to generate T cells (FIGS. 31, 32). For example, FIG. 31 shows that 12 days differentiation of fibroblast-derived CD34+ cells on OP9-DL4 stroma results in T progenitor cells expressing CD5 and CD7 markers. FIG. 32 shows that co-culture of fibroblast-derived CD34+ cells on OP9-DL4 stroma for 15 days generates CD45+ viable T cells that lack expression of TCRαβ and CD3. In contrast, at this stage Tn/Tsm-iPSC derived T cells express both TCRαβ and CD3.

T cells have been previously re-differentiated from human T-iPSCs (Vizcardo et al. *Cell Stem Cell.* 2013; 12(1):31-6; Nishimura et al. *Cell Stem Cell.* 2013; 12(1):114-26). But, as described herein, T-iPSC derived specifically from T naïve and T stem memory cells can be differentiated into a T progenitor cell and/or a T cell of a T cell subset (see, e.g., FIGS. 8, 9, 10, 21 and 22).

Figure 8B:
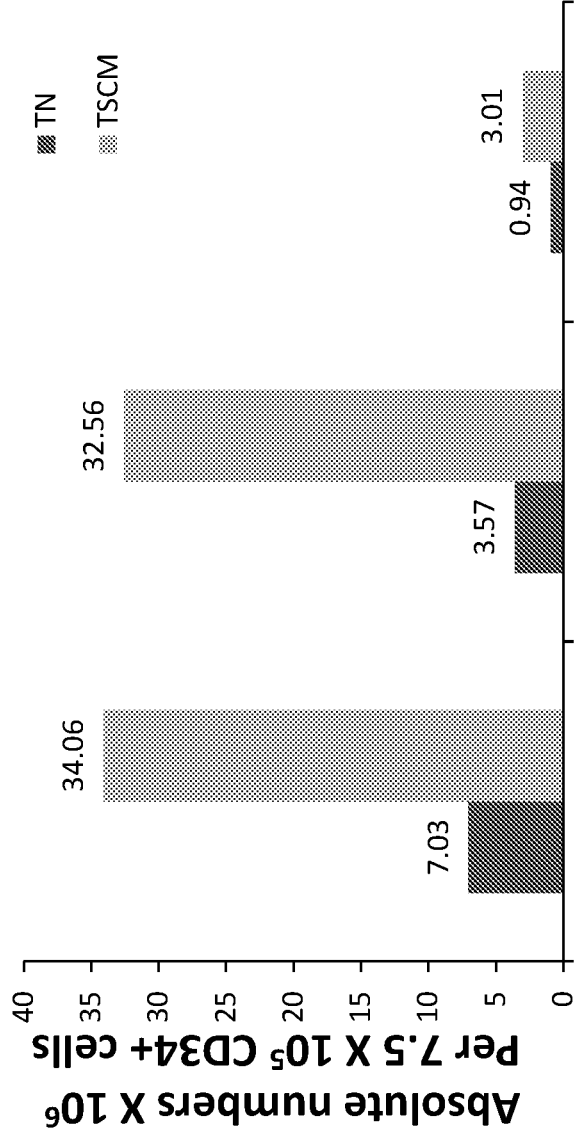
FIG. 8B. Tsm- and Tn-iPSC-derived EBs were dissociated at day 9 of differentiation, CD34$^+$ cells were enriched using CD34 EASYSEP. 7.5×10$^5$ CD34$^+$ hematopoietic progenitors are co-cultured with OP9-DL4 stromal cells for 14 additional days. Absolute cell numbers comparison of viable CD45 positive cells, CD3/TCRαβ (also referred to herein as TCRα/β, or TCRab) double positive and CD8 alpha (CD8a) single positive groups.
Figure 8C:
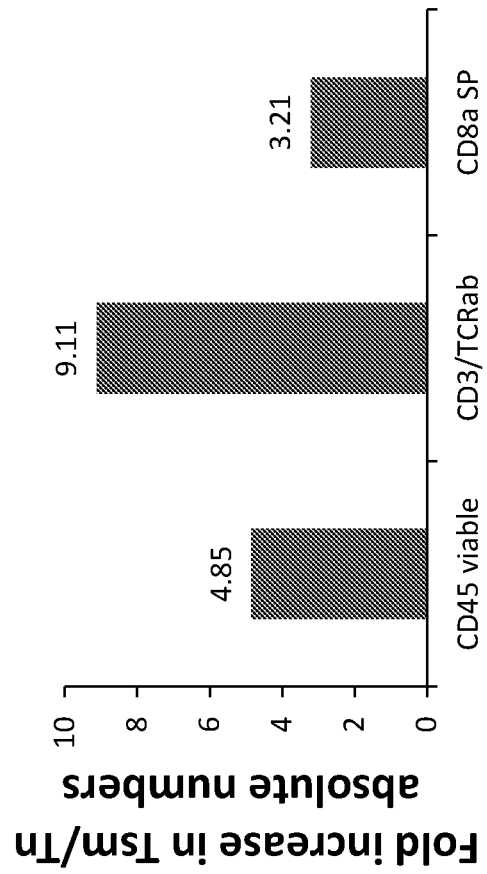
FIG. 8C. Fold increase in absolute cell numbers of Tsm versus Tn for indicated groups.
Figure 9B:
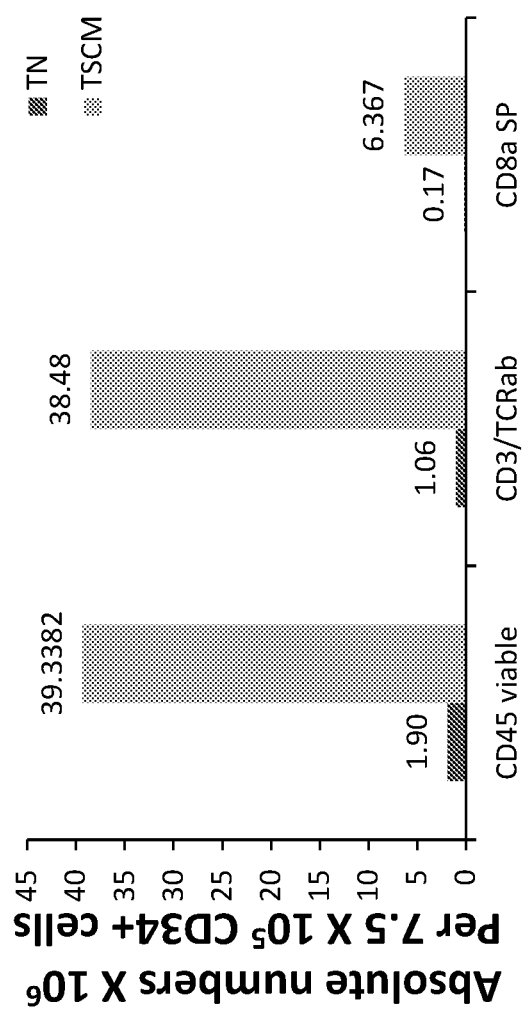
FIG. 9B. Tsm- and Tn-iPSC-derived EBs were dissociated at day 9 of differentiation, CD34$^+$ cells were enriched using CD34 EASYSEP. 7.5×10$^5$ CD34$^+$ hematopoietic progenitors are co-cultured with OP9-DL4 stromal cells for 21 additional days. Absolute cell numbers comparison of viable CD45 positive cells, CD3/TCRαβ double positive and CD8a (alpha) single positive groups.
Figure 9C:
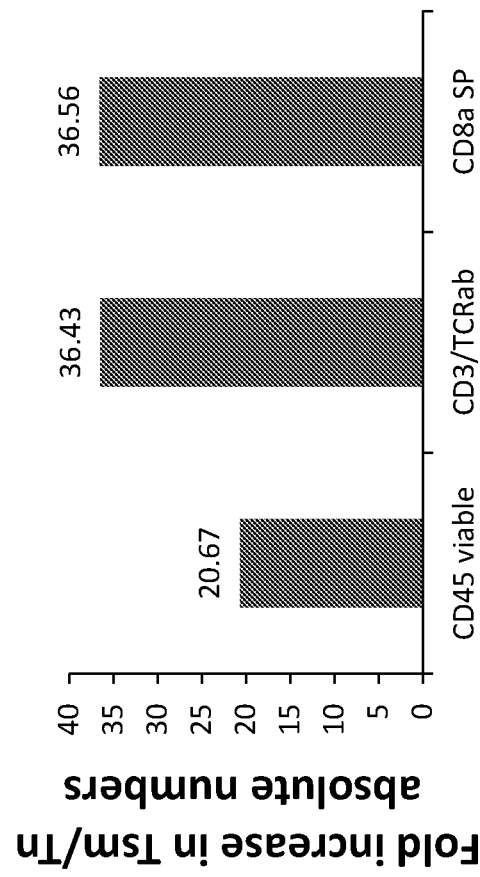
FIG. 9C. Fold increase in absolute cell numbers of Tsm versus Tn for indicated groups.
Figure 10A:
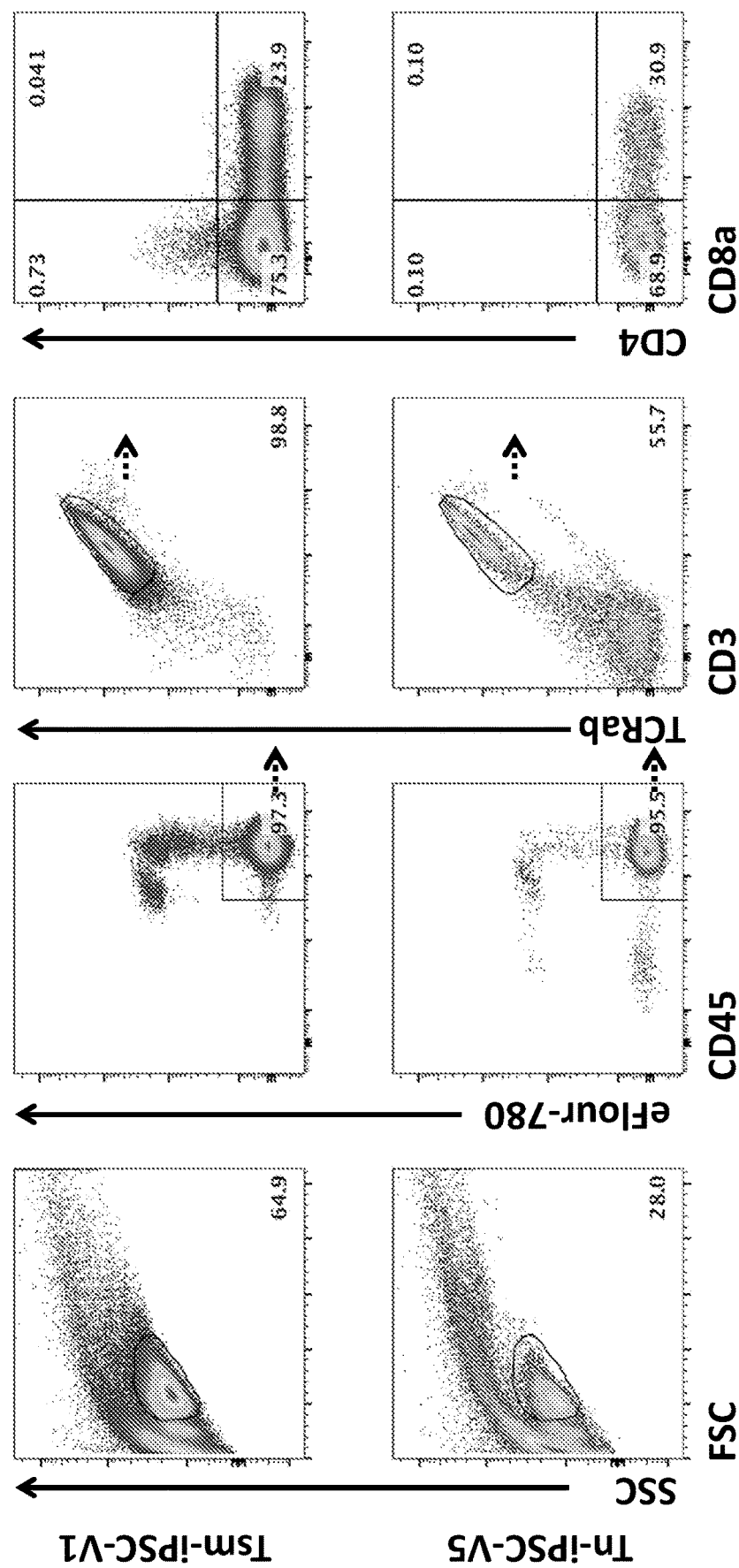
FIG. 10A. Tsm- and Tn-iPSC-derived EBs were dissociated at day 9 of differentiation, CD34$^+$ cells were enriched using CD34 EASYSEP and co-cultured with OP9-DL4 stromal cells for 28 additional days. Desired lymphocyte populations were gated stringently; viable CD45 positive cells were analyzed by flow cytometric analysis for indicated markers on day 37. Dashed arrows indicate sub-gating strategies. OP9-DL4 stromal cells were freshly plated after every 4 to 5 days.
Figure 10B:
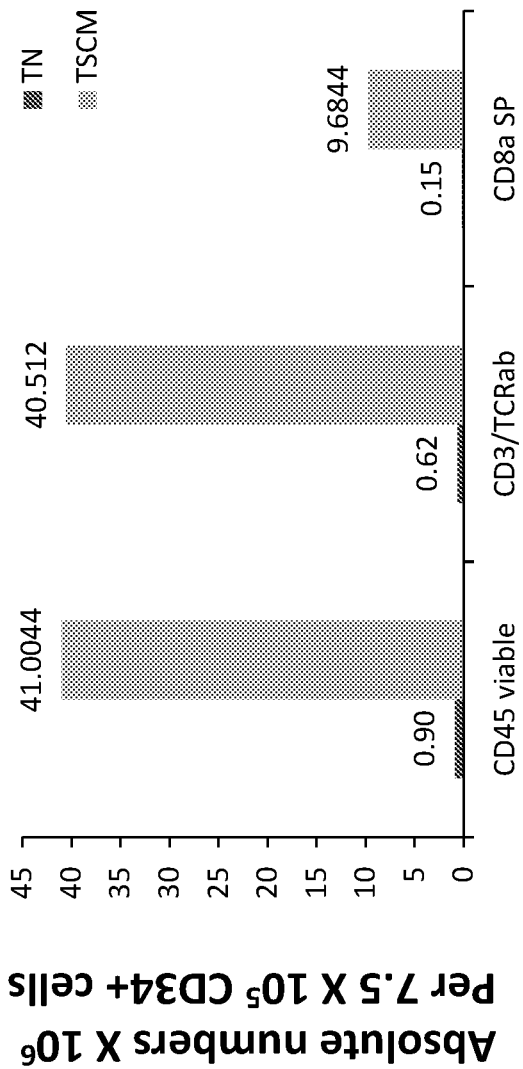
FIG. 10B. Tsm- and Tn-iPSC-derived EBs were dissociated at day 9 of differentiation, CD34$^+$ cells were enriched using CD34 EASYSEP. 7.5×10$^5$ CD34$^+$ hematopoietic progenitors are co-cultured with OP9-DL4 stromal cells for 28 additional days. Absolute cell numbers comparison of viable CD45 positive cells, CD3/TCRαβ α double positive and CD8a (alpha) single positive groups.
Figure 10C:
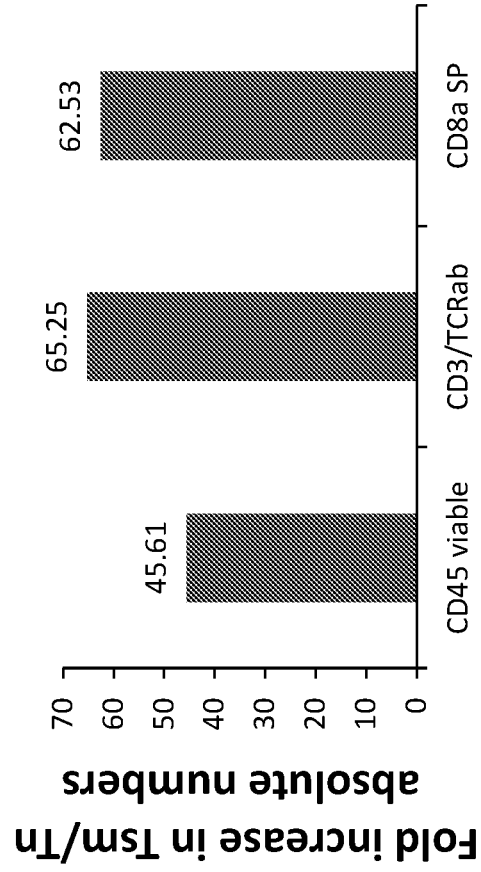
FIG. 10C. Fold increase in absolute cell numbers of Tsm versus Tn for indicated groups.
Figure 11A:
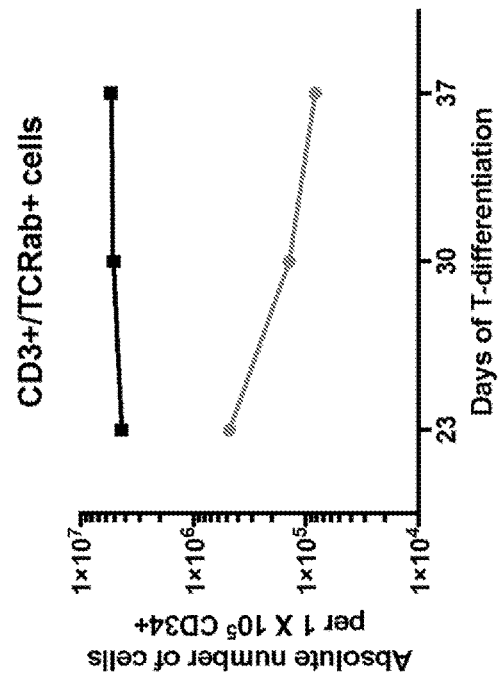
FIG. 11(A-C) shows an exemplary comparison of absolute cell numbers of Tn- and Tsm-iPSC-derived T progenitors/cells during in vitro T cell development. Tsm- (squares) and Tn- (circles) iPSC-derived EBs were dissociated at day 9 of differentiation, CD34$^+$ cells were enriched using CD34 EASYSEP. 7.5×10$^5$ CD34$^+$ hematopoietic progenitors were co-cultured with OP9-DL4 stromal cells for the number of days indicated on the X-axis. Absolute cell numbers of FIG. 11A, viable CD45 positive cells.
FIG. 11B, CD3/TCRαβ double positive cells.
FIG. 11C, CD8a (alpha) single positive cells are shown.
Figure 11B:
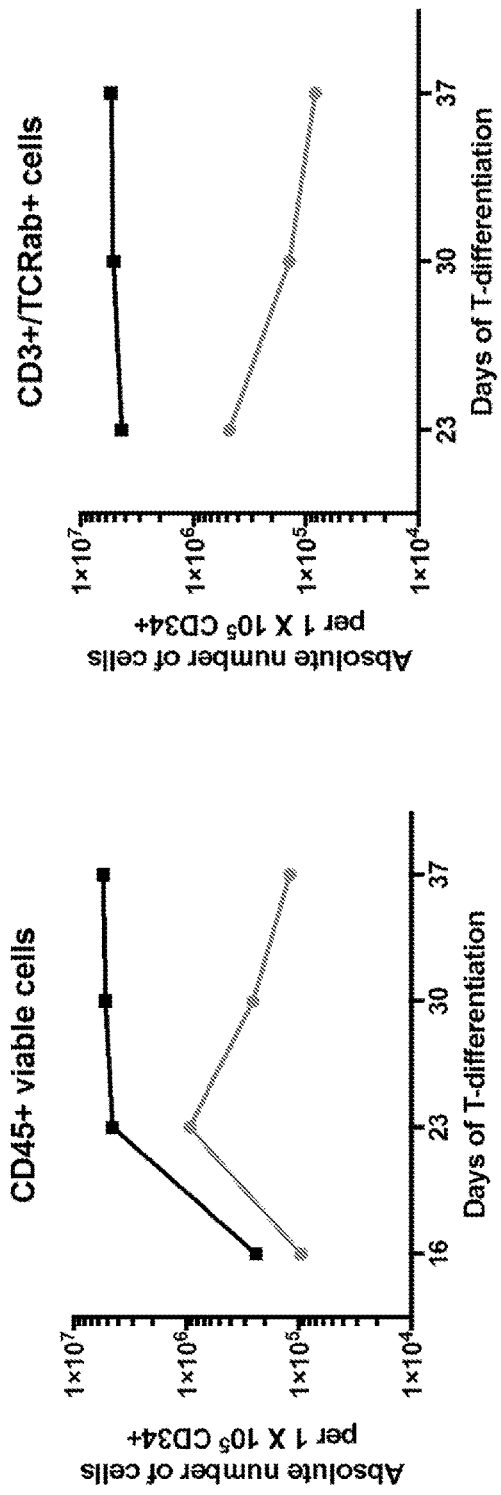
Figure 11C:
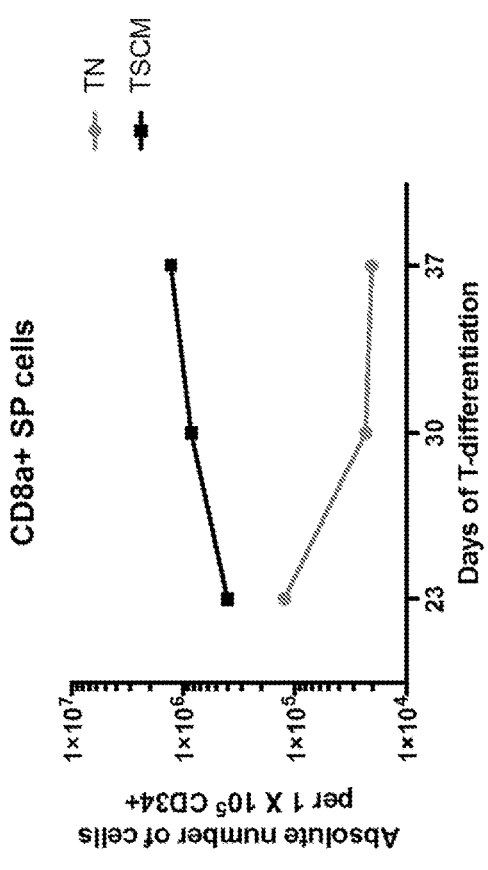
Figure 13:
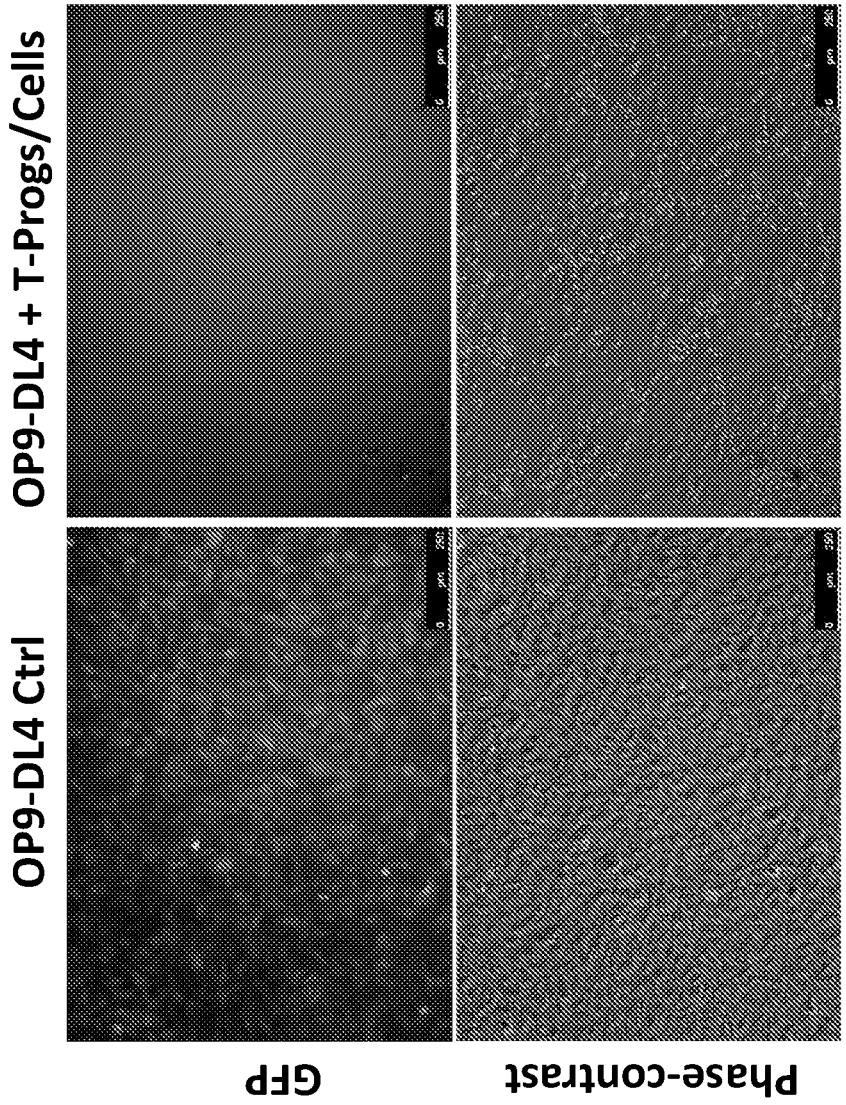
FIG. 13 shows exemplary cytotoxic function of in vitro-differentiated T cells at day 18. T-iPSC-derived EBs were dissociated at day 9 of differentiation, CD34$^+$ cells were enriched using CD34 EASYSEP. Then 7.5×10$^5$ CD34$^+$ hematopoietic progenitors were co-cultured with OP9-DL4 stromal cells for 7 additional days. Subsequently, 1.2×10$^6$ CD45 T cells were seeded on 2.5×10$^4$ OP9-DL4 cells over-expressing Notch ligand DLL4 fused with GFP reporter. Images were taken 48 hours later at day 18 and show destruction of GFP-expressing stromal cells on the top right side panel.
Figure 14A:
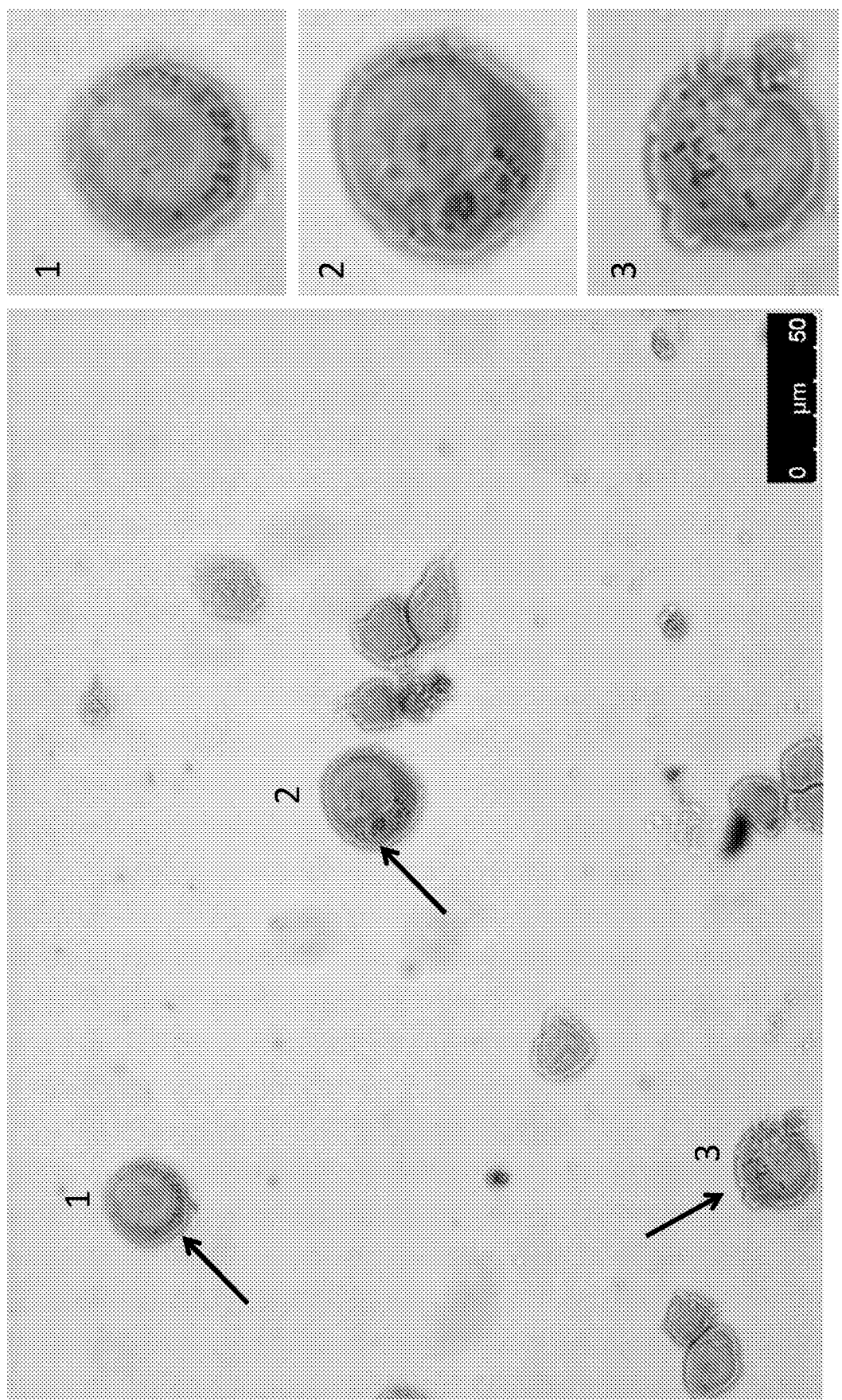
FIG. 14A. Giemsa staining shows cytolytic granules in Tsm-iPSC-derived cytotoxic T cells. Activated T cells are around 20-25 micrometers (μm) in size, indicated with black arrows. Right panel shows enlarged images of labeled T cells.
Figure 14B:
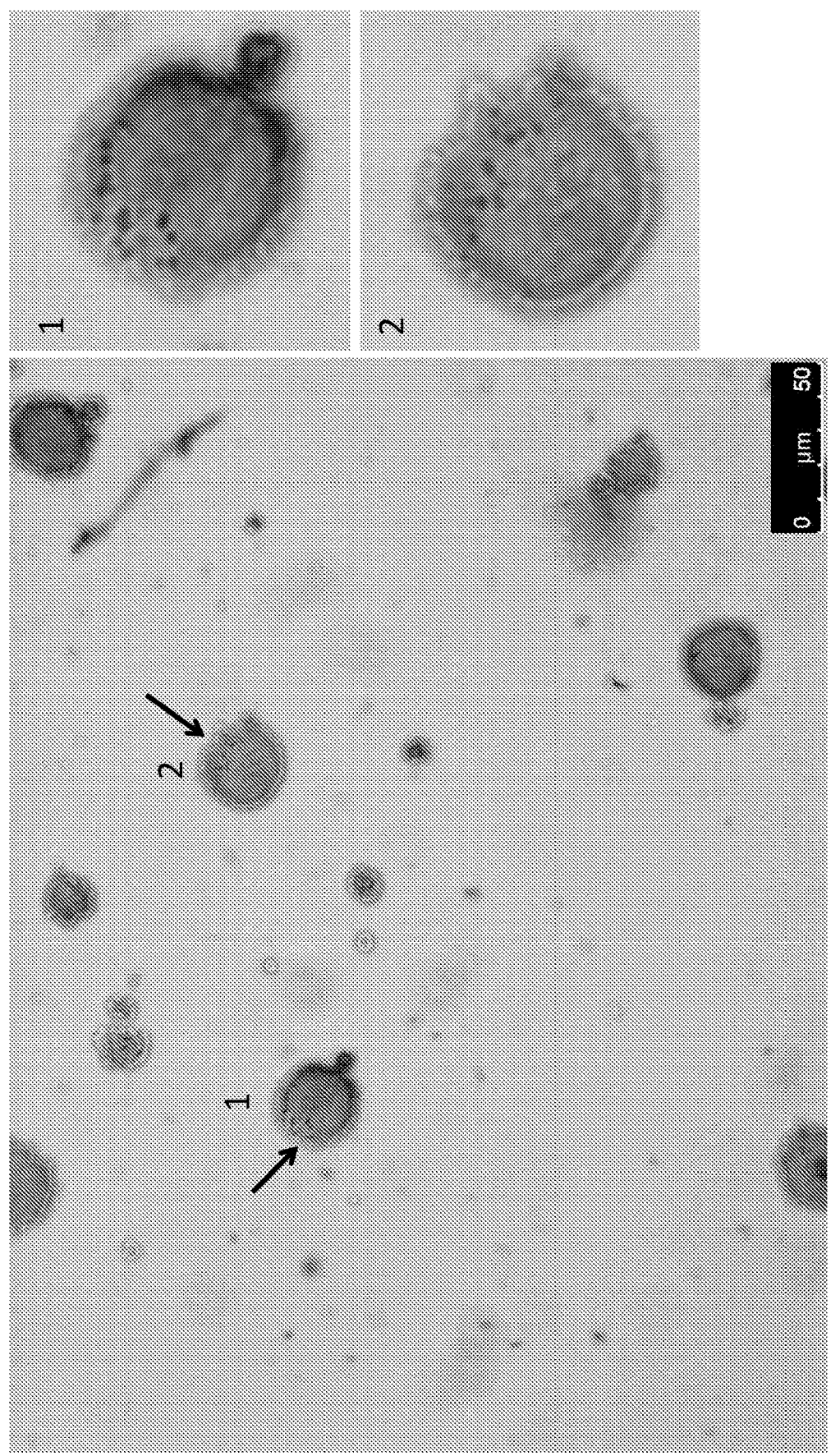
FIG. 14B. Giemsa staining shows cytolytic granules in Tn-iPSC-derived cytotoxic T cells. Activated T cells are around 20-25 μm in size, indicated with black arrows. Right panels show enlarged images of labeled T cells.
Figure 15A:
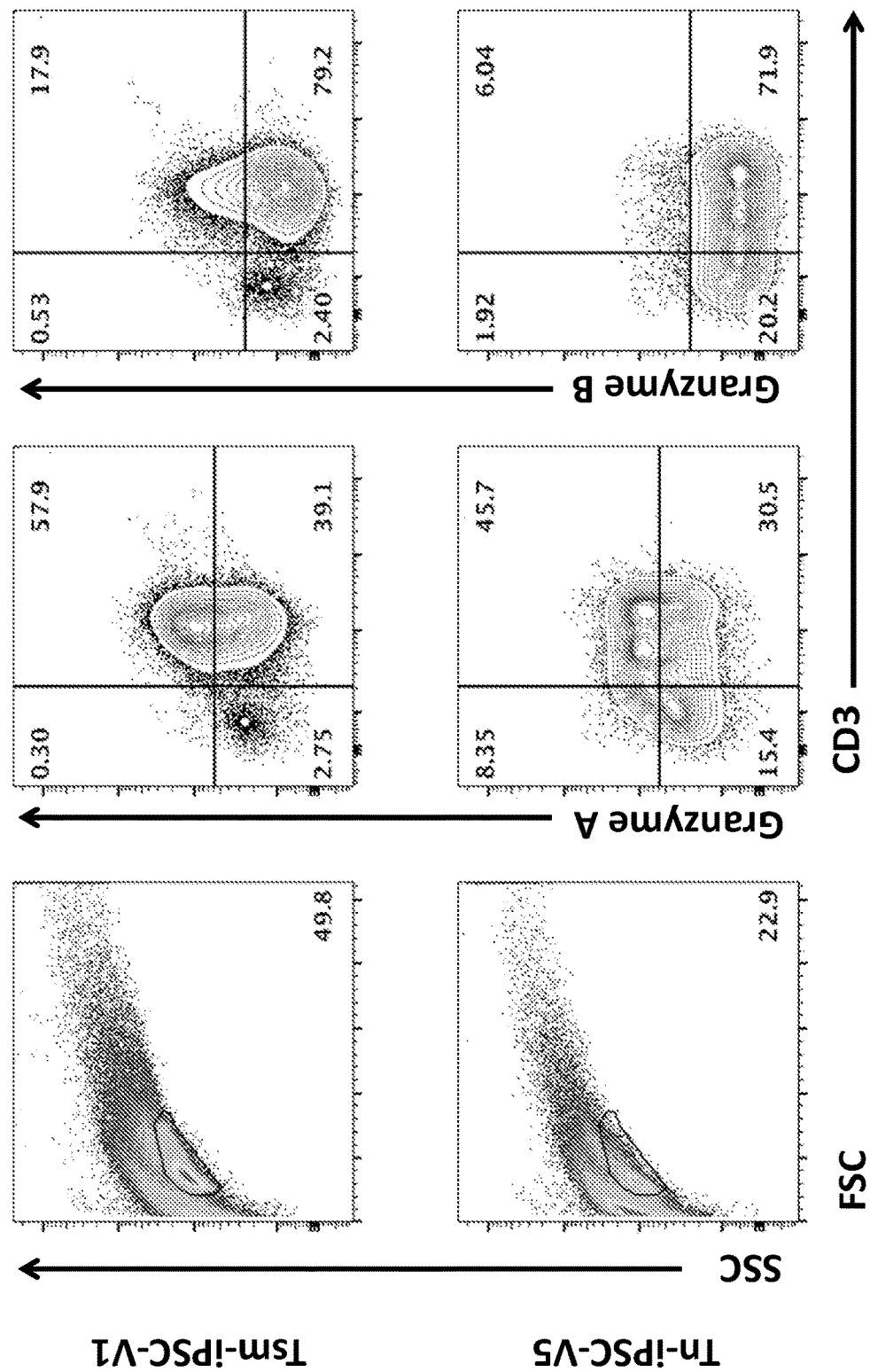
FIG. 15A. T-iPSC-derived cytotoxic T cells show expression of cytolytic enzymes Granzyme A and Granzyme B at day 22 of differentiation.
Figure 15B:
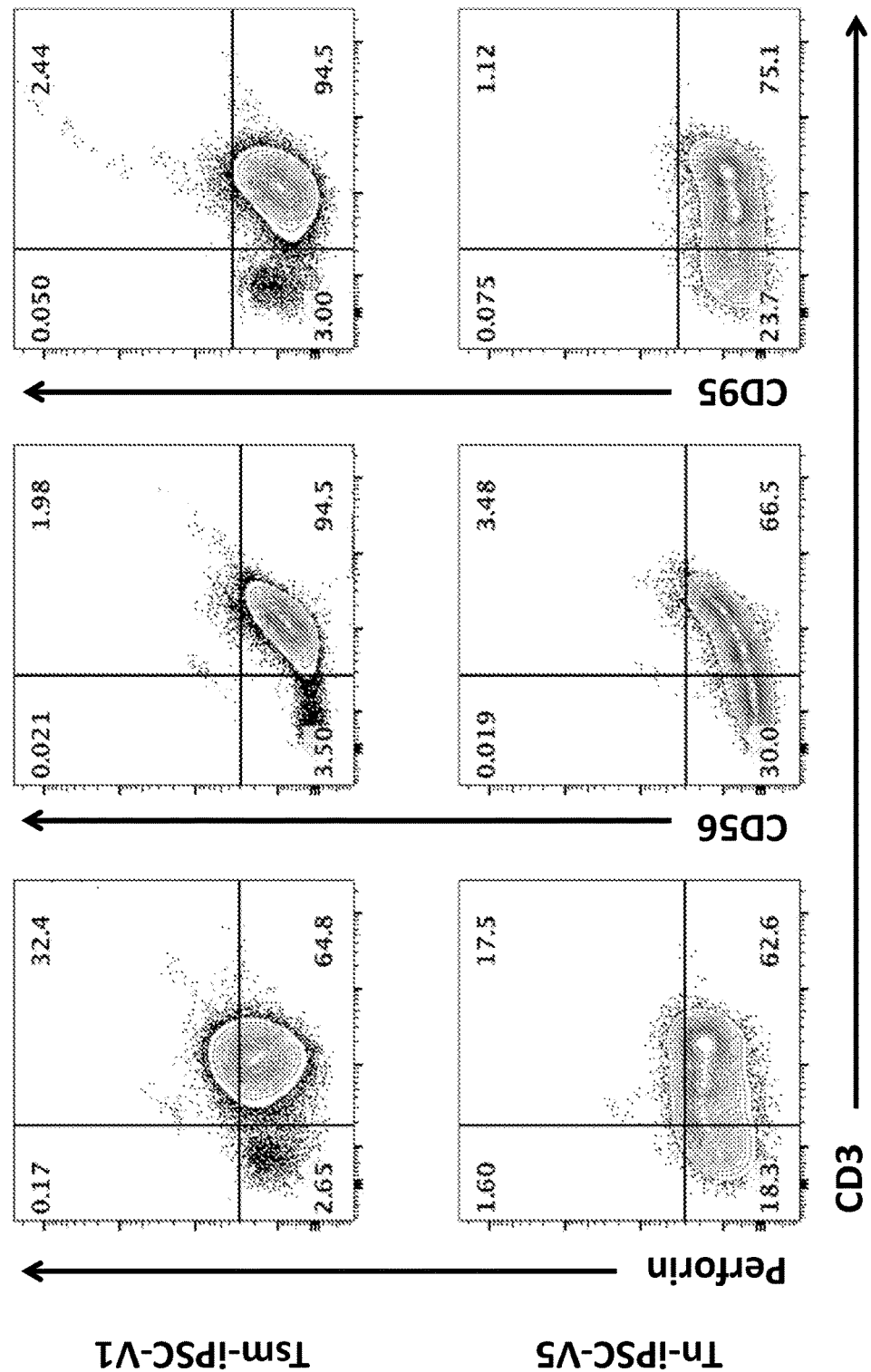
FIG. 15B. T-iPSC-derived cytotoxic T cells show expression of perforin but not NK marker CD56 and memory T cell marker CD95 at day 22 of differentiation.
Figure 15C:
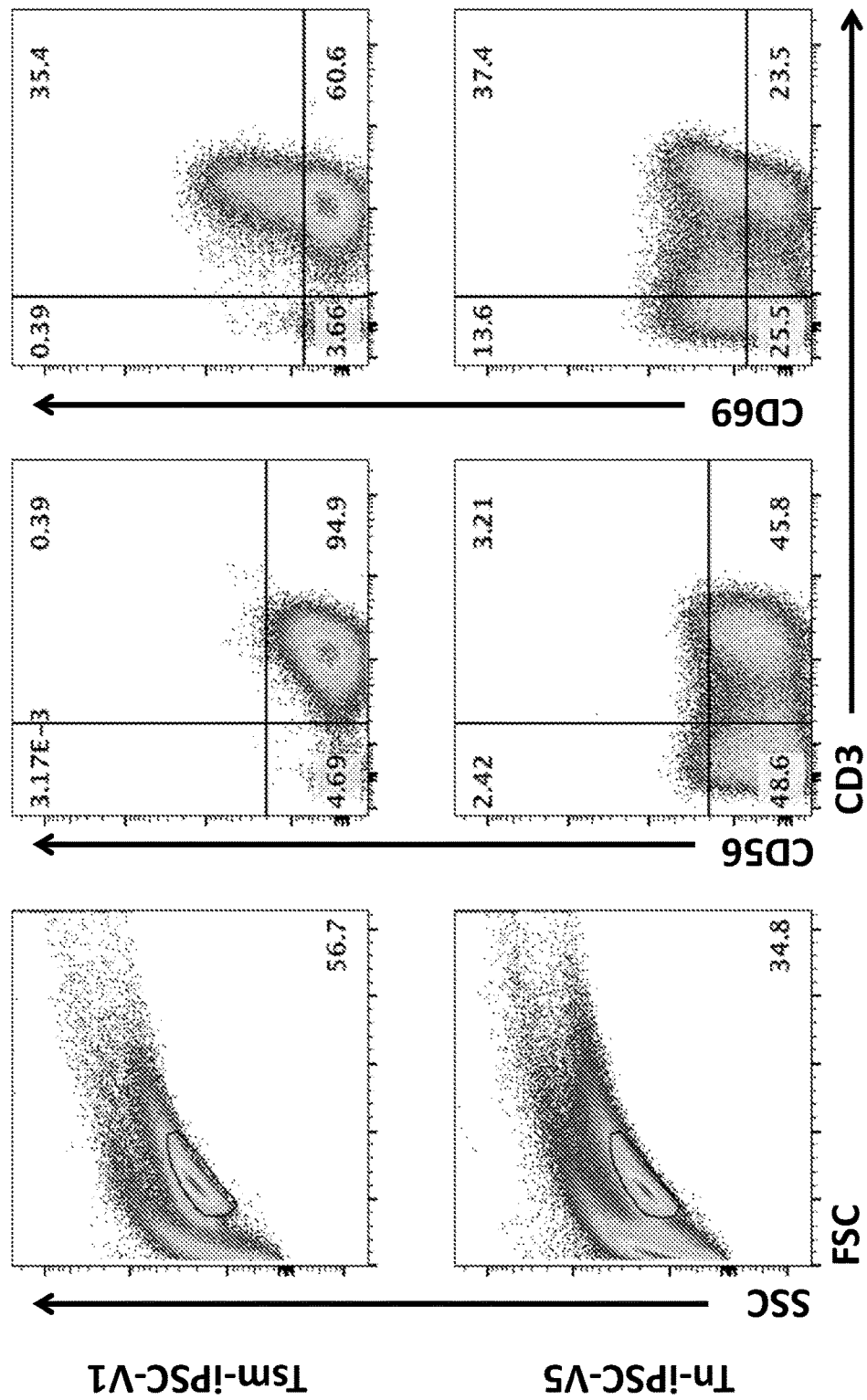
FIG. 15C. T-iPSC-derived cytotoxic T cells show expression of activated T cell marker CD69 but not NK marker CD56 at day 22 of differentiation.
Figure 16A:
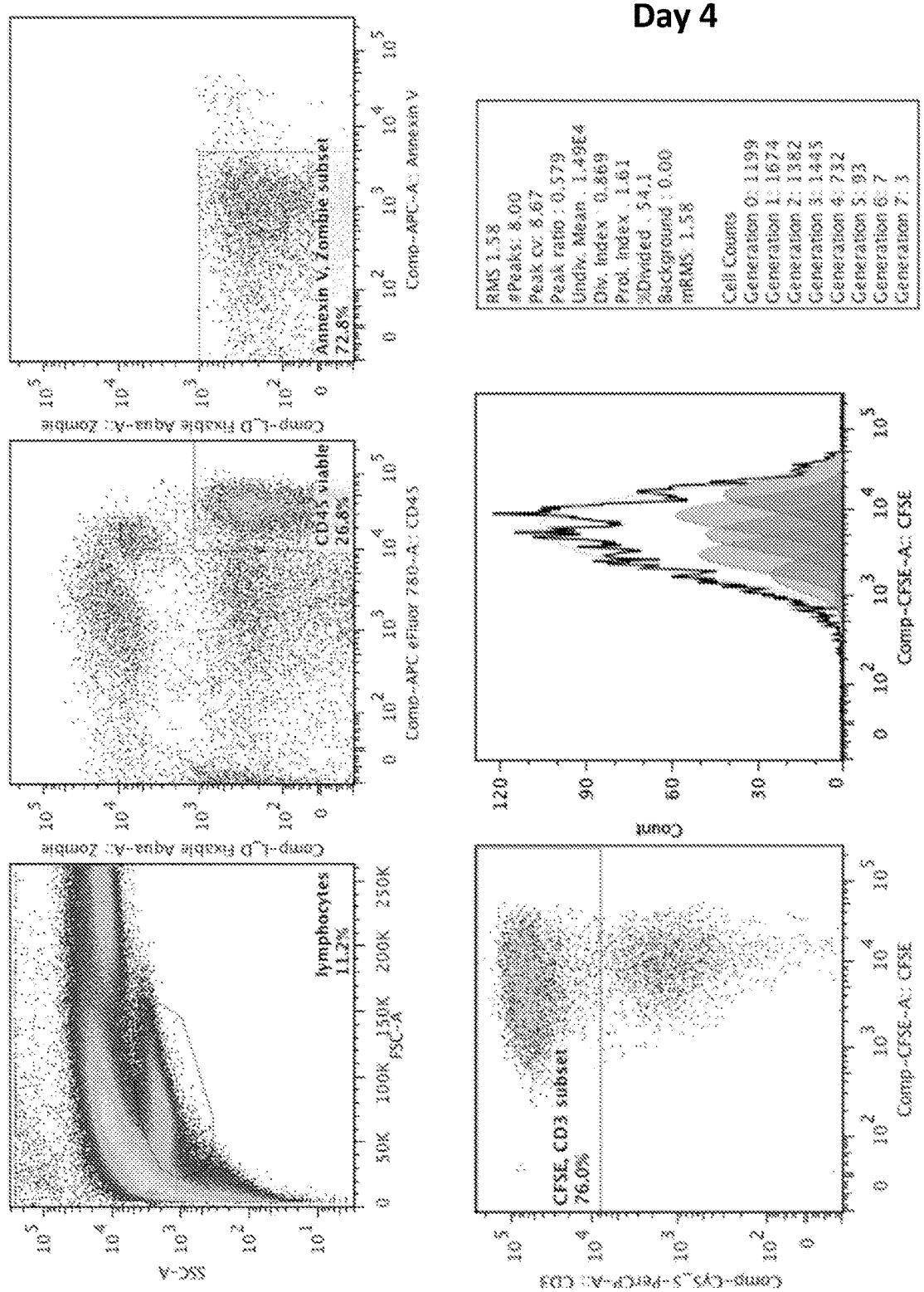
FIG. 16(A-D) shows exemplary CD3/CD28 monoclonal antibody-mediated T cell proliferation and expansion. T-iPSC-derived T cells were cultured in presence of T differentiation medium containing IL-7 and Flt3L cytokines and were stimulated with anti-CD3/28 monoclonal antibodies conjugated to beads at 3:1 ratio to the CD3 positive cells, in the presence of IL-2 cytokine. CF SE dye labeling was performed to analyze cell proliferation. Flow cytometric analysis was performed on day 4 (FIG. 16A) and day 10 (FIG. 16B). L-D fixable aqua-Zombie dye and Annexin V staining was performed to exclude dead cells.
FIG. 16C. Proliferation Index.
FIG. 16D. Division Index.
Figure 16B:
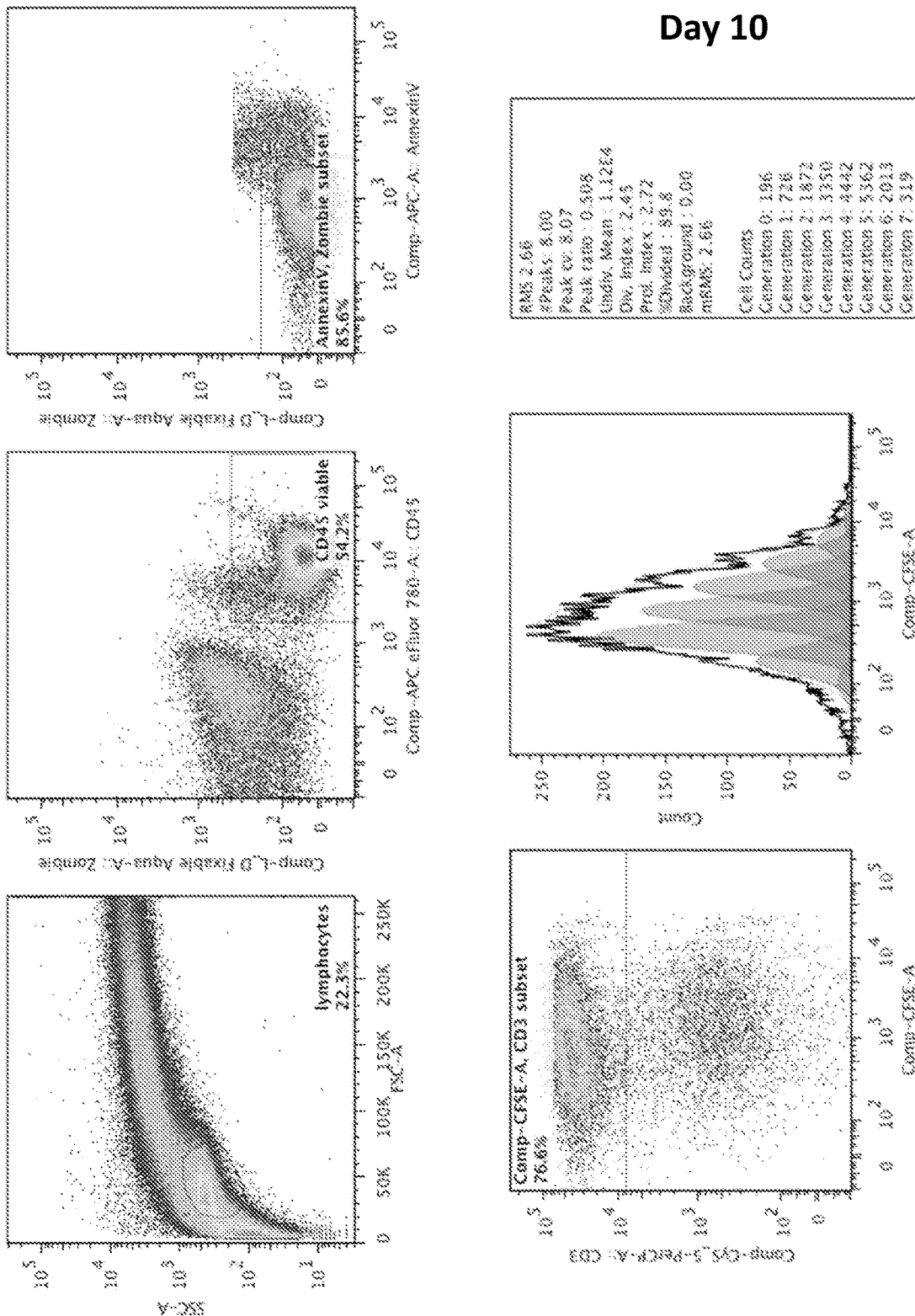
Figure 16C:
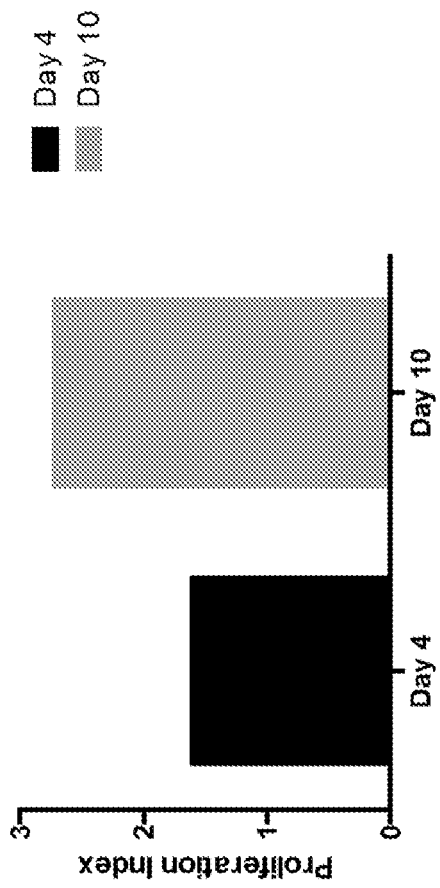
Figure 16D:
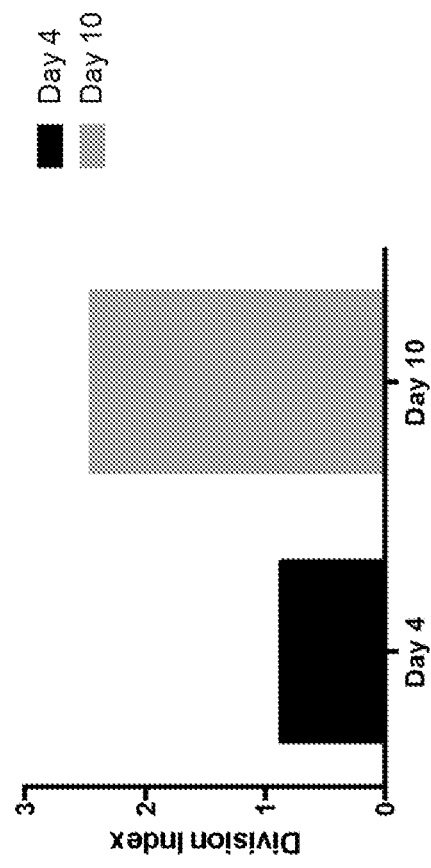

FIGS. 8-10 show comparative time kinetics for T cell development between Tn and Tsm-iPSCs derived T cells (a mixture of DN (T progenitors) and some CD8a positive T cells). Examining CD45+ viable cell development kinetics it shows While Tsm-iPSC-derived T progenitor cells demonstrate an ongoing increase in CD45+ lymphoid cell population, Tn-iPSC derived cells demonstrate an increase in CD45+ lymphoid cells up to day 23 but then a drop in absolute numbers is observed, indicating T stem cell memory derived cells have a better proliferative capacity. Similarly an increase in Tsm-iPSC derived CD3+/TCRαβ+ and CD8α+ T cells was observed throughout the time points analyzed.

Figure 21:
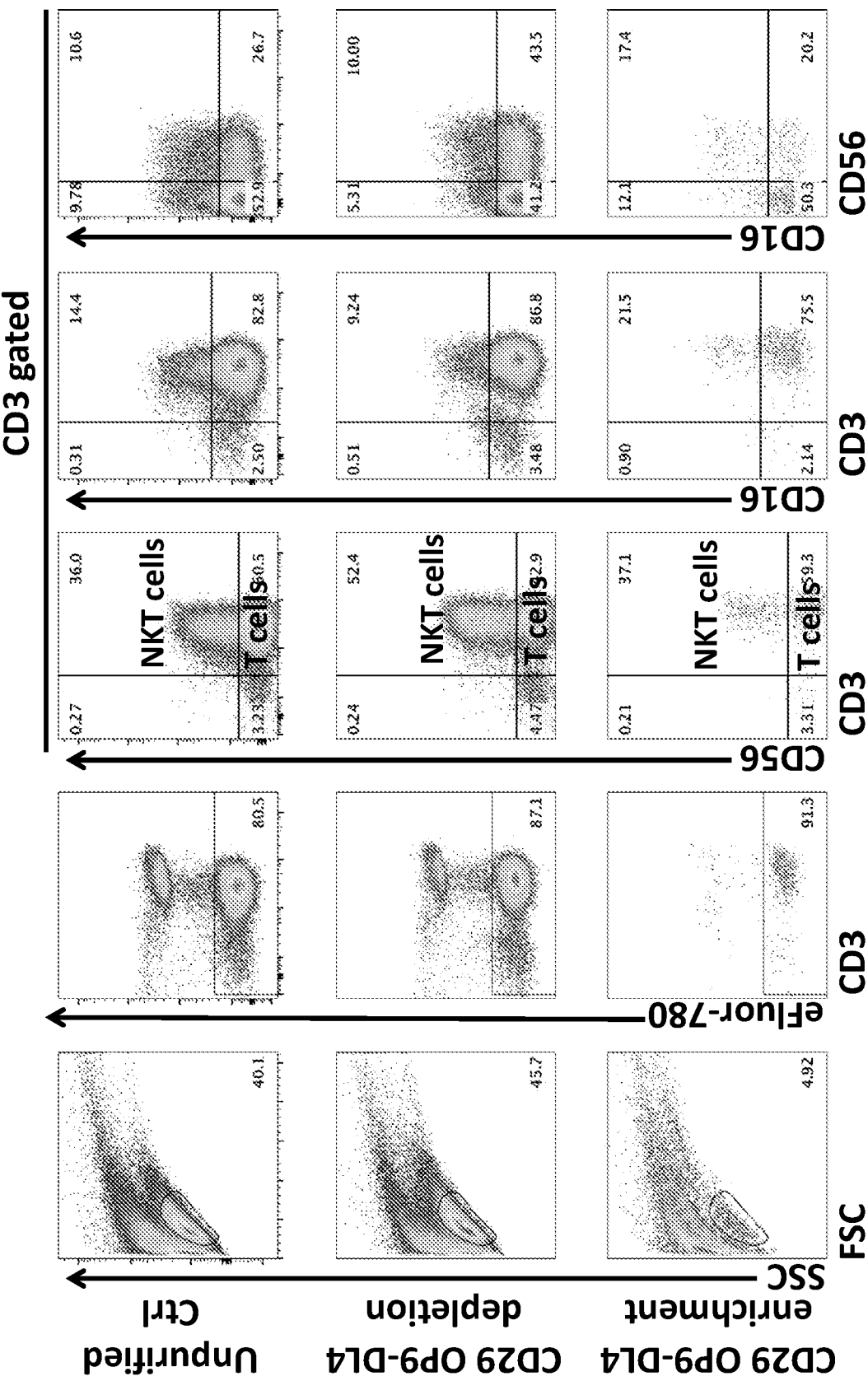
FIG. 21 shows exemplary flow analysis of in-vitro differentiated NKT cells at day 23. T-iPSC-derived EBs were dissociated at day 9 of differentiation, CD34$^+$ cells were enriched using CD34 EASYSEP. CD34$^+$ hematopoietic progenitors were co-cultured with OP9-DL4 stromal cells for 14 additional days. At day 23, CD3$^+$ viable cells were gated for further analysis. CD56$^+$CD3$^+$ cells are NKT cells whereas CD3$^+$CD56$^-$ cells are T cells. CD16 serves as an additional marker for NKT cells.
Figure 22:
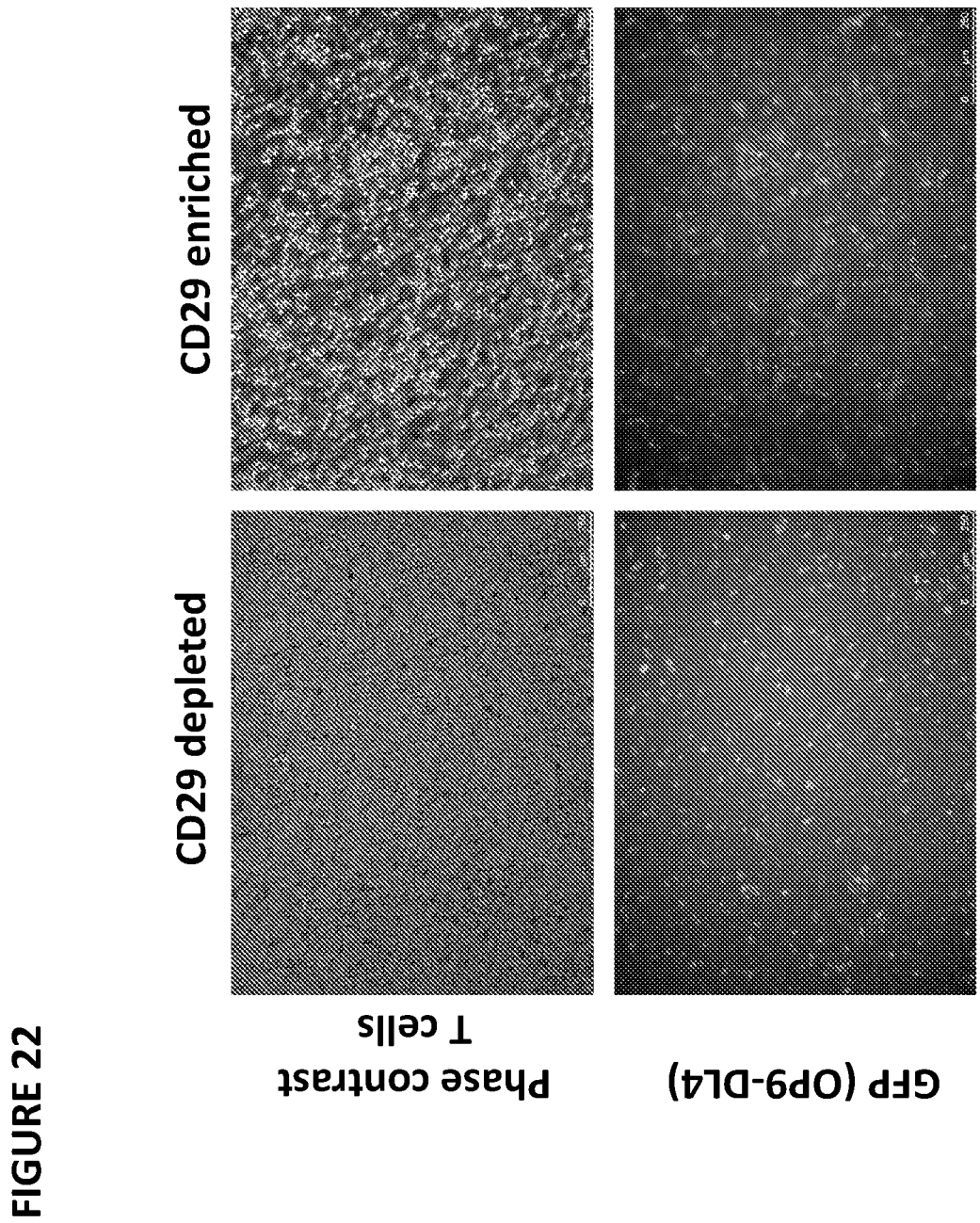
FIG. 22 shows in-vitro differentiated NKT cells demonstrate cytotoxic function. T-iPSC-derived EBs were dissociated at day 9 of differentiation and enriched for CD34$^+$ cells using CD34 EASYSEP. These CD34$^+$ hematopoietic progenitors were co-cultured with OP9-DL4 stromal cells (which express CD29 surface marker) for 7 additional days. At day 16 (9 days of EB differentiation+7 days of OP9-DL4 co-culture), the T progenitors were separated using anti-CD29 biotin conjugated beads (MCA2298B, AbD Serotech, Kidlington, UK) using EASYSEP biotin positive selection kit (#18559, Stem Cell Technologies, Vancouver, British Columbia). Cells that did not bind to the CD29 antibody termed as a "CD29 depleted fraction" and cells that bound to the CD29 antibody termed as a "CD29 enriched fraction." Each fraction was plated on GFP-expressing OP9-DL4 cells. 24 hours later, the viability of the GFP-expressing OP9-DL4 cells was assessed by microscopy.
Figure 23:
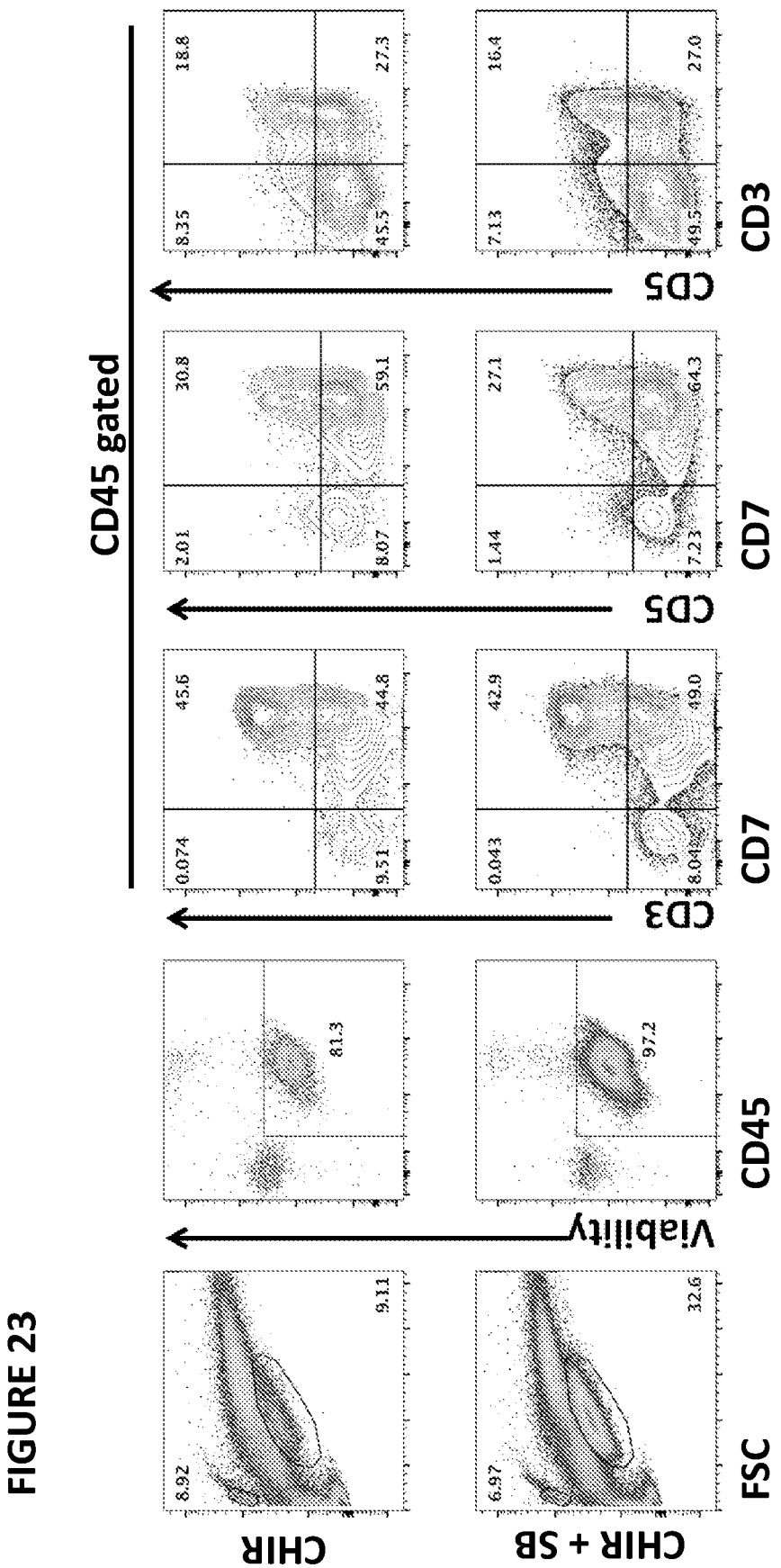
FIG. 23 shows exemplary results of culture with CHIR99021 versus CHIR99021 and SB431542, as measured at day 16. Tsm-iPSCs were subjected to 9 days EB differentiation followed by 7 additional days of OP9-DL4 co-culture. During day 1.75 to day 3 of EB differentiation, cultures were treated with CHIR99021 or CHIR99021 and SB431542. Phenotypic comparison using the flow analysis for the indicated markers was performed at day 16 (9 days EB+7 days OP9-DL4 co-culture).
Figure 24A:
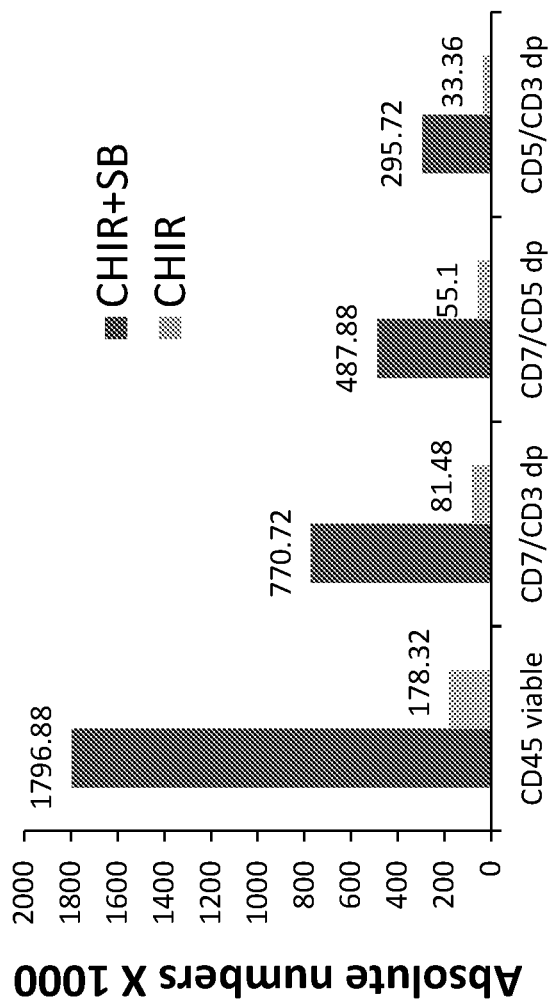
FIG. 24A shows absolute numbers of Tsm-iPSCs-derived aggregates were increased with treatment with CHIR99021 and SB431542 relative to CHIR99021 alone and FIG. 24B shows an approximately 9 to 10-fold increase in absolute numbers of Tsm-iPSCs-derived aggregates was observed with treatment with CHIR99021 and SB431542 relative to CHIR99021 alone.
Figure 24B:
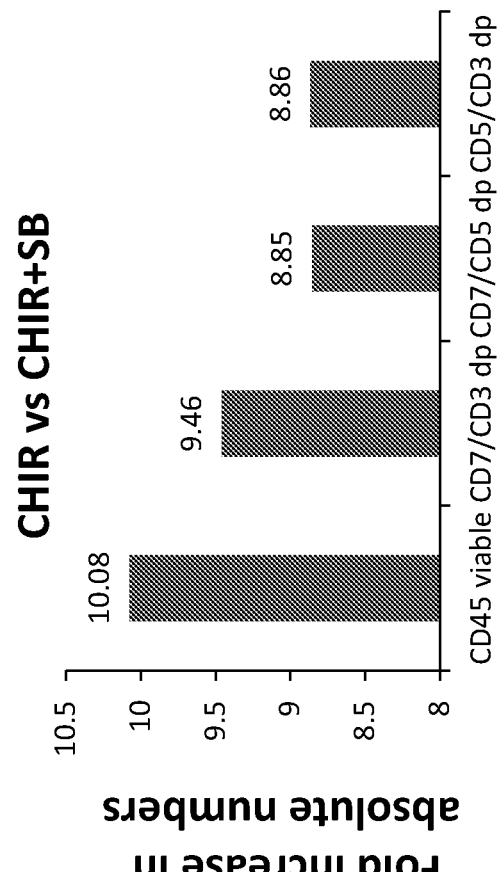
Figure 25:
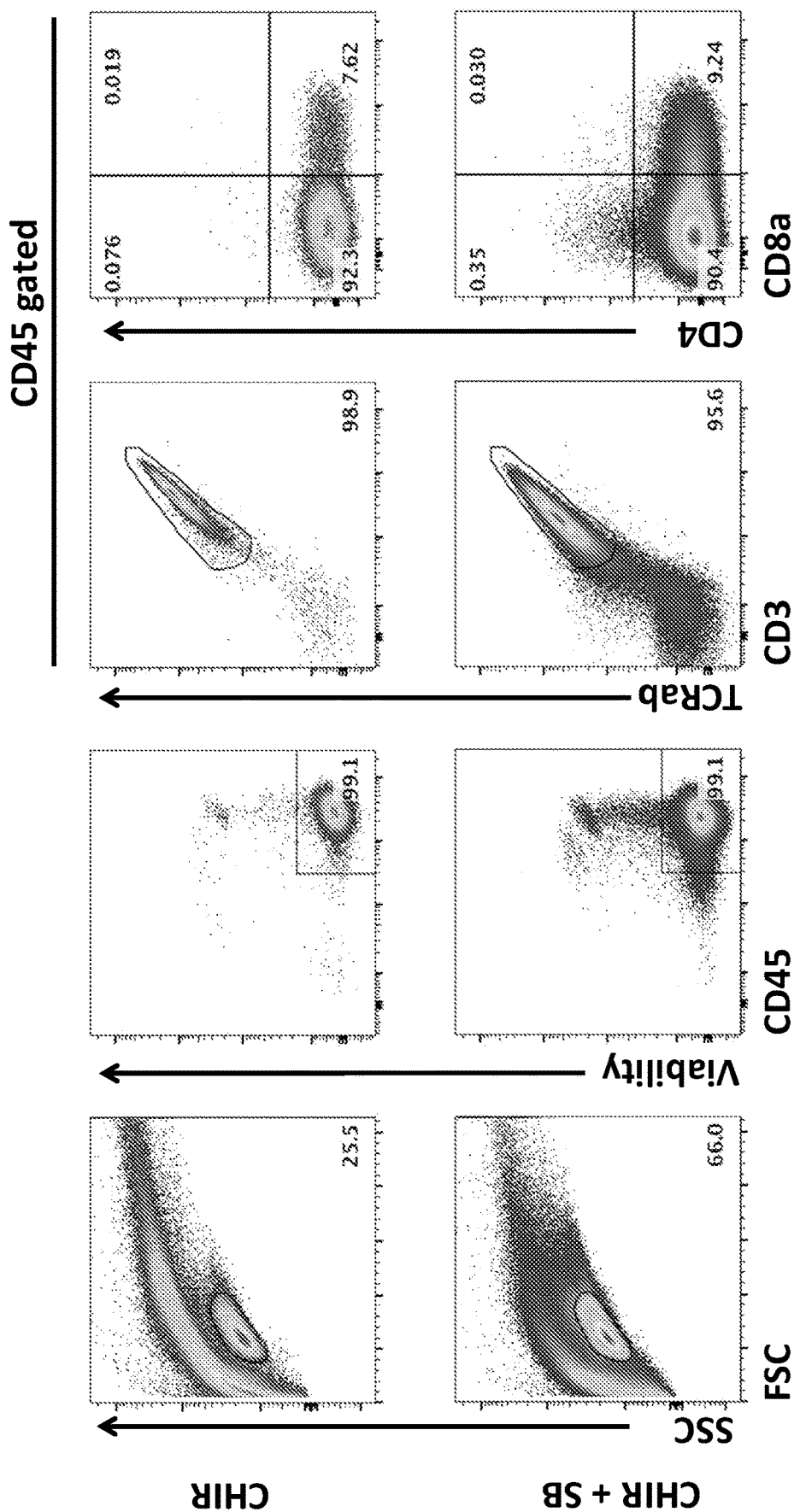
FIG. 25 shows exemplary results of culture with CHIR99021 versus CHIR99021 and SB431542, as measured at day 23. Tsm-iPSCs were treated with CHIR99021 or CHIR99021 and SB431542 from day 1.75 to day 3 of EB differentiation. EBs were dissociated at day 9 of differentiation and CD34$^+$ cells were enriched using CD34 EASY- SEP then co-cultured with OP9-DL4 stromal cells for 14 additional days. Flow cytometric analysis was performed on day 23 (9 days EB+14 days OP9-DL4 co-culture), the desired lymphocyte populations were gated stringently, and viable CD45 positive cells were analyzed for the indicated markers.
Figure 26A:
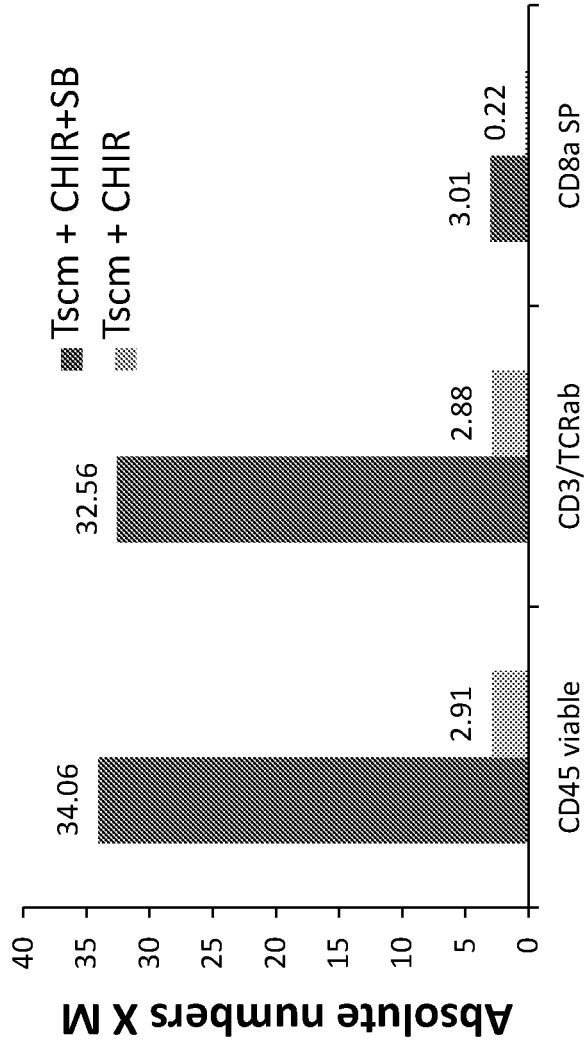
FIG. 26A shows absolute numbers of Tsm-iPSC-derived aggregates were increased with treatment with CHIR99021 and SB431542 relative to CHIR99021 alone and FIG. 26B shows the approximately 11 to 14-fold increase in absolute numbers of Tsm-iPSC-derived aggregates that was observed with treatment with CHIR99021 and SB431542 relative to CHIR99021 alone.
Figure 26B:
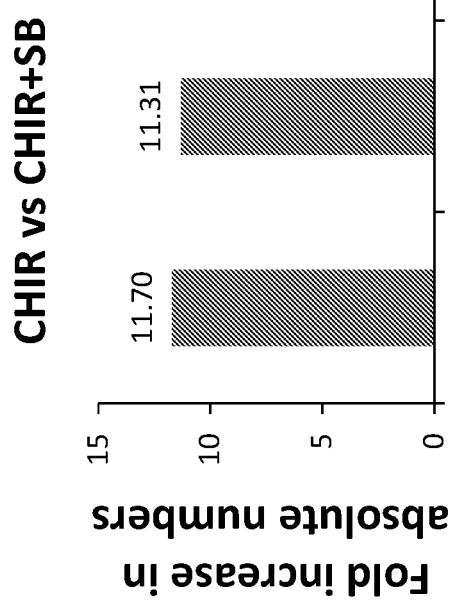
Figure 27A:
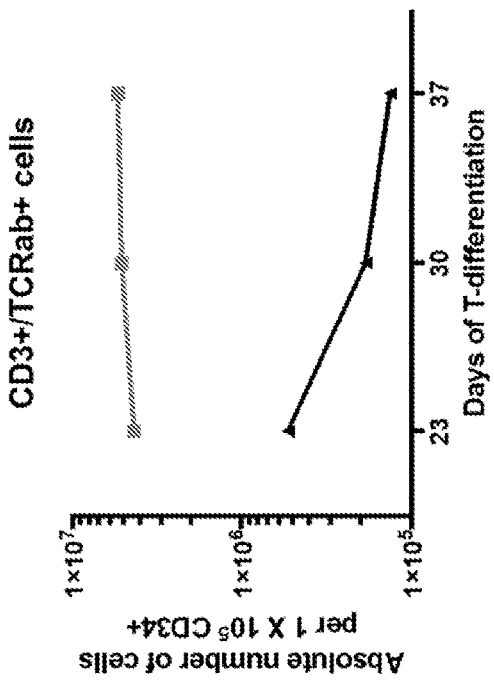
FIG. 27(A-C) shows exemplary kinetics of CHIR99021 versus CHIR99021 and SB431542 treatment on in-vitro T cell development. Tsm-iPSCs were treated with CHIR99021 or CHIR99021 and SB431542 from day 1.75 to day 3 of EB differentiation. EBs were dissociated at day 9 of differentiation and CD34$^+$ cells were enriched using CD34 EASY-SEP. The resulting CD34$^+$ hematopoietic progenitors were co-cultured with OP9-DL4 stromal cells for number of days indicated on the X-axis. Absolute cell numbers comparison between CHIR99021 and CHIR99021 and SB431542 treatment shows increased numbers of viable CD45 positive cells (FIG. 27A), CD3/TCRαβ double positive cells (FIG. 27B), and CD8a (alpha) single positive cells (FIG. 27C) for cells treated with CHIR99021 and SB431542 relative to CHIR99021 alone.
Figure 27B:
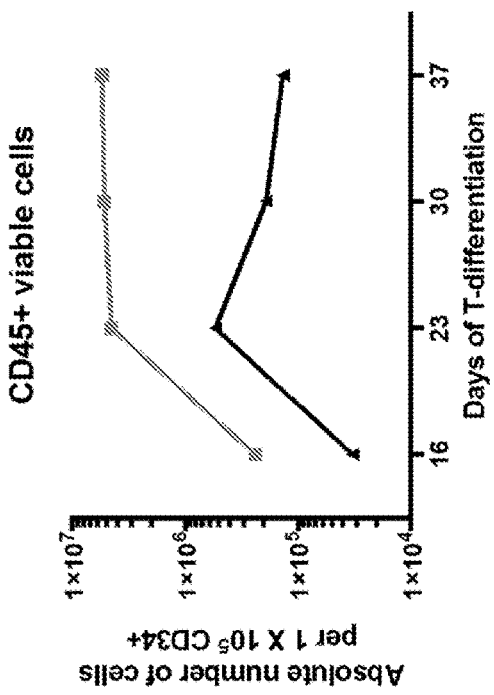
Figure 27C:
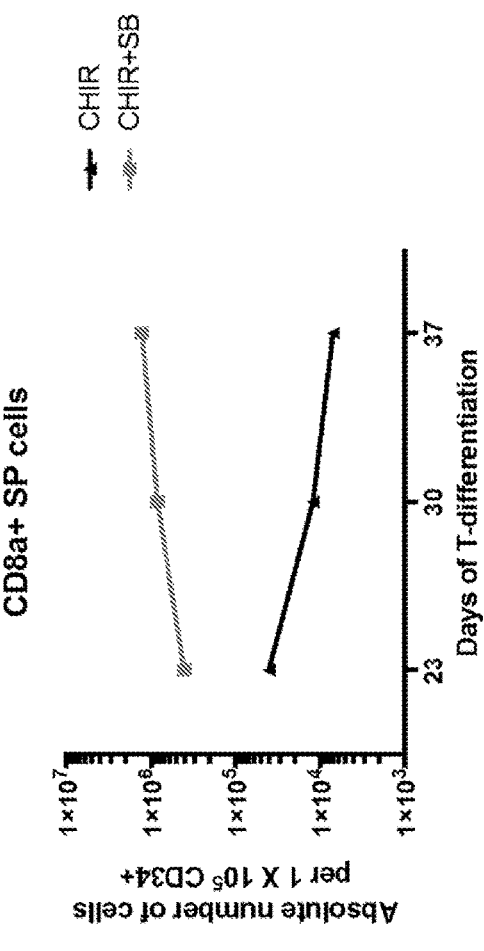

FIG. 21 examines the effect of cell culture conditions on the production of cells exhibiting an NKT cell phenotype. Lack of OP9-DL4 leads to increased NKT phenotype, indicating lack of appropriate Notch signaling promotes an NKT phenotype. FIG. 22 shows the effects of CD29+ OP9-DL4 enrichment and depletion. OP9-DL4 depleted NKT cells. When plated on freshly coated OP9-DL4 cells, OP9-DL4 depleted NKT cells aggressively killed the newly coated OP9-DL4, whereas the OP9-DL4 enriched T/NKT fraction showed no destruction of freshly coated OP9-DL4 stroma.

Moreover, different T cell phenotypes can be achieved including cells that demonstrate different development time points. For example, by day 23 CD3+ TCRαβ+CD8a+CD56+ (NKT cell); CD3+ TCRαβ+CD8a+CD56+CD16+ (NKT cell); CD3+ TCRαβ+CD8a+ (T cell); or CD3+ TCRαβ+ CD4−CD8a− (T cell) phenotypes were observed.

Differentiation of an iPSC into a T Cell Including a T Cell of a T Cell Subset

This disclosure further provides T cells (including a T cell of a T cell subset) differentiated from an iPSC and methods for differentiating a T cell (including a T cell of a T cell subset) from an iPSC. The iPSC includes a T-iPSCs and/or an iPSC derived from a T cell subset. The IPSC derived from a T cell subset can include, for example, a Tn-iPSC, a T central memory cell-iPSC, a T effector-iPSC, a T effector/memory-iPSC, a T effector/memory/CD45RA+-iPSC, an NKT-iPSC, a T stem memory like-iPSC and/or a Tsm-iPSC.

In some embodiments, the T cell including, for example, a T cell of a T cell subset, is derived from a T progenitor cell, derived as described above from an iPSC. The T cell of a T cell subset can include, for example, a stem memory T cell (Tsm), a T stem memory-like cell, a T central memory cell, a T effector cell, a T effector/memory cell, a T effector/memory/CD45RA+ cell, a T exhausted cell, an NKT cell, and/or a naïve T cell. In some embodiments, the T cell of a T cell subset preferably includes a Tsm. In some embodiments, the T cell of a T cell subset preferably includes an NKT cell.

In some embodiments, a T stem memory cell is defined as a cell that is CD3+ and CD8+ and expresses at least one of CD45RA, CD62L, CCR7, CD95, and TCRα/β. In some embodiments, a T stem memory cell preferably does not express CD4 and/or CD34. In some embodiments, a T stem memory cell is defined as a cell that is CD3+, CD8+, CD45RA+, CD62L+, CCR7+, CD95+, TCRα/β+, and CD34−. In some embodiments, a T stem memory cell is defined as a cell that is CD3+, CD8+, CD45RA+, CD62L+, CCR7+, and CD95+. In some embodiments, a mature T stem memory cell is defined as a cell that is CD3+, CD8+, CD45RA+, CD45RO−, CD62L+, CCR7+, CD95+, CD27+, CD28+, and IL7Rα+.

In some embodiments, an NKT cell is defined as a cell that is CD56+ and/or CD16+ and expresses at least one of CD3, CD8, TCRα/β, CD1d, CD160, CD161, CD94, CD69, TCR Vα24Jα18, and PLZF.

In some embodiments, a cell undergoing differentiation to the T cell of a T cell subset preferably includes a T progenitor cell. In some embodiments, the cell undergoing differentiation includes a T progenitor cell derived from an IPSC derived from a T cell subset preferably includes, for example, a Tn-iPSC or a Tsm-iPSC, as described above. In some embodiments, the cell undergoing differentiation can be a CD45+ cell. In some embodiments, a population of cells including the cell undergoing differentiation can be enriched for CD45+ cells. In some embodiments, the population of cells can be a clonal population.

In some embodiments, the cell undergoing differentiation can be stimulated in media including at least one of stem cell factor (SCF), IL-7, FMS-like tyrosine kinase 3 ligand (Flt3L), IL-15, IL-21, IL-2, a Glycogen synthase kinase (GSK) 3 inhibitor, an ADAM17 inhibitor, and an AKT inhibitor. In some embodiments, the GSK3 inhibitor can include at least one of TWS119, CHIR99021, CHIR-98014, LY2090314, BIO, IM-12, 3F8, A 1070722, CHIR 99021 trihydrochloride, L803-mts, SB 216763, SB 415286, and TC-G 24. In some embodiments, the AKT-1/2 inhibitor can include at least one of Akt Inhibitor VIII, Isozyme-Selective, Akti-1/2, MK-2206 2HCl, Perifosine (KRX-0401), GSK690693, Ipatasertib (GDC-0068), AZD5363, AT7867, Afuresertib (GSK2110183), and AT13148. In some embodiments, the ADAM17 inhibitor can include at least one of Incyte INCB003619, TAPI-0, TAPI-1, and Batimastat (BB-94), In some embodiments, the cell can be treated with fresh media and/or additional cytokines one or more times during culture of the cells.

In some embodiments, the cell undergoing differentiation can be stimulated via at least one of CD3 and CD28. In some embodiments, the cell undergoing differentiation can preferably be stimulated via both CD3 and CD28. In some embodiments, the cell undergoing differentiation can be contacted with antibodies to CD3 and/or CD28. In some embodiments, the cell may be contacted with ligands of CD3 and/or CD28. In some embodiments, the cell may be contacted with agonists of CD3 and/or CD28. In some embodiments, the antibody, ligand, and/or agonist can be conjugated to a microbead.

In some embodiments, the cell undergoing differentiation that is stimulated via at least one of CD3 and CD28 is cultured in α-MEM and/or X-vivo media. In some embodiments, the cell can be stimulated multiple times with the antibodies.

In some embodiments, the cell undergoing differentiation can be treated with an inhibitor of mTOR including, for example, rapamycin and/or its analogs.

Engineering CAR- or TCR-Expressing iPSCs and T Cells

This disclosure also provides a chimeric antigen receptor (CAR)-expressing or T cell receptor (TCR)-expressing iPSC, a CAR- or TCR-expressing human T cell. In some embodiments, the CAR- or TCR-expressing T cell is preferably a T stem memory (Tsm) cell and/or an NKT cell. This disclosure further provides methods to engineer the chimeric antigen receptor (CAR)-expressing or T cell receptor (TCR)-expressing iPSC and the CAR- or TCR-expressing T cell.

In some embodiments, an iPSC and/or a T cell derived from an iPSC can be genetically modified with a CAR, including, for example, a dimerization activated receptor inducible chimeric antigen receptor (DARIC). In some embodiments, the T cell derived from an iPSC can include a T cell of a T cell subset. In some embodiments, the T cell subset preferably includes a T stem memory cell, a T central memory cell, a T effector cell, a T effector/memory cell, and/or a T effector/memory/CD45RA+ cell. In some embodiments, a CAR-modified iPSC can be differentiated to form a T cell including a T cell of a T cell subset. In some embodiments, the T cell subset preferably includes a T stem memory cell, a T central memory cells, a T effector cell, a T effector/memory cell, a Teffector/memory/CD45RA+ cells, and/or an NKT cell. In some embodiments, the T cell that is generated from a CAR- or TCR-modified iPSC can be induced to turn on or off immune responses. In some embodiments, the CAR- or TCR-expressing T cell is self-renewable and can persist long-term in vivo.

The CAR- or TCR-expressing cell can express any suitable CAR or TCR. For example, in some embodiments, the CAR-expressing cell expresses a tumor-directed CAR (Jensen et al., *Current Opinion in Immunology* 2015, 33:9-15; van der Stegen et al., Nature Reviews Drug Discovery 14, 499-509 (2015)). In some embodiments, the CAR expressing cell expresses CD19-directed CAR. In some embodiments, the CAR-expressing cell expresses an anti-human CD19SFv CAR. In some embodiments, the TCR-expressing cell can express a tumor-directed TCR. In some embodiments, the TCR is preferably a non-endogenous and/or recombinant TCR.

The CAR or TCR may be introduced into an iPSC or a T cell (including a T cell of a T cell subset) using any acceptable method. In some embodiments, the CAR or TCR may be introduced using a viral or non-viral vector that stably integrates a CAR into a chromosome and/or electroporation, including, for example, microelectroporation. In some embodiments, the vector can include a transposable element including, for example, a piggyBac (PB), Sleeping Beauty, and/or Tol2. In some embodiments, the vector can be targeted using a sequence-specific nuclease and/or system including, for example, Zinc finger nuclease (ZFN), a transcriptional activator-like effector nuclease (TALEN), and a two-component clustered regularly interspaced short palindromic repeat (CRISPR) system (e.g., a CRISPR-CRISPR-associated nuclease 9 (Cas9) system).

In some embodiments, the CAR or TCR may be introduced to an iPSC. The CAR or TCR may be introduced at any suitable time into a T-iPSC including a T-IPSC derived from a T cell subset. In some embodiments, the CAR or TCR may is preferably introduced to an iPSC and then the iPSC is subsequently differentiated into a T cell (including a T cell of a T cell subset).

Since Tsm-iPSCs and Tn-iPSC have undergone T cell receptor (TCR) rearrangement and express a TCR/CD3 complex (FIG. 8), in some embodiments, an iPSC, a T cell derived from an iPSC can be genetically modified to diminish or eliminate endogenous TCR signaling. In some embodiments, an iPSC or a T cell derived from an iPSC including, for example, a T stem memory cell and/or an NKT cell derived from an iPSC can be genetically modified to be TCRα$^-$, TCRβ$^-$, and/or TCRα/β$^-$. In some embodiments, the T Cell Receptor alpha constant (TRAC) can be knocked out using gene editing nuclease technology in an iPSC, and/or a T stem memory cell and/or an NKT cell derived from an iPSC. In some embodiments miRNAs can be used to regulate signaling (Papapetrou et al. *J. Clin. Investigation.* 2009; 119(1):157-68).

Administration Cells

This disclosure further describes a method of administering any of the cells described herein including, for example, a T cell of a T cell subset by adoptive transfer. In some embodiments, the T cell to be administered includes a Tsm cell, a T central memory cell, a T effector, a T effector/memory, a T effector/memory/CD45RA+ cells, and/or an NKT cell. In some embodiments, the T cell to be administered preferably includes a Tsm cell.

In some embodiments, wherein a T cell, including a T cell of a T cell subset was derived from a subject in need of treatment and used to derive a T-iPSC, the T-iPSC can be administered to the subject. In some embodiments, the T-iPSC is preferably derived from a T cell of a T cell subset. In some embodiments, the T-iPSC can preferably include a Tn-iPSC, a T central memory cell-iPSC, aT effector-IPSC, a T effector/memory-IPSCs, a T effector/memory/CD45RA+ iPSC, a Tsm-iPSC and/or an NKT-iPSC.

In some embodiments, a T cell, including a T cell of a T cell subset differentiated from a clonal population of a T-iPSC can be administered to a subject. In some embodiments, the T-iPSC is preferably derived from a T cell of a T cell subset. In some embodiments, the T cell can include a Tsm cell, a Tcentral memory cell, a Teffector cell, a Teffector/memory cell, a Teffector/memory/CD45RA+ cell, and/or a NKT cell differentiated from a T-iPSC.

In some embodiments, the T cell, including a T cell of a T cell subset differentiated from a T-iPSC can be administered to a subject. In some embodiments, the T cell can be derived from a clonal population of T-IPSCs. In some embodiments, the T-iPSC or the clonal population of T-iPSC preferably includes a Tn-iPSC, a Tcentral memory cell-iPSC, a Teffector-iPSC, a Teffector/memory-iPSC, a Teffector/memory/CD45RA+ iPSC, an NKT-iPSC and/or a Tsm-iPSC. In some embodiments the T cell administered to the subject preferably includes a Tsm.

Without wishing to be bound by theory, it is believed that an iPSC generated from a Tn, a Tsm, or a T central memory cell can provide a virtually limitless source of long-lasting Tsm cells for adoptive therapy in chemotherapy treated patients with low Tsm frequencies. In some embodiments, and as further described herein, the Tsm cell used for adoptive therapy can be a CAR-Tsm cell. Additionally, in some embodiments, T effector cells, T effector/memory, T effector/memory/CD45RA+ cells, and/or NKT cells can be administered individually or in combination with a Tsm and can provide immediate anti-pathogen and anti-tumor responses. In some embodiments, the T effector cells, T effector/memory, T effector/memory/CD45RA+ cells, and/or NKT cells can be derived from a T-iSPC. In some embodiments, the T effector cells, T effector/memory, T effector/memory/CD45RA+ cells, and/or NKT cells can be administered in combination with a Tsm and each of the cells can be derived from the same T-iSPC.

In some embodiments, a T cell, including a T cell of a T cell subset from an allogenic source can be administered to a subject. For example, a Tsm, a Tn, a T central memory cell, a T effector, a T effector/memory, a T effector/memory/CD45RA+, and/or a NKT cell can be administered. The T cell can be differentiated from a T-iPSC, including a T-iPSC derived from a T cell subset. For example, the T-iPSC can include a Tn-iPSC, a T central memory cell-iPSC, a T effector-iPSC, a T effector/memory-iPSC, a T effector/memory/CD45RA+ iPSC, a NKT-iPSC, and/or a Tsm-iPSC.

In some embodiments, the cells may be administered to treat a malignant disease. In some embodiments, the malignant disease is characterized by target cells to which the CAR or TCR can bind. In some embodiments, the cells may be administered to treat an autoimmune disease. In some embodiments, the autoimmune disease is characterized by target cells to which the CAR or TCR can bind.

The cell can be administered to a subject alone or in a pharmaceutical composition that includes the active agent and a pharmaceutically acceptable carrier. The cell can be administered to a patient, preferably a mammal, and more preferably a human, in an amount effective to produce the desired effect. The cell can be administered in a variety of routes, including, for example, intravenously, intratumorally, intraarterially, transdermally, via local delivery by catheter or stent, via a needle or other device for intratumoral injection, subcutaneously, etc. The cell can be administered once or multiple times. A physician having ordinary skill in the art can determine and prescribe the effective amount of cells and, optionally, the pharmaceutical composition required.

Methods of Treatment

In one aspect, any of the cells described herein can be used to treat or prevent a virus, a cancer, or a precancerous condition, in a subject. In a further aspect, any of the cells described herein can be administered to inhibit the growth of a tumor in a subject. In some embodiments, the tumor can include a solid tumor.

Any of the cells described herein including, for example, a T cell of a T cell subset (e.g., a Tsm, a T stem memory like cell, a T naïve cell, a T central memory cells, a T effector, a T effector/memory, a T effector/memory/CD45RA+ cells, a T exhausted cell, and/or an NKT cell) and/or a CAR-expressing T cell can be administered to a subject before, during, and/or after other treatments. Such combination therapy can involve the administration of a cell before, during and/or after the use of other anti-cancer and/or anti-viral agents and/or autoimmune disease agents including, for example, a cytokine; a chemokine; a therapeutic antibody including, for example, a high affinity anti-CMV IgG antibody; an NK cell receptor ligand, including, for example, BiKE or TRiKE; an adjuvant; an antioxidant; a chemotherapeutic agent; agents (drugs, antibodies, proteins, cells) that are used to treat autoimmune diseases; and/or radiation. The administration or preparation can be separated in time from the administration of other anti-cancer agents and/or anti-viral agents and/or autoimmune therapies by hours, days, or even weeks. Additionally or alternatively, the administration or preparation can be combined with other biologically active agents, cells or modalities such as, but not limited to, an antineoplastic agent, and non-drug therapies, such as, but not limited to, surgery.

EXEMPLARY EMBODIMENTS

Exemplary iPSC, and T Cell Embodiments

Embodiment 1

An induced pluripotent stem cell (iPSC) derived from a T cell.

Embodiment 2

The induced pluripotent stem cell of Embodiment 1 wherein the iPSC is derived from a T cell of a T cell subset.

Embodiment 3

The induced pluripotent stem cell of Embodiment 2 wherein the T cell of a T cell subset comprises at least one of a stem memory T cell, a stem memory-like T cell, a naïve T cell, an effector T cell, an effector/memory T cell, an effector/memory/CD45RA+ T cell, a central memory T cell, an exhausted T cell, and a Natural Killer T cell.

Embodiment 4

The induced pluripotent stem cell of any of Embodiments 1 to 3, wherein the induced pluripotent stem cell expresses a chimeric antigen receptor.

Embodiment 5

The induced pluripotent stem cell of any of Embodiments 1 to 3, wherein the induced pluripotent stem cell expresses a T cell receptor.

Embodiment 6

The induced pluripotent stem cell of any of Embodiments 1 to 5, wherein the T cell comprises a human T cell.

Embodiment 7

A T cell, wherein the T cell is derived from the induced pluripotent stem cell of any of Embodiments 1 to 6.

Embodiment 8

The T cell of Embodiment 7, wherein the T cell comprises at least one of a stem memory T cell, a stem memory-like T cell, a naïve T cell, an effector T cell, an effector/memory T cell, an effector/memory/CD45RA+ T cell, a central memory T cell, an exhausted T cell, and a Natural Killer T cell.

Embodiment 9

The T cell of Embodiment 7, wherein the T cell comprises a stem memory T cell.

Embodiment 10

The T cell of Embodiment 9, wherein the T cell further comprises at least one of a stem memory-like T cell, a naïve T cell, an effector T cell, an effector/memory T cell, an effector/memory/CD45RA+ T cell, a central memory T cell, an exhausted T cell, and a Natural Killer T cell.

EXEMPLARY METHOD EMBODIMENTS

Embodiment 1

A method comprising differentiating an induced pluripotent stem cell derived from a T cell of a T cell subset.

Embodiment 2

The method of Embodiment 1, wherein the induced pluripotent stem cell is derived from at least one of a stem memory T cell, a stem memory-like T cell, a naïve T cell, an effector T cell, an effector/memory T cell, an effector/memory/CD45RA+ T cell, a central memory T cell, an exhausted T cell, and a Natural Killer T cell.

Embodiment 3

The method of Embodiment 1 or 2, wherein the induced pluripotent stem cell is derived from a stem memory T cell, a central memory T cell, or a naïve T cell.

Embodiment 4

The method of any of Embodiments 1 to 3, wherein the method further comprises differentiating the induced pluripotent stem cell to a differentiated cell, wherein the differentiated cell comprises a T cell.

Embodiment 5

The method of Embodiment 4 wherein the differentiated cell comprises at least one of a stem memory T cell, a stem memory-like T cell, a naïve T cell, an effector T cell, an effector/memory T cell, an effector/memory/CD45RA+ T cell, a central memory T cell, an exhausted T cell, and a Natural Killer T cell.

Embodiment 6

The method of Embodiments 4 or 5, wherein the differentiated cell comprises a stem memory T cell.

Embodiment 7

The method of any of Embodiments 1 to 6, wherein the differentiated cell expresses CD3 and CD8 and at least one of CD45RA, CD62L, CCR7, CD95, TCRα/β, CD27, CD28, and IL-7Rα.

Embodiment 8

The method of any of Embodiments 1 to 7, wherein the differentiated cell does not express at least one of CD4, CD34, and CD45RO.

Embodiment 9

The method of any of Embodiments 1 to 8, wherein the method comprises forming embryoid bodies (EBs).

Embodiment 10

The method of any of Embodiments 1 to 9, wherein the method comprises treating the cell undergoing differentiation with a Wnt pathway activator.

Embodiment 11

The method of Embodiment 10, wherein the Wnt pathway activator comprises at least one of CHIR99021, CHIR-98014, LY2090314, BIO, IM-12, 3F8, A 1070722, trihydrochloride, L803-mts, SB 216763, SB 415286, TC-G 24, and TWS119.

Embodiment 12

The method of any of Embodiments 1 to 11, wherein the method comprises treating the cell undergoing differentiation with a TGFβ signaling inhibitor.

Embodiment 13

The method of Embodiment 12, wherein the TGFβ signaling inhibitor comprises at least one of SB431542 EW-7197, Galunisertib (LY2157299), LY2109761, SB525334, SD-208, SB505124, GW788388, and RepSox.

Embodiment 14

The method of any of Embodiments 1 to 13, wherein the method comprises culturing the cell undergoing differentiation in the presence of a Wnt pathway activator and a TGFβ signaling inhibitor.

Embodiment 15

The method of any of Embodiments 1 to 14, wherein the method comprises culturing the cell undergoing differentiation in the presence of at least one of a Wnt pathway activator and a TGFβ signaling inhibitor during embryoid body formation.

Embodiment 16

The method of any of Embodiments 1 to 15, wherein the method comprises culturing the cell in serum-free animal-product free (APEL) media.

Embodiment 17

The method of any of Embodiments 1 to 16, wherein the method comprises culturing the cell in the presence of at least one of basic fibroblast growth factor (bFGF) and bone morphogenetic protein (BMP)-4.

Embodiment 18

The method of any of Embodiments 1 to 17, wherein the method comprises culturing the cell in the presence of a hematopoietic cytokine.

Embodiment 19

The method of Embodiment 18, wherein a hematopoietic cytokine comprises at least one of stem cell factor (SCF), vascular endothelial growth factor (VEGF), FMS-like tyrosine kinase 3 ligand (Flt3L), and IL-3.

Embodiment 20

The method of any of Embodiments 1 to 19, wherein the method comprises culturing the cell undergoing differentiation on stromal cells expressing a Notch ligand or in media comprising a Notch ligand.

Embodiment 21

The method of Embodiment 20, where the stromal cells comprise at least one of OP9-DL4 and OP9-DL1.

Embodiment 22

The method of any of Embodiments 1 to 21, wherein the method comprises culturing the cell undergoing differentiation with at least one of stem cell factor (SCF), IL-7, and FMS-like tyrosine kinase 3 ligand (Flt3L).

Embodiment 23

The method of any of Embodiments 1 to 22, wherein the method comprises culturing the cell undergoing differentiation sequentially with media comprising at least one of basic fibroblast growth factor (bFGF) and bone morphogenetic protein (BMP)-4;
media comprising at least one of a Wnt pathway activator and a TGFβ signaling inhibitor;
media comprising at least one hematopoietic cytokine; and
media comprising at least one of stem cell factor (SCF), IL-7, and FMS-like tyrosine kinase 3 ligand (Flt3L).

Embodiment 24

The method of any of Embodiments 1 to 23, wherein the method comprises culturing the cell undergoing differentiation sequentially in
media comprising animal-product free medium (APEL) differentiation medium; and
media comprising a stromal cell expressing a Notch ligand or media comprising a soluble Notch ligand.

Embodiment 25

The method of Embodiment 24, wherein the APEL differentiation medium comprises basic fibroblast growth factor (bFGF).

Embodiment 26

The method of Embodiments 24 or 25, wherein the the APEL differentiation medium comprises at least one of a Wnt pathway activator, a TGFβ signaling inhibitor, and a hematopoietic cytokine.

Embodiment 27

The method of any of Embodiments 24 to 26, wherein the media comprising a stromal cell expressing a Notch ligand or media comprising a soluble Notch ligand further comprises at least one of stem cell factor (SCF), IL-7, and FMS-like tyrosine kinase 3 ligand (Flt3L).

Embodiment 28

The method of any of Embodiments 1 to 27, wherein the method comprises enriching a population for $CD34^+$ cells.

Embodiment 29

The method of any of Embodiments 1 to 28, wherein the induced pluripotent stem cell comprises a chimeric antigen receptor-expressing cell.

Embodiment 30

The method of any of Embodiments 1 to 29, wherein the induced pluripotent stem cell comprises a T cell receptor-expressing cell.

Embodiment 31

The method of any of Embodiments 1 to 30, wherein the induced pluripotent stem cell comprises a member of a clonal population.

Embodiment 32

The method of Embodiment 31, wherein the induced pluripotent stem cell comprises a member of a clonal population derived from one of the following clones: PT8-Tn-iPSC-V5, PT8-Tn-iPSC-V11, PT8-Tn-iPSC-V12, PT9-Tn-iPSC, PT10-Tn-iPSC, PT12-Tn-iPSC, PT13-Tn-iPSC, PT15-Tsm-iPSC-V1, PT32-Tsm-iPSC-V1, PT32-Tsm-iPSC-V3, PT33-Tsm-iPSC-V2, PT33-Tsm-iPSC-V10, PT34-Tsm-iPSC, PT35-Tn-1-iPSC, PT35-Tn-2-iPSC-V4, PT35-Tn-2-iPSC-V4, PT35-Tn-2-iPSC-V9, PT35-Tn-3-iPSC-V3.

Embodiment 33

The method of any of Embodiments 1 to 32 further comprising stimulating the cell undergoing differentiation via at least one of CD3 and CD28.

Embodiment 34

The method of Embodiment 33, wherein the method comprises stimulating the cell undergoing differentiation via CD3 and CD28.

Embodiment 35

The method of Embodiments 33 or 34 wherein stimulating the cell undergoing differentiation via at least one of CD3 and CD28 comprises using an antibody conjugated microbead.

Embodiment 36

The method of any of Embodiments 33 to 35, the method comprising simulating the cell undergoing differentiation in media comprising at least one of stem cell factor (SCF), IL-7, FMS-like tyrosine kinase 3 ligand (Flt3L), IL-15, IL-21, IL-2, a Glycogen synthase kinase 3 inhibitor and an AKT inhibitor.

Embodiment 37

The method of any of Embodiments 33 to 36 further comprising enriching a clonal population comprising the cell undergoing differentiation for cells expressing CD45.

EXEMPLARY CELL LINE EMBODIMENTS

Embodiment 1

An induced pluripotent stem cell line PT8-Tn-iPSC-V5.

Embodiment 2

An induced pluripotent stem cell line PT8-Tn-iPSC-V11.

Embodiment 3

An induced pluripotent stem cell line PT8-Tn-iPSC-V12.

Embodiment 4

An induced pluripotent stem cell line PT9-Tn-iPSC.

Embodiment 5

An induced pluripotent stem cell line PT10-Tn-iPSC.

Embodiment 6

An induced pluripotent stem cell line PT12-Tn-iPSC.

Embodiment 7

An induced pluripotent stem cell line PT13-Tn-iPSC.

Embodiment 8

An induced pluripotent stem cell line PT15-Tsm-iPSC-V1.

Embodiment 9

An induced pluripotent stem cell line PT32-Tsm-iPSC-V1.

Embodiment 10

An induced pluripotent stem cell line PT32-Tsm-iPSC-V3.

Embodiment 11

An induced pluripotent stem cell line PT33-Tsm-iPSC-V2.

Embodiment 12

An induced pluripotent stem cell line PT33-Tsm-iPSC-V10.

Embodiment 13

An induced pluripotent stem cell line PT34-Tsm-iPSC.

Embodiment 14

An induced pluripotent stem cell line PT35-Tn-1-iPSC.

Embodiment 15

An induced pluripotent stem cell line PT35-Tn-2-iPSC-V4.

Embodiment 16

An induced pluripotent stem cell line PT35-Tn-2-iPSC-V4.

Embodiment 17

An induced pluripotent stem cell line PT35-Tn-2-iPSC-V9.

Embodiment 18

An induced pluripotent stem cell line PT35-Tn-3-iPSC-V3.

The present invention is illustrated by the following examples. It is to be understood that the particular examples, materials, amounts, and procedures are to be interpreted broadly in accordance with the scope and spirit of the invention as set forth herein.

EXAMPLES

Example 1—Reprogramming of Human T Stem Memory Cells into iPSCs and Differentiation of iPSCs into Mature T Cells This example shows that Human CD8 T stem memory cells can be reprogrammed into iPSCs to provide a self-renewable, regulated anti-CD19SFv CAR-T stem memory cells for adoptive tumor immunotherapy and can be induced to express transcription factors (for example, $bcl6^{hi}$; $prdm1^{lo/neg}$) such that the cells remain in a non-senescent state upon differentiation into T cells.

Example 1-1A. T-iPSC Differentiation into $CD34^+$ Cells and T Progenitors

Figure 2A:
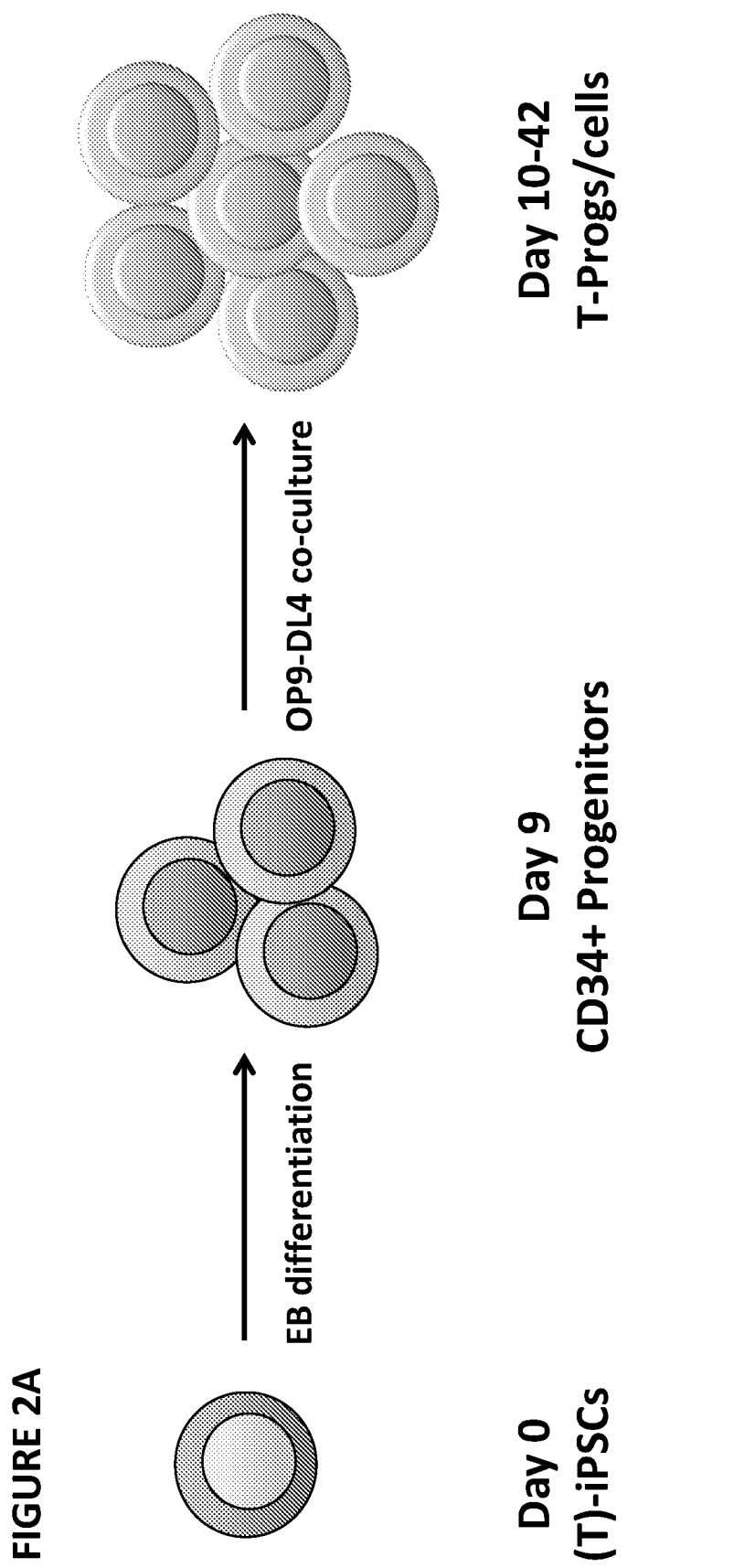
FIG. 2A. At day 0, in an exemplary embryoid body (EB) differentiation protocol, clusters of T-iPSCs are seeded in serum free animal-product free medium (APEL) differentiation medium. At day 9, $CD34^+$ hematopoietic progenitors are enriched and co-cultured on OP9-DL4 cells for induction of T lymphoid development (days 10-42).

Sendai virus was used to generate T-iPSCs. To commit T-iPSCs to a hematopoietic $CD34^+$ cell fate, two approaches were used: 1. Serum-free embryoid-body (EB) generation (Sturgeon et al. *Nat Biotechnol.* 2014; 32(6):554-61), a variation of the T-iPSC method used by Themeli et al. *Nat Biotechnol.* 2013; 31(10):928-33, using AggreWell plates (Ng et al. *Nature Protocols.* 2008; 3(5):768-76); and 2. OP9 stromal based culture (Vizcardo et al. *Cell Stem Cell.* 2013; 12(1):31-6). The comparative efficiency of T progenitors (Tprogs) from a given a Tsm-iPSC colony was unknown. Studies differentiated Tn-iPSCs and Tsm-iPSCs in parallel from single iPSC colonies using the schema shown in FIG. 2. Three Tn-iPSC (as a positive control for differentiation) and 3 Tsm-iPSC colonies were be selected from 3 donors for differentiation into $CD34^+$ cells followed by T progenitor differentiation on OP9-DL4 cells. The results allow selection of the preferred method for T stem memory re-differentiation, as tested in Example 2-1B.

Assays.

Sendai-virus free T-iPSC colony validation was performed as described as above for FIG. 1 (qRT-PCR and bisulfite sequencing for pluripotency factors; immunofluorescence; cytogenetics; teratoma formation). The percentage and number of $CD34^+$ cells under serum-free embryoid-body and 2-stage stromal culture was compared using the same colony that is expanded and split for analysis. T progenitor differentiation from CD34+ cells was performed identically from tetrameric antibody complexes recognizing CD34 and dextran-coated magnetic-purified CD34+ cells (using, for example, the EASYSEP protocol from Stem Cell Technologies, Vancouver, British Columbia, Canada). The number, differentiation profiles were quantified. The preferred approach results in the most CD45+CD7+CD5+ T progenitors at day 16 (per the methods used for FIG. 5).

Example 1-1B. T-iPSC Differentiation into Mature T Cells

At the end of maturation on OP9-DL4 cells, T progenitors have a similar frequency as thymocytes including CD4+ CD8+ (82%) and CD4+CD8− (9%) and CD4−CD8+ (4%). Mature T progenitors were exposed to conditions used to drive T naïve into T stem memory-like cells: TWS119 at 5 µM, IL-2 (100 IU/mL) and anti-CD3/28 mAb beads for 2-7 d followed by TWS119, IL7 (5-10 ng/mL) and/or IL-15 (10-25 ng/mL) to expand T stem memory cells for up to 10 days if higher numbers are needed (Gattinoni et al. *Nature Medicine.* 2011; 17(10): 1290-7).
Assays.

T stem memory cell phenotype was validated by flow cytometry, proliferation to anti-CD3/28 mAb beads and *staphylococcus* endotoxin B used to quantify the proportion and rapidity of IL-2, TNFα, and IFNγ production versus T naïve, central memory T cells, and T effector cells (Gattinoni et al. *Nature Medicine.* 2011; 17(10):1290-7), and T cell receptor excision circles, an indicator of division history of recent thymic emigrants.

Example 1-2. DARIC Transduction of Tsm-iPSCs

Example 2-1 will be modified to test the effects of lentiviral mediated DARIC transduction of Tsm-iPSCs on Tprogenitor and mature T cell development, extending results with constitutively active anti-hCD19SFv CAR in T-iPSCs (Themeli et al. *Nat Biotechnol.* 2013; 31(10):928-33.). In vitro assays. T stem memory phenotype, function and defining characteristics and for DARIC function in mature T cells using hCD19+ and hCD19− K562 cells.

Example 1-3. Prdm1 Knockdown in T-iPSCs

Figure 19A:
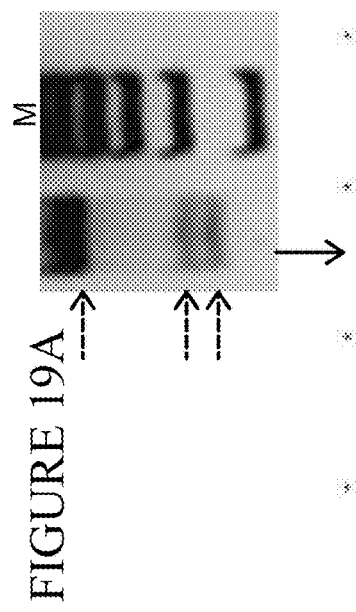
FIG. 19A shows a surveyor analysis showing cleavage products of PRDM1 with insertions and deletions (indel) indicating that in iPSC colonies treated with CRISPR reagents directed against PRDMJ, successful targeting occurred. M indicates a 100 bp DNA ladder (Mass Ruler, ThermoFisher Scientific, Waltham, MA). Dashed arrows on the Tris/Borate/EDTA (TBE) gel in the upper panel show unmodified and modified PRDM1 surveyor products. The top sequence shows an excerpt of the reverse complement of the wild type sequence of PRDM1 (SEQ ID NO:1); the additional sequences (SEQ ID NOs:2-6, from top to bottom) are from colonies of TSM-PRDM1KO-IPSC and confirm the deletion.
Figure 19B:
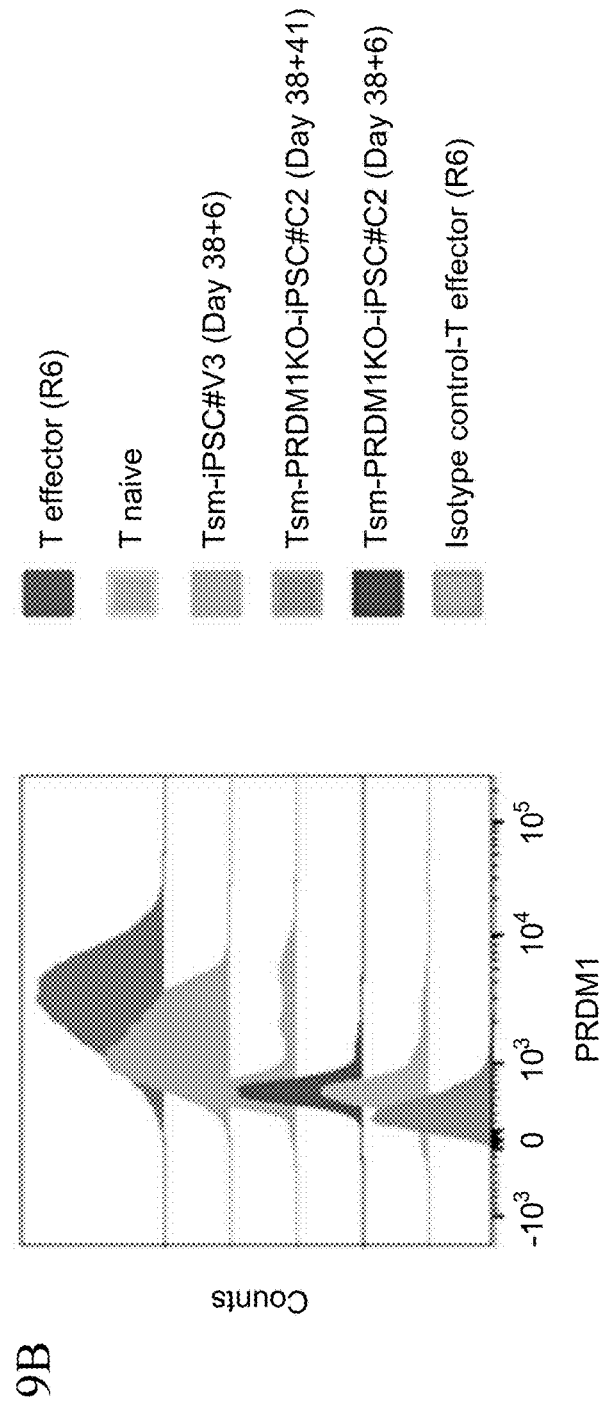
FIG. 19B shows expression of PRDM1 in T cell populations derived from iPSCs. WT Tsm-iPSC and Tsm-PRDM1KO-iPSC were differentiated into double positive (DP)-T cells. At day 38, DP-T cells were stimulated to generate Tsm cells, as described in Example 9. Flow cytometric analysis confirms loss of PRDM1 protein in Tsm-PRDM1KO-iPSC-derived T cells at post stimulation day 6 (38+6) or day 41 (38+41). T effector and T naïve cells purified from peripheral blood serve as a controls for PRDM1 expression. Isotype antibody is used as a control for background staining.
Figure 20A:
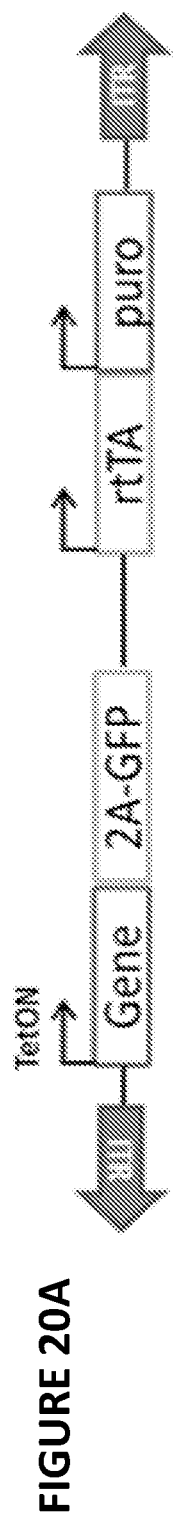
FIG. 20A shows an exemplary inducible BCL6 construct; reverse tetracycline-controlled trans activator (rtTA); puromycin (puro) provides drug resistance; 2A-GFP fusion protein; inverted terminal repeat (ITR).
Figure 20B:
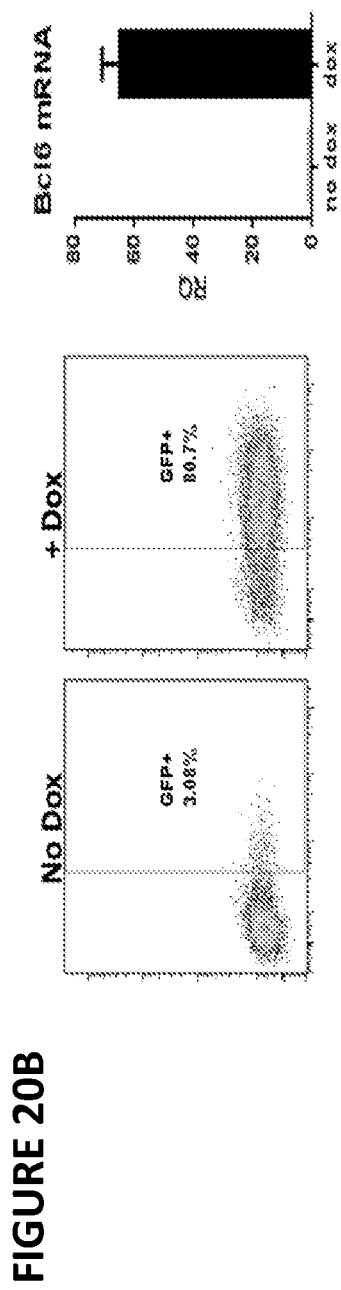
FIG. 20B shows green fluorescent protein (GFP) expression in 293T cells transfected with the BCL6 construct of FIG. 20A assayed 48 hours post-doxycycline (dox) induction.

Prdm1 knockdown in T-iPSCs (FIG. 19) was accomplished using prdm1 guide RNA and CRISPR technology and screened for knockout. In brief, the method for screening includes DNA isolation from individual targeted clones followed by PCR amplification and surveyor or restriction digestion assay. After positive clones were verified by cloning PCR fragments into TOPO cloning vector followed by DNA sequencing (Ran et al, *Nat Protoc.* 2013; 8(11):2281-2308). Because the long-term effects of high constitutive BCL6 expression levels were unknown, Tsm-iPSCs then were induced to express BCL6. FIG. 20 shows the construct design using a piggyback transposon and transposase to examine stable expression in 293T cells that were puromycin-resistant, multiply passaged and then induced with doxycycline x 48 hours. BCL6 expression post-doxycycline is indicated by a GFP surrogate and confirmed by qPCR. Tsm-iPSC colonies screened to delete or retain PRDM1 were induced to express BCL6. If indicated, colonies were selected in puromycin to enrich for the frequency of successfully transfected Tsm-iPSCs. These Tsm-iPSCs were then re-differentiated into T progenitors then T stem memory, using the methods of Example 2-1B, and levels of BCL6 tracked by flow cytometry. Mature T stem memory cells were stimulated with anti-CD3/28 mAb and IL2 for 3-7 generations to drive T stem memory cells into a T effector state, verified using established criteria (Gattinoni et al. *Nature Medicine.* 2011; 17(10):1290-7). Conversely, the effects of BCL6 knockdown using CRISPRs and inducible PRDM1 expression were examined using the reciprocal approach. By removing doxycycline, the propensity for driving T stem memory cells into a T effector state can be assessed in the same clonotypic mature T cell population.
Assays.

Flow cytometric analysis for T stem memory versus T effector state; intracellular cytokine production in response to anti-CD3 and *staphylococcus* endotoxin B; CFSE dilution for quantifying cell generations, which progressively result in T effector differentiation (Gattinoni et al. *Nature Medicine.* 2011; 17(10):1290-7). Markers of senescence can be quantified including telomere length by fluorescent in situ hybridization (FISH).

Example 2—Analysis of Gene Expression, Epigenetic Analysis and Transcription Factor Foot-Printing During In Vitro Tsm Differentiation Integrated analysis of gene expression, epigenetic analysis and transcription factor foot-printing during in vitro T stem memory differentiation allow the identification and validation of essential regulators of the Tsm state to optimize CAR or TCR therapy.

The differentiation of Tsm-iPSC clones (each from an individual donor) will be further studied. Cells will be isolated from four differentiation states (original Tsm; T-iPSC; T progs, and induced T stem memory). Global expression profiles using RNA-seq to establish the gene expression signatures of each state will be generated. Next, global profiles of chromatin accessibility using ATAC-Seq will be generated. For each sample, ~80 million aligned reads can be generated, providing deep enough coverage to 1) define global patterns of chromatin accessibility; and 2) establish transcription factor footprints, by inferring the presence of transcription factor:DNA interactions based on their "foot-prints" of chromatin accessibility. Cell number is not expected to be limiting: ATAC-seq requires as few as 500 cells (50,000 maximum) and RNA-seq requires 50,000 cells, well within the ~2×10$^6$ cells available from an apheresis sort.

The goal will be to define the expression profile unique to each cell state, and link that cell state-specific pattern of gene expression to putative transcriptional regulators defined using ATAC-seq and transcription factor foot printing. To establish cell state-specific patterns of gene expression supervised methods such as k-means clustering will be used to identify patterns of co-regulated genes that change during the differentiation process (Kurachi et al. *Nature Immunology.* 2014; 15(4):373-83) and principal components analysis will be used to identify the genes that contribute the greatest weight to the components that separate each of the four states. State-specific signatures generated in both approaches will be benchmarked against published gene expression data from T stem memory cells (Gattinoni et al. *Nature Medicine.* 2011; 17(10):1290-7). Next, transcription factor footprints will be defined using a probabilistic algorithm (e.g., Centipede) (Buenrostro et al. *Nature Methods.* 2013; 10(12):1213-8) that starts by scanning the genome for all positions with substantial similarity to a known transcription factor binding motifs. An unsupervised Bayesian mixture model will be used to infer which candidate sites for each motif are likely to be bound by a transcription factor based on characteristic patterns of chromatin accessibility. Each instance of transcription factor binding to an adjacent gene (+/−5 kb) will be mapped, establishing global regulatory networks between transcription factor binding patterns and gene expression. For instance, the set of transcription factors unique to the T stem memory state (original or differentiated from Tsm-iPSC) and adjacent (and therefore likely to regulate) genes whose expression is unique to T stem memory will be established. For example of ~1000 transcription factor motifs, there may be 200 differentially represented transcription factors in T stem memory cells, of which the most relevant will be those whose adjacent genes are over-represented in T stem memory cells. Subsequent analysis of transcription factors with footprints both in T stem memory state and in T progenitors or iPSCs may also be performed. For example, transcription factors present in T stem memory cells may also be present in iPSCs due to shared stem-like characteristics.

Perturbing the candidate regulators will permit testing of which are required for T stem memory differentiation from T-iPSCs. CRISPR technology (Osborn et al. *Hum Gene Ther.* 2015; 26(2):114-26) will be used to generate isogenic Tsm-iPSCs deleted for up to 100 transcription factors. The availability of large numbers of Tsm-iPSCs will allow comparison of wild-type versus gene-deleted Tsm-iPSCs, permitting controlled identification of transcription factors that are essential for T stem memory differentiation.

Guide RNAs (gRNAs) targeting candidate transcription factors will be generated and their efficacy validated using human T cell lines (see Example 1). Each gRNA will be expressed from its own lentiviral vectors, and transduced into Tsm-iPSC lines that have already been transduced with an inducible Cas9 expression vector engineered to be doxycycline-inducible to circumvent concerns regarding non-specific cleavage of genomic DNA and allow temporal control of gene deletion. The role of candidate T stem memory-essential transcription factors will be investigated by inducing gene knockout at the Tprogenitor→T stem memory stage and testing the effects of inducing gene deletion as early as in Tsm-iPSCs to establish temporal dependency for a given transcription factor and such assays may be broadened through the use of pooled screens (Shalem et al. *Science.* 2014; 343(6166):84-7), in which up to several hundred transcription factors could be targeted simultaneously (3-5 gRNA's per transcription factor; one vector per cell), and the relative abundance of the barcoded gRNA vectors compared in the starting pool of cells versus the resulting T stem memory pool. Transcription factors required for T stem memory differentiation would be expected to be depleted from the resulting set of barcoded vectors recovered from the T stem memory pool. Transcription factors that score in this screen would then be validated singly.

The functional genomic assessment of transcription factors implicated in the development of T stem memory from Tsm-iPSCs will assist in establishing when during the Tsm-iPSC→T stem memory differentiation each transcription factor is required, and will assist in characterizing the effect of transcription factor deletion on the number, function and phenotype of the resulting T stem memory population. For transcription factors identified as required for T stem memory differentiation, additional functional, transcriptional and epigenetic studies including ATAC-seq, RNA-seq and ChIP-seq may be performed for select transcription factors that disrupt Tsm differentiation when deleted. These studies will address the mechanism of action of transcription factors essential for T stem memory differentiation. It is possible that deletion of the transcription factors will result in a non-specific effect on T cell differentiation, that is, a transcription factor may be required not only for T stem memory differentiation but also for any T cell type to differentiate from Tsm-iPSCs. To evaluate this possibility, parallel experiments in which other types of CD8 T cells are generated from Tsm-iPSCs (e.g. T naïve, T effector) will be conducted and the effect of transcription factor deletion assessed on their differentiation. The transcription factors of greatest interest would be those that are not essential for T naïve and T effector differentiation but are required T stem memory differentiation.

Example 3—Isolation of Tn and Tsm and Generation of T-iPSC and CS-1-iPSC

Part I—Isolation of T Naïve and/or T Stem Memory from Donor Blood

The following reagents were used:
  One peripheral blood Mononuclear cell apheresis unit: isolated, Tsm/naïve CD8$^+$ T cell isolation, sort, and culture
  Sterile column running buffer and sort buffer: 0.5% BSA in 2 mM EDTA PBS without $Ca^{2+}$ or $Mg^{2+}$ Methods:
  1) Record exact volume of aphersis unit (Memorial Blood Center). Add 5 milliliters (mL) Acid Citrate Dextrose Solution (ACD-A) per 40 mL apheresis unit.
  2) Transfer blood to a sterile container and add an equal volume of ammonium chloride (Catalog #07850, StemCell Technologies, Vancouver, Canada)
  3) Mix by inverting gently; incubate on ice for 10 minutes.
  4) Centrifuge sample at 500×g at RT for 10 minutes. Remove supernatant.
  5) Wash cells with column buffer, spin at 150×g for 10 min with break off. Carefully remove supernatant.
  6) Repeat wash step until platelets are mostly removed (1-2×).
  7) Follow the StemCell Technologies EASYSEP kit instructions for Human naïve CD8 T cell selection (Catalog #19158, StemCell Technologies, Vancouver, Canada).
    a. This procedure is for processing 500 microliters (μL) to 8 mL of sample (up to 4×10$^8$ cells).
    b. Prepare the MNC suspension at a concentration of 5×10$^7$ cells/mL in recommended medium (see below).
    c. Add the EASYSEP Human Naïve CD8 T cell Enrichment cocktail at 50 μL/mL cells.
    d. Immediately add the EASYSEP Human CD45RO Depletion Cocktail at 50 μL/mL. Mix well and incubate at RT (15° C.-25° C.) for 30 minutes.
    e. Vortex the EASYSEP D2 magnetic particles for 30 seconds. Ensure that the particles are in a uniform suspension with no visible aggregates.
    f. Add EASYSEP D2 magnetic particles at 100 μl/mL cells. Mix well and incubate at RT for 10 minutes.
    g. Bring cell suspension up to 10 mLs with recommended medium. Mix cells by pipetting up and down then place tube on magnet without the cap. Set aside for 5 minutes.
    h. Pick up magnet and in one continuous motion, invert the magnet and tube, pouring off the desired fraction into a new 14 mL tube. The unwanted magnetically labeled cells will remain bound in the original tube. Leave magnet and tube inverted for 2-3 seconds, then return to upright position. Do NOT shake or blot off drops that may remain hanging from the tube.
  i. Remove original tube from magnet and replace with the tube holding desired cells and set aside for 5 more minutes for a total of 2×5 minute separations. Cells are ready for counting and staining.
8) Stain cells with viability dye (1:1000) and surface antibodies (1:200) in PBS @ RT for 20 minutes; wash.
9) Sort cells using flow cytometric analysis (Gattononi et al. *Nature Medicine*. 2011; 17(10):1290-7), excluding non-viable cells, CD14$^+$ cells, and CD19$^+$ cells; and including cells that are positive for all other markers in the antibody panel (Table 2). As shown in FIG. 1, cells that are CD95$^{hi}$, CCR7$^+$ are T stem memory cells; cells that are CD95$^{low/-}$, CCR7$^+$ are T naïve cells.

TABLE 2

Flow staining antibody panel.

| FITC or PeCy7 | BV421 | APC | BV605 | PerCP Cy 5.5 | PE | APC-eFluor780 |
|---|---|---|---|---|---|---|
| CD8a | CD45RA | CD45RO | CD62L | CCR7 | CD95 | Viability CD14, CD19, CD4 |

Part II—Generation of T-iPSC (Tn/Tsm Reprogramming)

Sorted Tn or Tsm cells were stimulated before reprogramming for 48 hours by culturing 300,000 cells at a 3:1 ratio with anti-CD3/CD28 beads, 50 IU/mL IL-2, 25 ng/mL IL-7, and 25 ng/mL IL-15 in 6-well plates (2 mL/well). Medium: 10% FBS/1% Pen-Strep RPMI 1640.

After 48 hours of stimulation, cells were transduced with CytoTune 2.0 Sendai reprogramming vectors at an MOI of 10. After 24 hours, the media was changed and cells were plated on to mouse embryonic fibroblasts (MEFS) and observed daily for colony formation. Individual colonies were selected and then cultured until loss of episomal Sendai vector was confirmed.

Part III—CS-1-iPSCs

CS-1-iPSCs were generated from human skin wild type fibroblast cells using the methods described in Park et al. *Nature*. 2008; 451(7175):141-6; Yusa et al, *Nat Methods*. 2009; 6(5):363-9; Trokovic et al, *Stem Cell Res*. 2015; 15(1):263-5; Raab et al, *Stem Cells Int*. 2014; 2014:768391.

Example 4—Methods for Differentiating iPSCs into Mature T Cells

The following reagents were used:
Conjugated Antibodies:
CD34-APC (BioLegend #343510), CD43-PE (eBioscience #12-0439-42), CD45-APC eFluor 780 (eBioscience #47-0459-42), CD45-eFluor 450 (eBioscience #48-9459-42), CD7-PE (BD Biosciences #555361), CD3-PerCP Cy 5.5 (eBioscience #45-0036-42), CD5-APC (BD Biosciences #555349), CD4-APC (BD Biosciences #555349), CD4-PE (BD Biosciences #340419), CD8a-PE Cy7 (eBioscience #25-0087-42), CD8-PacBlue (BioLegend #344718), TCRab-PE (eBioscience #12-9955-42), CD69-BV510 (BioLegend #310935), CD56-APC (eBioscience #17-0567-42), CD95-PE (BD Biosciences #555674), CD95-PE Cy7 (eBioscience #25-0959-42), CD45RA-BV421 (BioLegend #304130), CD45RO-APC (BD Biosciences #559865), CCR7-PerCP Cy5.5 (BioLegend #353220), CD62L-BV605 (BD Biosciences #562719), Granzyme-A-PerCP Cy 5.5 (BD Biosciences #B507216), Granzyme B-PE (eBioscience #12-8899-41), Perforin-FITC (BD Biosciences #B556577), Annexin V-APC (eBioscience #88-8007)

Cytokines, Small Molecules and Growth Factors:
BMP4 (R&D systems #314-BP-010), bFGF (R&D systems #233-FB), SCF (PeproTech #300-07), VEGF (Pepro Tech #100-20), IL-3 (PeproTech #200-03), Flt3L (Miltenyi Biotec #130-096-477), IL-7 (Miltenyi Biotec #130-095-362), IL-2 (NDC #:65483-116-07), CHIR99021 (Stemgent #04-0004), SB431542 (Stem Cell Technologies #72232), Y-27632 dihydrochloride (ROCK inhibitor, P212121 #LC-Y-5301-10MG), AKTi-1/2 (CAS 612847-09-3, Millipore), ADAM17 inhibitor (Incyte INCB003619).

Media and Other Reagents:
mTeSR1 (Stem Cell Technologies #05850), Stemdiff APEL medium Stem Cell Technologies #05210), Alpha-MEM (Life Technologies #12000-022, ThermoFisher Scientific, Waltham, MA), FBS (Life Technologies #10439-024, ThermoFisher Scientific, Waltham, MA), Accutase (Stem Cell Technologies #07920), DNaseI (Stem Cell Technologies #07900), Vybrant® CFDA SE Cell Tracer Kit (Life Technologies #V12883), Fixable Viability Dye eFluor 780 (eBioscience #65-0865-18)

Figure 2B:
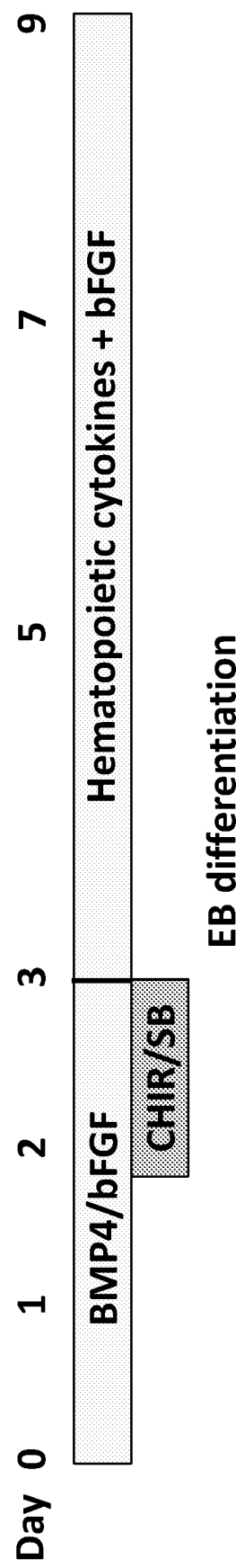
FIG. 2B. Clusters of T-iPSCs were seeded in serum free APEL differentiation medium containing Bone Morphogenetic Protein 4 (BMP4) and basic fibroblast growth factor (bFGF) for mesodermal induction, at day 1.75 Wnt signaling agonist CHIR99021 and TGF-beta signaling inhibitor SB431542 were added. At day 3, aggregates were changed to APEL heme-specification medium containing hematopoietic cytokines.
Figure 2C:
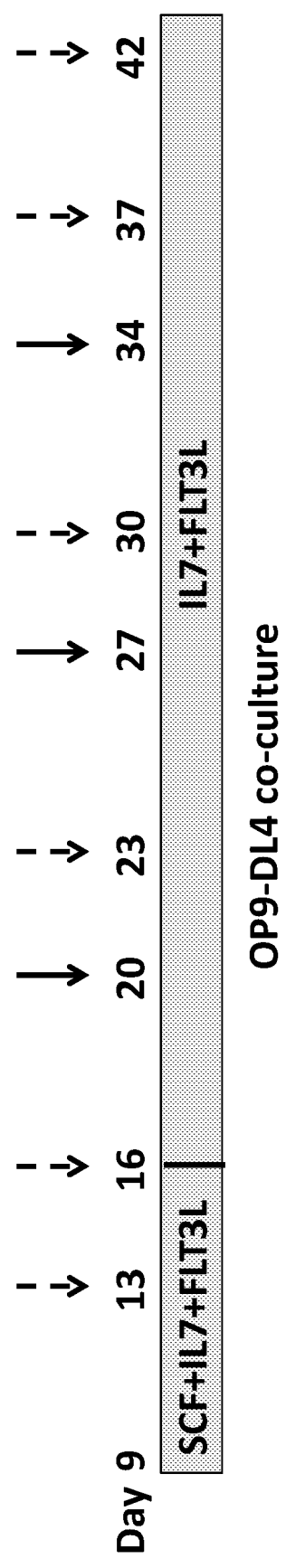
FIG. 2C. At day 9, $CD34^+$ hematopoietic progenitors are enriched using a $CD34^+$ magnetic separation kit and co-cultured on OP9-DL4 cells for induction of T lymphoid development. Solid, black arrows indicate passaging of the T progenitor cells (also referred to herein as T-progs or Tprogs) to new OP9-DL4 stromal cells. Dashed arrows indicate passaging and flow analysis of T progenitor cells.

A schematic of the treatment of cells during Days 0-9 is shown in FIG. 2B. A schematic of the treatment of cells during Days 9-42 is shown in FIG. 2C. T-iPSC and CS-1-iPSCs were generated as described in Example 3 and used to differentiate iPSCs into mature T cells as described below.

Day 0
1. Culture T-iPSC or CS-1 iPSCs on matrigel coated 6 well plates in mTeSR1 medium at 37° C. incubator with 5% $CO_2$ and 5% $O_2$.
2. Add fresh TeSR1 media to iPSC before 3-6 hours of EB generation.
3. Treat CS-1/T-iPSCs with 10 μM ROCK-inhibitor for about 30 minutes before performing the following step.
4. Wash with 2 mL PBS and add 1 mL accutase and incubate about 5 minute at room temperature, ideally colonies should start come off the plate.
5. Slowly add 2 mL PBS to each well, and carefully transfer to 50 mL conical with 5 mL serological pipet. Wash each well once with 1 mL PBS and add to conical.
6. Spin at 270×g for 5 minutes.
7. Aspirate accutase/PBS and add required amount (10 mL/10 cm plate) APEL medium containing 10% mTeSR1 with 10 ng/mL BMP-4 (R&D systems) and 5 ng/mL bFGF with 10 μM ROCK inhibitor at the final concentration (APEL differentiation medium).
8. Gently triturate pellet using serological pipet until no large clumps remain. (Take care not to over dissociate to single cell suspension).
9. Carefully transfer suspension to 10 cm non-tissue culture or low attachment dish and observe cluster size under microscope. Ideal clump sizes should be in the 5-10 cell range with minimal large clumps and minimal single cells. If necessary, triturate again with serological. Large clumps can be selectively dissociated using P1000 by swirling dish to center the larger clumps.
10. Incubate the plate at 37° C. incubator with 5% O2 on orbital shaker at ~150 rpm.

Day 1.75
11. Add CHIR99021 at a final concentration of 3-6 μM and SB431542 at a final concentration of 6 μM.
12. Incubate at 37° C. incubator with 5% $CO_2$ and 5% $O_2$ on the orbital shaker at ~150 rpm.

Day 3
13. Collect the aggregate/EBs and add to 50 mL conical tube. Wash the plate with 10 mL PBS and add to the same conical tube. Allow EBs to gravity settle for approximately 10 minute at room temperature.
14. Aspirate supernatant and add APEL differentiation medium containing 100 ng/mL SCF, 20 ng/mL VEGF, 20 ng/mL Flt3L, 20 ng/mL IL-3, and 5 ng/mL bFGF (APEL-Heme-specification medium) to settled EBs, gently resuspend and transfer to new 10 cm non-tissue culture dish.
15. Incubate at 37° C. incubator with 5% $CO_2$ and 5% $O_2$ on the orbital shaker at ~150 rpm.
16. Add 5 mL APEL Heme-specification medium on Day 5, Day 7.

Day 9
17. Collect EBs and any floating cells in 50 mL falcon tube. Wash once with 10 mL PBS and collect in the same 50 mL falcon tube.
18. Centrifuge at 400×g for 5 minutes and remove supernatants.
19. Add 5 mL accutase with 2-8 U/mL DNaseI per 10 cm plate of EB harvest and mix thoroughly using 5 mL pipette, incubate at 37° C. water bath for 20-30 minutes with periodic trituration.
20. For persistent clumps use 23 G needle and syringe and pass the cell suspension 1-2 times through it.
21. Add equal volume PBS and pass through 70 μm filter and centrifuge 400×g for 5 minutes.
22. Resuspend the pellet using 2 mL of α-MEM complete medium.
23. Count cells, take out about ~100K cells for flow analysis.
24. Centrifuge remaining cells at 1200×g for 3 minutes.
25. Resuspend pellet in appropriate volume of α-MEM complete medium for CD34 magnetic separation using EASYSEP hESC-Derived CD34 Positive Selection Kit (Stem Cell Technologies, Vancouver, British Columbia).

Day 9-42
26. Seed 7-10×$10^3$/$cm^2$ magnetically separated $CD34^+$ hematopoietic progenitor cells on 4-6×$10^3$/$cm^2$ OP9-DL4 cells in α-MEM complete medium with 100 ng/mL SCF, 5 ng/mL IL-7, 10 ng/mL Flt3L (T-differentiation media with SCF).
27. Add 5 mL T-differentiation media with SCF at day 12.
28. Passage T-progenitors on the new plate with T-differentiation media with SCF at day 14.
29. Passage T-progenitors on the new freshly plated OP9-DL4 cells every 4 to 5 days with T-differentiation media with only 5 ng/mL IL-7, 10 ng/mL Flt3L from day 16 onward.
30. Flow-analyze the expression profile of T-lymphocyte development markers on suitable time points.

Example 5—T Cell Differentiation

Tsm-iPSC and Tn-iPSCs were derived as described in Example 3. Cells were differentiated as described in Example 4. EBs were dissociated at day 9 of differentiation, $CD34^+$ cells were enriched using CD34 EASYSEP, and $CD34^+$ hematopoietic progenitors were co-cultured with OP9-DL4 stromal cells.

At day 23 (9+14), cells were analyzed for T/NKT cell phenotype and results are shown in FIG. 21.

Alternatively, at day 16 (9 days of EB differentiation+7 days of OP9-DL4 co-culture), the T progenitors were enriched by removing OP9-DL4 cells using anti-CD29 biotin conjugated antibodies (MCA2298B, AbD Serotech, Kidlington, UK) using EASYSEP biotin positive selection kit (#18559, Stem Cell Technologies, Vancouver, British Columbia). Cells that did not bind to the antibodies formed a "CD29 depleted fraction" and cells that bound to the antibodies formed a "CD29 enriched fraction." Each fraction was plated on GFP-expressing OP9-DL4 cells. 24 hours later, the viability of the GFP-expressing OP9-DL4 cells was assessed by microscopy. The CD29 depleted fraction (which includes NKT/T cells) destroyed almost all stromal cells (OP9-DL4); however, although the CD29 enriched fraction retained a small number of T/NKT cells, destruction of the GFP-expressing stromal cells was not observed, suggesting the effector:target (NKT:OP9-DL4) ratio is important. Results are shown in FIG. 22.

Example 6—Effects of CHIR Treatment Compared to CHIR+SB Treatment on In-Vitro T Cell Development Tsm-iPSC and Tn-iPSCs were derived as described in Example 3. Cells were differentiated as described in Example 4. Tsm-iPSC- and Tn-iPSC-derived embryoid bodies (EBs) were dissociated at day 9 of differentiation, $CD34^+$ cells were enriched using CD34 EASYSEP, and $CD34^+$ hematopoietic progenitors were co-cultured with OP9-DL4 stromal cells. During day 1.75 to day 3, EBs were treated either with CHIR99021 alone or CHIR99021 and SB431542.

During first phase of EB differentiation (FIG. 2B) EBs were treated with CHIR99021 and SB431542 on day 1.75 to day 3 because, during early hematopoietic differentiation activation of the Wnt signaling and inhibition of TGF-beta pathway guide iPSC cell differentiation towards definitive blood progenitors from which T cells are formed.

Comparative analysis of phenotype and absolute cell number quantification of T cells were performed at various time points. Results are shown in FIGS. 23 to 27. Combined CHIR99021 and SB431542 treatment during EB differentiation was observed to result in an increase in absolute cell numbers of T progenitors/cells.

Example 7—CS-1 iPSC Differentiation into T Progenitors/Cells

CS-1-iPSCs-derived embryoid bodies were differentiated as described in Example 4 with the following modifications: CS-1-iPSC-derived embryoid bodies were treated with DMSO or CHIR99021 between day 2 and day 3 and differentiated for 9 days. $CD34^+$ cells were enriched and co-cultured on OP9-DL4 cells and analyzed for T cell development at day 18 or day 22.

Figure 28:
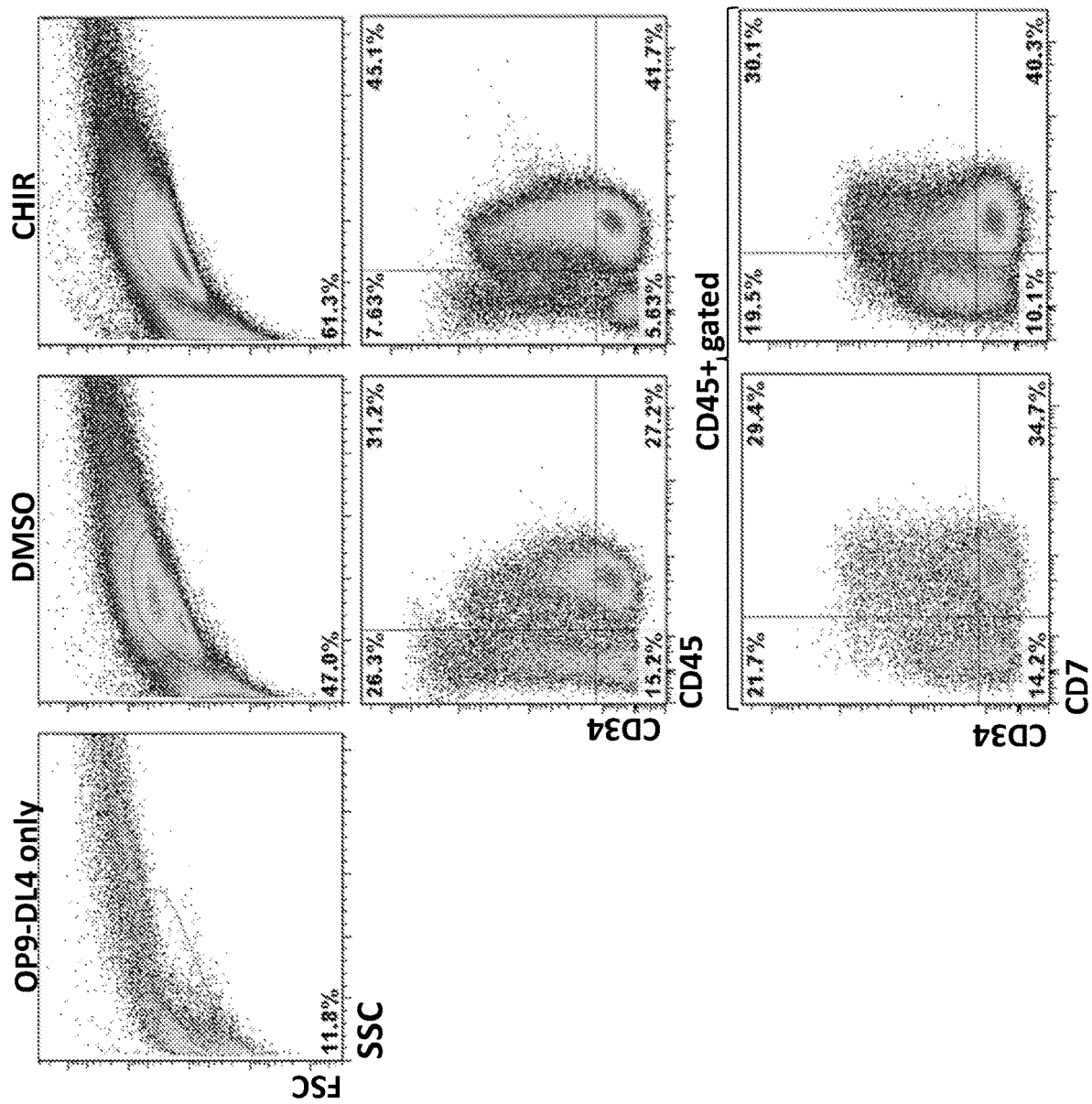
FIG. 28 shows exemplary flow cytometric analysis at day 18 (9 days EB+9 days OP9-DL4 co-culture) co-culture. CS-1-iPSC derived aggregates, prepared as described in Example 7, were treated with DMSO or CHIR99021 from day 1.75 to day 3 of EB differentiation. EBs were dissociated at day 9 of differentiation, and CD34$^+$ cells were enriched using CD34 EASYSEP. The resulting CD34$^+$ hematopoietic progenitors were co-cultured with OP9-DL4 stromal cells for 9 additional days. Flow cytometric analysis was performed on day 18 (9 days EB+9 days OP9-DL4 co-culture), the desired lymphocyte population was gated stringently, and cells were analyzed for the indicated markers.

As shown in FIG. 28, CS-1-iPSC-derived T progenitors showed expression of CD45 and CD7 but failed to express markers of further maturation including CD5 and CD3.

Example 8—iPSC Differentiation into T Progenitors/Cells iPSCs-derived embryoid bodies were differentiated as described in Example 4 with the following modifications:

iPSC-derived embryoid bodies were treated with DMSO or CHIR99021 between day 2 and day 3 and differentiated for 9 days. CD34+ cells were enriched and co-cultured on OP9-DL4 cells and analyzed for T cell development at day 18 or day 22.

Example 9—Methods for Differentiating iPSCs into T Stem Cell Memory (Tsm) Cells

Figure 29:
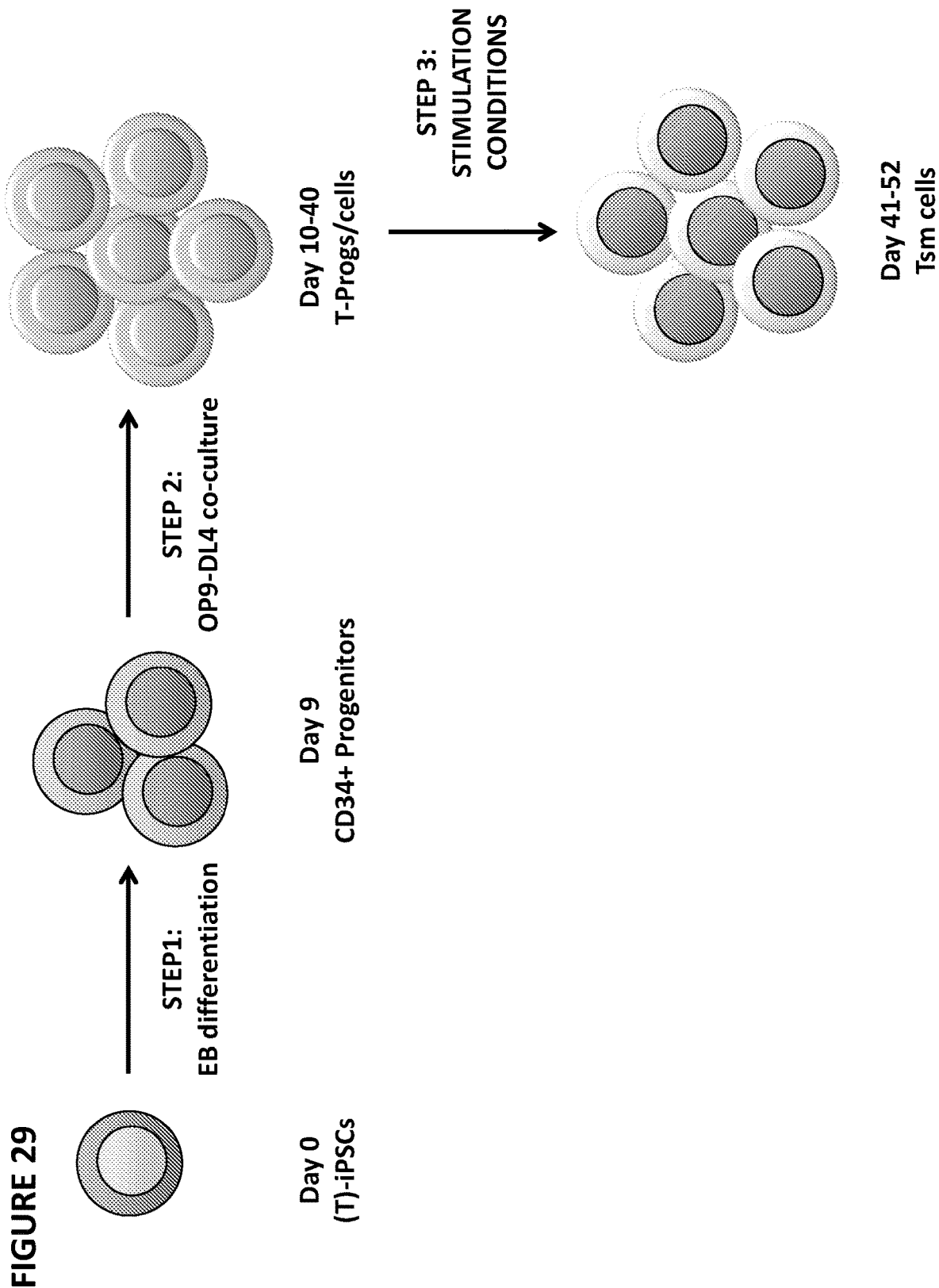
FIG. 29 shows an exemplary directed differentiation scheme for generation of T cells from T-iPSC. In the first step (STEP I), an embryoid body (EB) differentiation protocol, clusters of T-iPSCs are seeded in serum free animal-product free medium (APEL) differentiation medium. In the second step (STEP II) of the protocol, at day 9, CD34$^+$ hematopoietic progenitors are enriched and co-cultured on OP9-DL4 cells for induction of T lymphoid development (days 10-42). In the third step (STEP III) CD4/CD8 double positive (DP) T cells were stimulated using culture conditions and anti-CD3/28 antibodies conjugated micro beads to generate a T stem cell memory (Tsm) phenotype.
Figure 30:
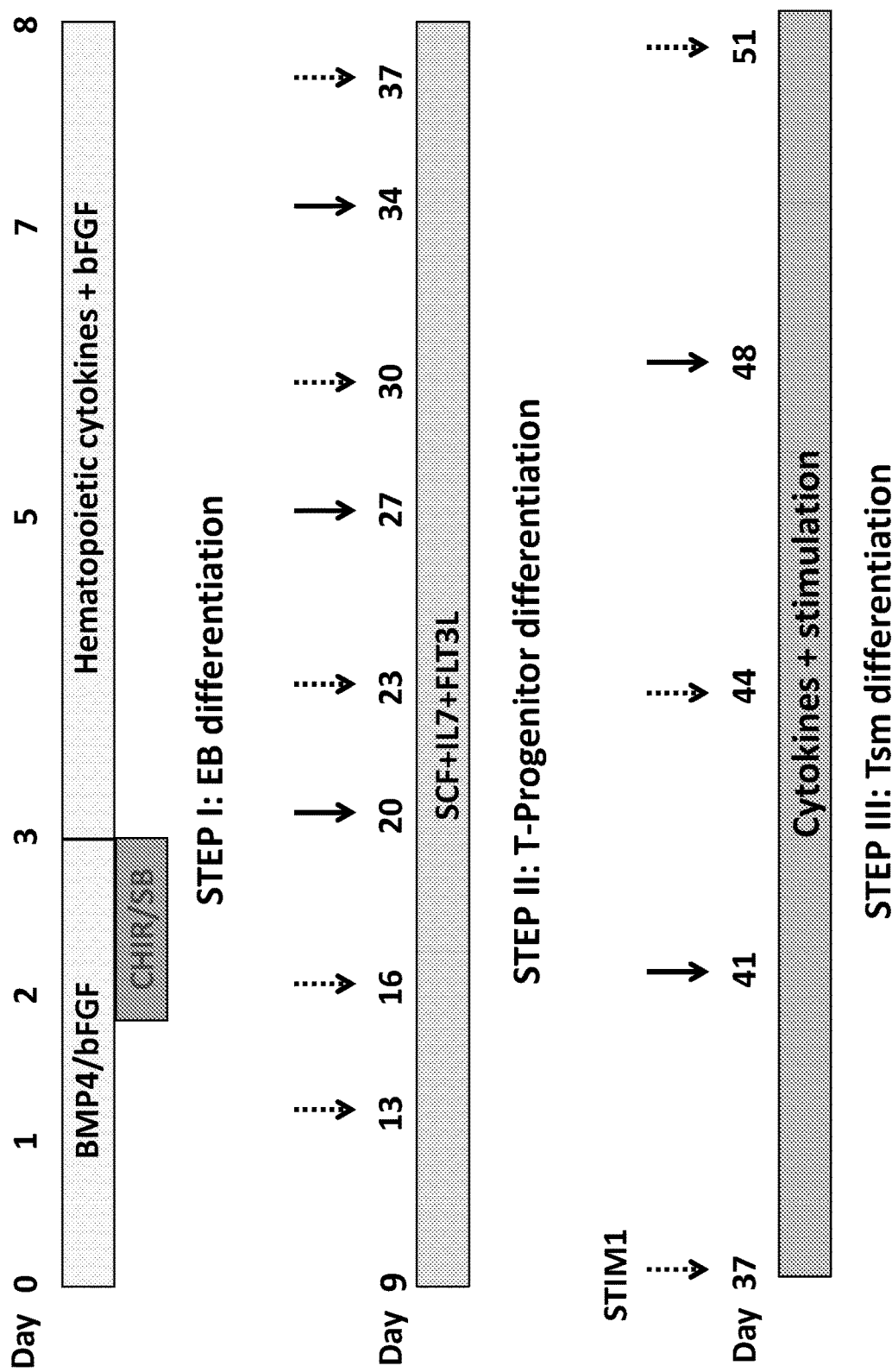
FIG. 30 shows an exemplary directed differentiation scheme for generation of T cells from T-iPSC. In STEP I, clusters of T-iPSCs were seeded in serum free APEL differentiation medium containing BMP4 and bFGF for mesodermal induction; at day 1.75 Wnt signaling agonist CHIR99021 and TGF-beta signaling inhibitor SB431542 were added. At day 3, aggregates were changed to APEL heme-specification medium containing hematopoietic cytokines. In STEP II, at day 9, CD34$^+$ hematopoietic progenitors were enriched using CD34$^+$ magnetic separation kit and co-cultured on OP9-DL4 cells for induction of T lymphoid development. Solid, black arrows indicate passaging of the T progenitor cells (Tprogs) to new OP9-DL4 stromal cells. Dashed arrows indicate passaging and flow analysis of T progenitor cells. In STEP 3, double positive T (DP-T) cells were enriched and stimulated using anti-CD3/28 antibody conjugated micro beads with defined cultured conditions with small molecules and cytokines to generate Tsm cell phenotype. Solid, black arrows indicate half media change and dashed arrows indicate flow analysis time points.

The reagents described in Example 4 were used, and iPSCs were differentiated into T stem cell memory (Tsm) cells, as described below. A schematic of the treatment of cells is shown in FIGS. 29 and 30. A schematic of the treatment of the cells during Days 0-9 is shown in FIG. 30, STEP I: EB differentiation. A schematic of the treatment of cells during Days 9-42 is shown in FIG. 30, STEP II: T-Progenitor differentiation. A schematic of the treatment of cells during Days 37-52 is shown in FIG. 30, STEP III: Tsm differentiation.

Day 0 (STEP I)
1. Culture T-iPSC or CS-1 iPSCs on matrigel coated 6 well plates in mTeSR1 medium at 37° C. incubator with 5% $CO_2$ and 5% $O_2$.
2. Add fresh TeSR1 media to iPSC before 3-6 hours of EB generation.
3. Treat CS-1/T-iPSCs with 10 μM ROCK-inhibitor for about 30 minutes before performing the following step.
4. Wash with 2 mL PBS and add 1 mL accutase and incubate about 5 minute at room temperature, ideally colonies should start come off the plate.
5. Slowly add 2 mL PBS to each well, and carefully transfer to 50 mL conical with 5 mL serological pipet. Wash each well once with 1 mL PBS and add to conical.
6. Spin at 270×g for 5 minutes.
7. Aspirate accutase/PBS and add required amount (10 mL/10 cm plate) APEL medium containing 10% mTeSR1 with 10 ng/mL BMP-4 (R&D systems) and 5 ng/mL bFGF with 10 μM ROCK inhibitor at the final concentration (APEL differentiation medium).
8. Gently triturate pellet using serological pipet until no large clumps remain. (Take care not to over dissociate to single cell suspension).
9. Carefully transfer suspension to 10 cm non-tissue culture or low attachment dish and observe cluster size under microscope. Ideal clump sizes should be in the 5-10 cell range with minimal large clumps and minimal single cells. If necessary, triturate again with serological. Large clumps can be selectively dissociated using P1000 by swirling dish to center the larger clumps.

Incubate the plate at 37° C. incubator with 5% $O_2$ on orbital shaker at ~150 rpm.

Day 1.75
1. Add CHIR99021 to a final concentration of 3 μM to 6 μM and SB431542 to a final concentration of 6
2. Incubate at 37° C. incubator with 5% $CO_2$ and 5% $O_2$ on the orbital shaker at ~150 rpm.

Day 3
3. Collect the aggregate/EBs and add to 50 mL conical tube. Wash the plate with 10 mL PBS and add to the same conical tube. Allow EBs to gravity settle for approximately 10 minute at room temperature.
4. Aspirate supernatant and add APEL differentiation medium containing 100 ng/mL SCF, 20 ng/mL VEGF, 20 ng/mL Flt3L, 20 ng/mL IL-3, and 5 ng/mL bFGF (APEL-Heme-specification medium) to settled EBs, gently re-suspend and transfer to new 10 cm non-tissue culture dish.
5. Incubate at 37° C. incubator with 5% $CO_2$ and 5% $O_2$ on the orbital shaker at ~150 rpm.
6. Add 5 mL APEL Heme-specification medium on Day 5, Day 7.

Day 9 (STEP II)
7. Collect EBs and any floating cells in 50 mL falcon tube. Wash once with 10 mL PBS and collect in the same 50 mL falcon tube.
8. Centrifuge at 400×g for 5 minutes and remove supernatants.
9. Add 5 mL accutase and 5 mL Trypsin-EDTA per 10 cm plate of EB harvest and mix thoroughly using 5 mL pipette, incubate at 37° C. water bath for 20-30 minutes with periodic vortexing.
10. For persistent clumps use 18 G followed by 23 G needle and syringe and pass the cell suspension 1-2 times through it.
11. Add equal volume PBS and pass through 70 μm filter and centrifuge 400×g for 5 minutes.
12. Resuspend the pellet using 2 mL of α-MEM complete medium.
13. Count cells, take out about ~100K cells for flow analysis.
14. Centrifuge remaining cells at 1200×g for 3 minutes.
15. Resuspend pellet in appropriate volume of α-MEM complete medium for CD34 magnetic separation using EASYSEP hESC-Derived CD34 Positive Selection Kit (Stem Cell Technologies, Vancouver, British Columbia).

Day 9-42
16. Seed 7-10×$10^3$/$cm^2$ magnetically separated CD34+ hematopoietic progenitor cells on 4-6×$10^3$/$cm^2$ OP9-DL4 cells in α-MEM complete medium with 100 ng/mL SCF, 5 ng/mL IL-7, 10 ng/mL Flt3L (T-differentiation media with SCF). Use 3 mL media per well of 6 well plate.
17. Add 2 mL T-differentiation media with SCF at day 12.
18. Passage T-progenitors on the new plate with T-differentiation media with SCF at day 14.
19. Passage T-progenitors on the new freshly plated OP9-DL4 cells every 4 to 5 days with T-differentiation media with 5 ng/mL IL-7, 10 ng/mL Flt3L and 10 ng/mL SCF from day 16 onward.
20. Flow-analyze the expression profile of T-lymphocyte development markers on suitable time points.

Day 37-52 (STEP III)
1. Between day 37-42, cells were washed using 2 mL PBS. Pass the PBS through 40 μm filter into sterile falcon tube.
2. Add 1 mL accutase per well of 6 well plate and incubate at 37° C. for 5 minutes.
3. Dissociate cell clumps using P1000 pipette and pass through the filter.
4. Wash the well using 2 mL PBS and collect into the same tube with 40 μm filter.
5. Centrifuge at 400×g for 5 minutes and re-suspend the pellet in 2 mL of α-MEM complete medium.
6. Count cells, take out about ~200K cells for flow analysis.
7. Centrifuge remaining cells at 1200×g for 3 minutes.
8. DP-T cells were enriched using CD45 enrichment kit (Stem Cell Technologies, Vancouver, British Columbia).

9. 1×10⁵ CD45⁺ DP T cells were cultured in X-vivo media (Stem Cell Technologies, Vancouver, British Columbia) along with cytokines 10 ng/mL SCF, 10 ng/mL IL-7, 10 ng/mL Flt3L, 10 ng/mL IL-15, 50 ng/mL IL-21 (for first three days), 300 IU IL-2 and stimulated using anti-CD3/28 antibody conjugated micro beads (Life Technologies) at 3:1 ratio to the DP-T cells, in the presence of 5 µM TWS119, 10 µM ADAM17 inhibitor, and 2 µM AKT inhibitor.
10. Every 3 days post stimulation half media were changed with 2× cytokines.
11. Day 6 post stimulation, cells were flow cytometrically analyzed for T naïve or T stem cell memory phenotypes.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

What is claimed is:

1. A method comprising:
isolating at least one stem memory T cell (Tsm);
expanding the Tsm in vitro;
reprogramming at least a portion of the expanded Tsms into iPSCs; and
differentiating at least a portion of the iPSCs into T cells, wherein differentiating comprises forming embryoid bodies (EBs) from the iPSCs and culturing the iPSCs in the presence of a Wnt pathway activator and a TGFβ signaling inhibitor, wherein the differentiated T cells comprise a Tsm.

2. The method of claim 1, wherein the method comprises culturing the iPSCs undergoing differentiation in the presence of at least one of basic fibroblast growth factor (bFGF), bone morphogenetic protein (BMP)-4, a hematopoietic cytokine, stromal cells expressing a Notch ligand, media comprising a soluble Notch ligand, stem cell factor (SCF), IL-7, and FMS-like tyrosine kinase 3 ligand (Flt3L).

3. The method of claim 1, wherein the method comprises culturing the iPSCs undergoing differentiation sequentially with:
media comprising at least one of bFGF and BMP-4;
media comprising at least one of a Wnt pathway activator and a TGFβ signaling inhibitor;
media comprising at least one hematopoietic cytokine; and
media comprising at least one of SCF, IL-7, and Flt3L.

4. The method of claim 1, wherein the method comprises culturing the iPSCs undergoing differentiation sequentially in:
media comprising animal-product free medium (APEL) differentiation medium; and
media comprising a stromal cell expressing a Notch ligand or media comprising a soluble Notch ligand.

5. The method of claim 1, wherein the differentiating comprises enriching the iPSCs for CD34$^+$ cells.

6. The method of claim 1, the method comprising stimulating the iPSCs undergoing differentiation via at least one of CD3 and CD28.

7. The method of claim 6 wherein differentiating comprises enriching the iPSCs for cells expressing CD45.

8. The method of claim 6, the method comprising simulating the iPSCs undergoing differentiation in media comprising at least one of SCF, IL-7, Flt3L, IL-15, IL-21, IL-2, a Glycogen synthase kinase 3 (GSK3) inhibitor, and an AKT inhibitor.

9. The method of claim 1, wherein the iPSCs comprise a chimeric antigen receptor-expressing cell.

10. The method of claim 1, wherein differentiating at least a portion of the iPSCs into T cells comprises regulating BCL6 and PRDM1 expression.

11. The method of claim 10, wherein regulating BCL6 and PRDM1 expression comprises inducing BCL6 upregulation and PRDM-1 down-regulation.

12. The method of claim 10, wherein regulating BCL6 and PRDM1 expression comprises BCL6 knockdown using CRISPRs and inducible PRDM1 expression.

13. The method of claim 1, wherein the Wnt pathway activator comprises a Wnt signaling agonist.

14. The method of claim 13, wherein the Wnt signaling agonist comprises CHIR99021, CHIR-98014, LY2090314, BIO, IM-12, 3F8, A 1070722, CHIR99021 trihydrochloride, L803-mts, SB 216763, SB415286, TC-G 24, TWS119, or a combination thereof.

15. The method of claim 14, wherein the Wnt signaling agonist comprises CHIR99021.

16. The method of claim 1, wherein the TGFB signaling inhibitor comprises SB43 1542 EW-7197, LY2157299, LY2109761, SB525334, SD-208, SB505124, GW788388, RepSox, or a combination thereof.

17. The method of claim 16, wherein the TGFβ signaling inhibitor comprises SB431542.

18. The method of claim 1, wherein the at least one isolated Tsm expresses CD3, CD8, CD45RA, CD62L, CCR7, and CD95.

* * * * *

```
                        SEQUENCE LISTING

<160> NUMBER OF SEQ ID NOS: 6

<210> SEQ ID NO 1
<211> LENGTH: 100
<212> TYPE: DNA
<213> ORGANISM: HOMO SAPIENS

<400> SEQUENCE: 1
aaagaaaata aagttttcag atcaatttca gaattaaaaa aaaaaaattc aagttcctta      60
ccaaggtcgt acccacacgt ttttccaagc aaatatccaa                           100

<210> SEQ ID NO 2
<211> LENGTH: 87
<212> TYPE: DNA
<213> ORGANISM: artificial
<220> FEATURE:
<223> OTHER INFORMATION: colony of TSM-PRDM1KO-IPSC

<400> SEQUENCE: 2
aaagaaaata aagttttcag atcaatttca gaattaaaaa aaaaaaattc aagttcctta      60
ccaaggtttt tccaagcaaa tatccaa                                         87

<210> SEQ ID NO 3
<211> LENGTH: 87
<212> TYPE: DNA
<213> ORGANISM: artificial
<220> FEATURE:
<223> OTHER INFORMATION: colony of TSM-PRDM1KO-IPSC

<400> SEQUENCE: 3
aaagaaaata aagttttcag atcaatttca gaattaaaaa aaaaaaattc aagttcctta      60
ccaaggtttt tccaagcaaa tatccaa                                         87

<210> SEQ ID NO 4
<211> LENGTH: 87
<212> TYPE: DNA
<213> ORGANISM: artificial
<220> FEATURE:
<223> OTHER INFORMATION: colony of TSM-PRDM1KO-IPSC

<400> SEQUENCE: 4
aaagaaaata aagttttcag atcaatttca gaattaaaaa aaaaaaattc aagttcctta      60
ccaaggtttt tccaagcaaa tatccaa                                         87
```

```
<210> SEQ ID NO 5
<211> LENGTH: 87
<212> TYPE: DNA
<213> ORGANISM: artificial
<220> FEATURE:
<223> OTHER INFORMATION: colony of TSM-PRDM1KO-IPSC

<400> SEQUENCE: 5
aaagaaaata aagttttcag atcaatttca gaattaaaaa aaaaaaattc aagttcctta        60
ccaaggtttt tccaagcaaa tatccaa                                           87

<210> SEQ ID NO 6
<211> LENGTH: 87
<212> TYPE: DNA
<213> ORGANISM: artificial
<220> FEATURE:
<223> OTHER INFORMATION: colony of TSM-PRDM1KO-IPSC

<400> SEQUENCE: 6
aaagaaaata aagttttcag atcaatttca gaattaaaaa aaaaaaattc aagttcctta        60
ccaaggtttt tccaagcaaa tatccaa                                           87
```